(12) United States Patent
Bromley et al.

(10) Patent No.: US 8,414,914 B2
(45) Date of Patent: *Apr. 9, 2013

(54) COMPOSITIONS FOR MUCOSAL DELIVERY OF AGENTS

(75) Inventors: Philip James Bromley, Fullerton, CA (US); Lee Nickols Huang, Diamond Bar, CA (US)

(73) Assignee: Virun, Inc., Walnut, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/507,928

(22) Filed: Aug. 6, 2012

(65) Prior Publication Data

US 2012/0308644 A1    Dec. 6, 2012

Related U.S. Application Data

(63) Continuation of application No. 12/930,978, filed on Jan. 20, 2011, now Pat. No. 8,252,323, which is a continuation of application No. 11/155,262, filed on Jun. 16, 2005, now Pat. No. 7,906,140.

(60) Provisional application No. 60/580,877, filed on Jun. 17, 2004.

(51) Int. Cl.
*A61K 38/00* (2006.01)

(52) U.S. Cl.
USPC .............................................. 424/450; 514/1

(58) Field of Classification Search ........................ None
See application file for complete search history.

(56) References Cited

U.S. PATENT DOCUMENTS

| | | | |
|---|---|---|---|
| 4,740,365 A | 4/1988 | Yukimatsu et al. | 424/435 |
| 4,889,720 A | 12/1989 | Konishi et al. | 424/447 |
| 4,900,552 A | 2/1990 | Sanvordeker et al. | 424/422 |
| 4,921,706 A | 5/1990 | Roberts et al. | 424/450 |
| 5,033,252 A | 7/1991 | Carter | 534/25 |
| 5,052,558 A | 10/1991 | Carter | 206/439 |
| 5,154,924 A | 10/1992 | Friden | 424/179.1 |
| 5,178,878 A | 1/1993 | Wehling et al. | 424/466 |
| 5,182,107 A | 1/1993 | Friden | 424/85.91 |
| 5,234,957 A | 8/1993 | Mantelle et al. | |
| 5,298,246 A | 3/1994 | Yano et al. | |
| 5,323,907 A | 6/1994 | Kalvelage | 206/531 |
| 5,527,527 A | 6/1996 | Friden | 424/178.1 |

(Continued)

FOREIGN PATENT DOCUMENTS

| CA | 2229286 | 8/1999 |
|---|---|---|
| WO | WO 2006/009825 | 1/2006 |

(Continued)

OTHER PUBLICATIONS

U.S. Appl. No. 60/527,962, filed Dec. 8, 2003, Masters et al.

(Continued)

*Primary Examiner* — Anand Desai
*Assistant Examiner* — Melissa Mercier
(74) *Attorney, Agent, or Firm* — McKenna Long & Aldridge LLP; Stephanie Seidman

(57) ABSTRACT

Compositions and methods for mucosal delivery of agents are provided. The compositions are intended for administration to mucosal surface, such as oral, gastrointestinal and nasal mucosa. The compositions provided contain one or more mucoadhesive proteins and an agent to be delivered. Methods for delivery of agents using the compositions provided herein are also provided.

24 Claims, 1 Drawing Sheet

U.S. PATENT DOCUMENTS

| | | | |
|---|---|---|---|
| 5,620,708 A | 4/1997 | Amkraut et al. | 424/491 |
| 5,672,683 A | 9/1997 | Friden et al. | 530/350 |
| 5,702,727 A | 12/1997 | Amkraut et al. | 424/491 |
| 5,744,155 A | 4/1998 | Friedman et al. | 424/434 |
| 5,833,988 A | 11/1998 | Friden | 424/178.1 |
| 5,977,307 A | 11/1999 | Friden et al. | 530/350 |
| 5,993,846 A | 11/1999 | Friedman et al. | 424/434 |
| 6,071,535 A | 6/2000 | Hayward et al. | 424/450 |
| 6,329,508 B1 | 12/2001 | Friden | 530/387.3 |
| 6,383,513 B1 | 5/2002 | Watts et al. | 424/450 |
| 6,426,362 B1 | 7/2002 | Miller et al. | 514/458 |
| 6,475,511 B2 | 11/2002 | Gohlke et al. | 424/441 |
| 6,552,024 B1 | 4/2003 | Chen et al. | 514/252.16 |
| 6,638,521 B2 | 10/2003 | Dobrozsi et al. | 424/434 |
| 6,749,863 B1 | 6/2004 | Chang et al. | 424/450 |
| 6,905,688 B2 | 6/2005 | Rosen et al. | 424/192.1 |
| 6,926,898 B2 | 8/2005 | Rosen et al. | 424/192.1 |
| 6,946,134 B1 | 9/2005 | Rosen et al. | 424/192.1 |
| 6,994,857 B2 | 2/2006 | Rosen et al. | 424/192.1 |
| 7,179,484 B2 | 2/2007 | Singh | 424/450 |
| 7,906,140 B2 * | 3/2011 | Bromley et al. | 424/450 |
| 8,252,323 B2 * | 8/2012 | Bromley et al. | 424/450 |
| 8,282,977 B2 | 10/2012 | Bromley | 426/72 |
| 2003/0170311 A1 | 9/2003 | Russell | 424/489 |
| 2003/0171259 A1 | 9/2003 | Modi et al. | 514/2 |
| 2003/0171267 A1 | 9/2003 | Rosen et al. | 514/12 |
| 2003/0219472 A1 | 11/2003 | Pauletti et al. | 424/449 |
| 2003/0221201 A1 | 11/2003 | Prior et al. | 800/7 |
| 2003/0226155 A1 | 12/2003 | Sadeghi et al. | 800/7 |
| 2004/0010134 A1 | 1/2004 | Rosen et al. | 536/23.5 |
| 2004/0023334 A1 | 2/2004 | Prior | 435/69.7 |
| 2004/0037809 A1 | 2/2004 | Quay et al. | 424/856 |
| 2004/0077540 A1 | 4/2004 | Quay | 514/12 |
| 2005/0196440 A1 | 9/2005 | Masters et al. | 424/464 |
| 2005/0197495 A1 | 9/2005 | Naidu | 530/400 |
| 2005/0281772 A1 | 12/2005 | Bromley et al. | 424/70.14 |
| 2006/0084794 A1 | 4/2006 | Rosen et al. | 530/363 |
| 2006/0093594 A1 | 5/2006 | Naidu | 424/93.45 |
| 2009/0297491 A1 | 12/2009 | Bromley | 424/94.1 |
| 2009/0297665 A1 | 12/2009 | Bromley | 426/72 |
| 2009/0317532 A1 | 12/2009 | Bromley | 426/590 |
| 2010/0041622 A1 | 2/2010 | Bromley et al. | 514/52 |
| 2011/0117184 A1 | 5/2011 | Bromley | 424/450 |
| 2011/0236364 A1 | 9/2011 | Bromley | 424/94.1 |
| 2012/0016026 A1 | 1/2012 | Bromley | 514/560 |

FOREIGN PATENT DOCUMENTS

| | | |
|---|---|---|
| WO | WO 2009/117151 | 9/2009 |
| WO | WO 2009/117152 | 9/2009 |
| WO | WO 2010/008475 | 1/2010 |
| WO | WO 2010/019255 | 2/2010 |
| WO | WO 2011/119228 | 9/2011 |

OTHER PUBLICATIONS

U.S. Appl. No. 60/887,754, filed Feb. 1, 2007, Borowy-Borowski et al.

Almeida et al., "Nasal delivery of vaccines," Journal of Drug Targeting, 3:456-467 (1996).

Alonso et al., "Biodegradable nanostructures as carriers for transmucosal delivery," Presented at the 226th ACS National Meeting, New York, NY, Sep. 8, 2003. Abstract. 1 page.

Ansel, H., Introduction to Pharmaceutical Dosage Forms, Fourth Edition, Philadelphia: Lea& Febiger, p. 126 (1985).

Budavari, et al.(Eds.) The Merck Index, 12th Edition, Whitehouse Station, N.J :Merck & Co., pp. THER-1 to THER-28, (1996).

Drug Delivery Technology, Alkaline Acidic Triggering Effect pamphlet, Archimedes Laboratories, Inc., City of Industry, CA, 2 pages, Sep. 2005.

Drug Delivery Technology, Pre-Clinical Abstract, Oral Pharmacokinetics of MAPED (Mucosa Adhesive Protein Engineered Drugs) Bound in Human Recombinant Insulin, Archimedes Laboratories, Inc., City of Industry, CA, 6 pages, Sep. 2005.

Drug Delivery Technology, Undenatured Protein pamphlet, 2 pages, Archimedes Laboratories, Inc., City of Industry, CA, 2 pages, Sep. 2005.

Ectotropin-6™ Website Printout, found at: www.ibe-technology.com/ectotropin.htm [retrieved on Jan. 20, 2006].

Fehniger et al., "Exploring the context of the lung proteome within the airway mucosa following allergen challenge," J Proteome Res. 3(2):307-320 (2004).

Good, R., "Surface free energy of solids and liquids: Thermodynamics, molecular forces, and structure," Journal of Colloid and Interface Science. 59(3):398-419 (1977).

Gu et al., "Binding of acrylic polymers to mucin/epithelial surfaces: structure-property relationships," Critical Reviews in Therapeutic Drug Carrier Systems 5(1): 21-67 (1988).

Handbook of Pharmaceutical Excipients, "Lecithin," Published by American Pharmaceutical Association:Washington DC and the Pharmaceutical Society of Great Britain:London, p. 165 (1986).

HexaTropin-6™ Website Printout, found at: www.ibe-technology.com/hexatropin.htm [retrieved on Jan. 20, 2006].

Lehr et al., "Visualization studies of the mucoadhesive interface," Journal of Controlled Release, 18:249-260 (1992).

Nogrady, M., Medicinal Chemistry a Biochemical Approach, Oxford University Press, New York, pp. 388-392 (1985).

Oratropin-1™ Website Printout, found at: www.ibe-technology.com/oratropin.htm [retrieved on Jan. 20, 2006].

Peppas, N. and P. Burl. "Surface, interfacial and molecular aspects of polymer bioadhesion on soft tissues," Journal of Controlled Release, 2:257-275 (1985).

Press Release: "OmegaH2O® clear shelf stable Omega-3, CoQ10 and other non polar compounds U.S. Appl. No. 12/383,244 approved in Europe and Notice of Allowance in U.S.," Published on Jun. 4, 2012 [online] Retrieved from:<URL:pr.com/press-release/417599 [4 pages].

Press Release: "VIRUN patent granted mucosal adhesive penetrating technology delivering naive compounds and peptides orally," Published on Mar. 23, 2011 [online] Retrieved from:<URL: pr.com/press-release/307987 [2 pages].

Press Release: "VIRUN® closes $2.1 million series—A funding to bolster innovation and world-wide expansion," Published on Aug. 2, 2012 [online] Retrieved from:<URL:pr.com/press-release/431579 [4 pages].

Ryan et al. "Immunomodulators and delivery systems for vaccination by mucosal routes" Trends in Biotechnology, 293-304 (2001).

Simoes et al., "Mechanisms of gene transfer mediated by lipoplexes associated with targeting ligands or pH-sensitive peptides," Gene Ther. (11):1798-1807 (1999).

Smart et al., "An in-vitro investigation of mucosa-adhesive materials for use in controlled drug delivery," J. Pharm. Pharmacol. 36:295-299 (1984).

Smart et al., "In vitro techiniques for measuring mucoadhesion," J. Pharm. Pharmacol. 34:70P (1982).

Tabor et al., " Surface forces and surface interactions" Journal of Colloid and Interface Science. 58(1):2-13 (1977).

Virun home Webpage found at www.virun.com [ accessed on Mar. 24, 2011], 59 pages.

Virun Improving Life Through Safe & Effective Oral Delivery found at: www.sldeshare.net/virun/virun-improving-life-through-safe-effective-oral-delivery [accessed on May 11, 2009], 15 pages.

Virun Intricate Science; found at www.slideshare.net/virun/virun-intricate-science [accessed May 25, 2011], 22 pages.

Vogelson. C., "Advances in drug delivery systems," Modern Drug Discovery. 4(4):59-50,52 (2001).

Wadell, C., "Nasal drug delivery—in vitro studies on factors influencing permeability and implications on absorption," Acta Universitatis Upsaliensis. Comprehensive Summaries of Uppsala Dissertations from the Faculty of Pharmacy 278. Upsala. ISBN 91-554-5449-6 pp. 1-55 (2002).

Wright, R., "Companies to watch—Nutraceuticals World," located at: www.nutraceuticalsworld.com/articles/2009/06/companies-to-watch, (2009) [accessed on Jun. 4, 2009], 7 pages.

Zaghloul et al., "Development, characterization and optimization of ibuprofen self-emulsifying drug delivery system applying face centered experimental design," International Journal of Pharmacy and Technology; 3(1):1674-1693 (2011).

International Search Report, issued Oct. 25, 2005, in connection with corresponding International Application No. PCT/US2005/021424, 4 pages.
Written Opinion, issued Oct. 25, 2005, in connection with corresponding International Application No. PCT/US2005/021424, 7 pages.
Internation Preliminary Report on Patentability, issued Dec. 20, 2006, in connection with corresponding International Application No. PCT/US2005/021424, 14 pages.
Examination Report, issued Dec. 13, 2007, in connection with corresponding European Patent Application No. 05762240.9, 7 pages.
Response to Examination Report, issued Dec. 13, 2007, in connection with corresponding European Patent Application No. 05762240.9, 9 pages.
Examination Report, issued Jul. 21, 2008, in connection with corresponding European Patent Application No. 05762240.9, 3 pages.
Office Action and translation, Issued Oct. 17, 2008, in connection with corresponding Chinese Patent Application No. 200580028061.8, 9 pages.
Examination Report, issued Dec. 3, 2008, in connection with corresponding Canadian Patent Application No. 2,578,709, 2 pages.
Response to Examination Report, issued Dec. 3, 2008, in connection with corresponding Canadian Patent Application No. 2,578,709, 12 pages.
Response to Examination Report, issued Jul. 21, 2008, in connection with corresponding European Patent Application No. 05762240.9, 8 pages.
Restriction Requirement, issued Jan. 30, 2009, in connection with U.S. Appl. No. 11/155,262, 14 pages.
Response and Instructions for Response to Office Action, issued Oct. 17, 2008, in connection with corresponding Chinese Patent Application No. 200580028061.8, 9 pages.
Office Action, issued Jun. 2, 2009, in connection with U.S. Appl. No. 11/155,262, 21 pages.
Notice of Allowance, issued Jul. 23, 2009, in connection with corresponding Canadian Patent Application No. 2,578,709, 2 pages.
Response to Office Action, issued Jun. 2, 2009, in connection with U.S. Appl. No. 11/155,262, 21 pages.
Office Action, Issued Mar. 1, 2010, in connection with corresponding Chinese Patent Application No. 200580028061.8, 11 pages.
Office Action, issued Mar. 18, 2010, in connection with U.S. Appl. No. 11/155,262, 11 pages.
Response to Office Action, issued Mar. 18, 2010, in connection with U.S. Appl. No. 11/155,262, 29 pages.

Examination Report, issued Sep. 13, 2010, in connection with corresponding Indian Patent Application No. 00458/DELNP/2007, 4 pages.
Response to Office Action, Issued Mar. 1, 2010, in connection with corresponding Chinese Patent Application No. 200580028061.8, 11 pages.
Notice of Allowance, issued Oct. 27, 2010, in connection with U.S. Appl. No. 11/155,262, 6 pages.
Office Action, issued Dec. 30, 2010, in connection with Chinese Application No. 200580028061.8, 6 pages.
Instructions for Response to the Office Action, issued Dec. 30, 2010, in connection with Chinese Application No. 200580028061.8, 21 pages.
Foreign Associate Communication, received Jun. 14, 2011, reporting results of a phone interview with Examiner dated Jun. 14, 2011 and Jun. 17, 2011, in connection with corresponding Chinese Application No. 200580028061.8, 4 pages.
Instructions for Response to Interview with Examiner, sent Jun. 22, 2011, in connection with Chinese Application No. 200580028061.8, 10 pages.
Foreign Associate Further Communication, received Jul. 1, 2011, in connection with corresponding Chinese Application No. 200580028061.8, 8 pages.
Further Instructions for Response to Interview with Examiner, sent Jul. 6, 2011, in connection with corresponding Chinese Application No. 200580028061.8, 3 pages.
Response to Examination Report, issued Jul. 6, 2010, in connection with Indian Patent Application No. 458/DELNP/2007, 24 pages.
Notice of Grant and translation, issued Sep. 5, 2011, in connection with Chinese Application No. 200580028061.8, 4 pages.
Restriction Requirement, issued Dec. 6, 2011, in connection with U.S. Appl. No. 12/930,978, 12 pages.
Response to Restriction Requirement, issued Dec. 6, 2011, in connection with U.S. Appl. No. 12/930,978, 7 pages.
Office Action, issued Mar. 1, 2012, in connection with U.S. Appl. No. 12/930,978, 6 pages.
Response to Office Action, issued Mar. 1, 2012, in connection with U.S. Appl. No. 12/930,978, 7 pages.
Notice of Allowance, issued Apr. 20, 2012, in connection with U.S. Appl. No. 12/930,978, 9 pages.
Decision to Grant, issued Jul. 12, 2012, in connection with corresponding European Patent Application No. 05762240.9, 1 page.

* cited by examiner

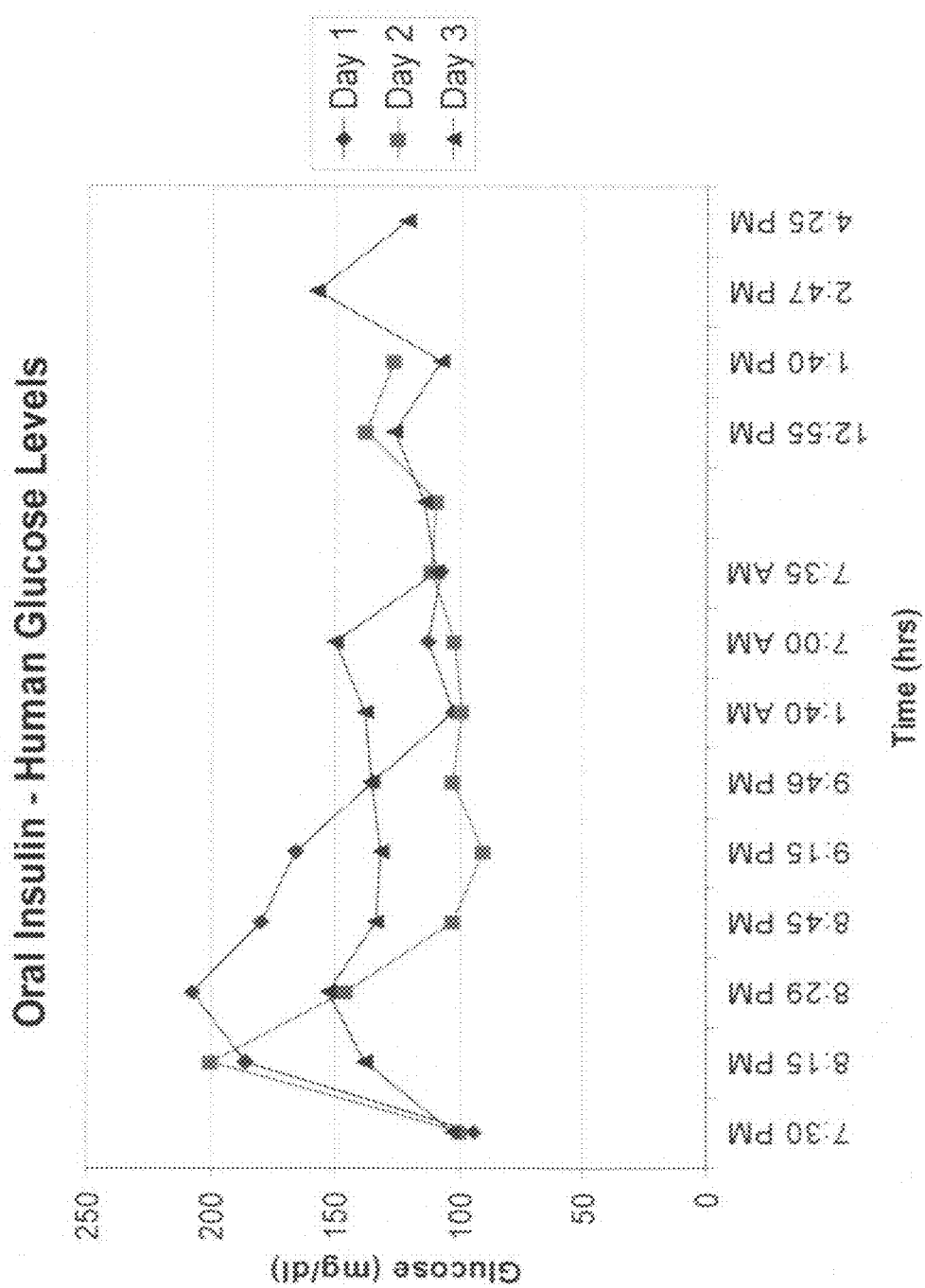

COMPOSITIONS FOR MUCOSAL DELIVERY OF AGENTS

RELATED APPLICATIONS

This application is a continuation of now allowed U.S. application Ser. No. 12/930,978, entitled "COMPOSITIONS FOR MUCOSAL DELIVERY OF AGENTS," to Bromley et al., filed Jan. 20, 2011 now U.S. Pat. No. 8,252,323, which is a continuation of U.S. application Ser. No. 11/155,262, now U.S. Pat. No. 7,906,140, issued Mar. 15, 2011, entitled "COMPOSITIONS FOR MUCOSAL DELIVERY OF AGENTS," to Bromley et al., filed Jun. 16, 2005, which claims priority under 35 U.S.C. §119(e) to U.S. Provisional Application Ser. No. 60/580,877, entitled "COMPOSITIONS FOR MUCOSAL DELIVERY OF AGENTS," to Bromley et al., filed Jun. 17, 2004. The subject matter of these applications is incorporated by reference herein.

This application is related to International PCT application No. PCT/US2005/021424, filed Jun. 16, 2005. The subject matter of PCT application No. PCT/US2005/021424 is incorporated by reference herein.

FIELD

Provided herein are pharmaceutical compositions for delivery of agents. Compositions formulated as emulsions for mucosal delivery are provided.

BACKGROUND

Numerous pharmaceutical substances are available for administration to animals, including humans, for a variety of purposes. These substances include, for example, therapeutic agents, such as drugs; dietary supplements, such as vitamins; prophylactic agents, such as antigens for use in vaccines; and diagnostic agents, such as labeled imaging agents. Administration of these substances can be via a number of routes including intramuscular, subcutaneous and oral administration. Intramuscular or subcutaneous administration of the substance suffers from disadvantages: relatively specialized skills are required to administer the pharmaceutical; large scale administration can be difficult to perform; it is expensive; and a number of side reactions can occur to the substance administered. Many antibiotics (i.e., tetracycline and penicillin), and hormones (i.e., progesterone and estrogen) can be administered successfully via the oral route.

There are, however, biologically active agents, for example certain dietary supplements, drugs, hormones and immunogens, whose efficacy is almost totally lost upon oral administration. Included among those agents that cannot be effectively orally administered are polypeptide agents, such as Calcitonin, Erythropoetin, Granulocyte Colony Stimulating Factor, Stem Cell Factor, Granulocyte Colony Stimulating Factor, LHRH analogues, Somatostatin, Insulin, Interferons, Plasminogen Activator Inhibitors and species of DNA and RNA. Oral delivery of certain protein and polypeptide drugs is complicated by the presence of proteolytic digestive enzymes in the stomach and intestines. Unprotected proteins, which are administered orally, are largely degraded by such enzymes before they are able to pass through the enteric wall and enter blood circulation. To some extent this effect can be overcome by the administration of extremely large doses of the pharmaceutical agent. This approach, however, is not economically feasible for many pharmaceutical agents and may result in undesired side effects.

Thus, there continues to be a need for the development of compositions and methods for convenient delivery of such substances to animals, including humans, efficiently. Accordingly, among the objectives herein, it is an objective to provide compositions and methods for convenient delivery of agents to be delivered to a subject.

SUMMARY

Provided herein are compositions and methods for formulation of the compositions for mucosal delivery and administration of agents to animals, including humans. Provided are compositions and methods for administering substances to animals, including humans, employing a carrier that facilitates entry of the substance to the mucosa in a non-specific manner.

The compositions provided herein are stable emulsions of oil in water or water in oil, wherein an agent to be delivered is dissolved in either the oil phase or the water phase. The emulsions are typically stabilized by surface active molecules in the emulsion. The surfactant molecules form various macro-molecular structures in an emulsion, such as micelles, inverse micelles, lipid bilayers (liposomes) and cubosomes. The exact macromolecular structure formed depends on the relative sizes of the hydrophilic and hydrophobic regions of the surface active molecule. The agent to be delivered can be distributed between the hydrophobic and hydrophilic phases of an oil-in-water or water-in-oil type emulsion, or can be present predominantly in one of the phases. In certain embodiments, the active agent in the emulsion is encapsulated in a delivery vehicle such as a micelle, a liposome or a cubosome or a mixture thereof.

The compositions provided have a mucoadhesive property whereby the composition, when administered either orally or nasally, adheres to and/or anchors to a subject's mucous membrane for a period of time sufficient to quantitatively deliver the agent to be delivered to the subject. The compositions contain a mucoadhesive substance that imparts the composition a property of adhering or anchoring to a mucosal membrane thereby effecting absorption of the agent through the mucosal membrane. Typically, the mucoadhesive protein is present in an amount sufficient to confer mucoadhesive property to the composition. Such mucosal absorption allows entry of the agent being delivered into the systemic circulation without first passing through the liver, and thus alleviates the loss of activity upon passage through the liver.

The mucoadhesive substances for use herein include, but are not limited to natural or synthetic proteins, polypeptides or fragments thereof that have the property of adhering or penetrating into a mucus membrane for a period of time sufficient to achieve quantitative delivery of an agent to be delivered. In certain embodiments, the compositions are designed for mucosal delivery of a therapeutically-effective amount of a biologically active agent to the subject. The mucoadhesive protein is generally dissolved in the water phase. In certain embodiments the mucoadhesive protein can be dissolved in the oil phase. The mucoadhesive protein is typically anchored to polar head groups of the delivery vehicles in the emulsion.

In certain embodiments, the compositions provided herein are formulated to contact the mucosal membrane from about 5-24 hours or even longer, in some embodiments about 5, 10, 12, 14, 16, 18, 20, 22 or up to 24 hours. In some embodiments, the compositions provided herein are formulated to contact the mucosal membrane from about 1 minute up to about 180, 120, 100, 60, 40, 30, 20, 10, 5, 4, 3, or 2 minutes. In certain embodiments, the compositions provided herein are formulated to adhere or penetrate into the mucosal membrane from about 5-24 hours or even longer, in some embodiments for about 5, 10, 12, 14, 16, 18, 20, 22 or up to 24 hours. In some embodiments, the compositions provided herein are formulated to adhere or penetrate into the mucosal membrane from about 1 minute up to about 180, 120, 100, 60, 40, 30, 20, 10, 5, 4, 3, or 2 minutes. In other embodiments, the compositions provided herein are formulated to adhere and penetrate into the mucosal membrane from about 5-24 hours or even longer, in some embodiments, for about 5, 10, 12, 14, 16, 18, 20, 22 or up to 24 hours. In some embodiments, the compositions provided herein are formulated to adhere and penetrate into the mucosal membrane from about 1 minute up to about 180, 120, 100, 60, 40, 30, 20, 10, 5, 4, 3, or 2 minutes. In certain embodiments, the compositions provided herein are formulated to adhere to the mucosal membrane from about 5-24 hours or even longer, in some embodiments for about 5, 10, 12, 14, 16, 18, 20, 22 or up to 24 hours. In some embodiments, the compositions provided herein are formulated to adhere to the mucosal membrane from about 1 minute up to about 180, 120, 100, 60, 40, 30, 20, 10, 5, 4, 3, or 2 minutes. In certain embodiments, the compositions provided herein are formulated to penetrate into the mucosal membrane from about 5-24 hours or even longer, in some embodiments for about 5, 10, 12, 14, 16, 18, 20, 22 or up to 24 hours. In some embodiments, the compositions are formulated to penetrate into the mucosal membrane from about 1 minute up to about 180, 120, 100, 60, 40, 30, 20, 10, 5, 4, 3, or 2 minutes.

Compositions provided herein can have a wide range of viscosities, typically in a range that assists retention of the composition on a mucosal surface. Generally, the viscosity ranges from an oil like viscosity, honey like viscosity, ketchup like viscosity, chocolate syrup like viscosity to peanut butter like or butter like viscosity. The viscosity of the compositions can be measured by methods known to those of skill in the art, including measurement by using a viscometer such as Brookfield LVDV-I+ viscometer and T spindles with a heliopath adapter. The viscosity of the compositions provided can range from 10 cps, 100 cps, 1000 cps, 10,000 cps, 100,000 cps, or 200,000 cps up to more than 500,000 cps at 72° F.

The compositions provided herein are formulated to remain stable over a relatively long period of time. For example, the compositions provided herein are stored at room temperature, and remain stable for more than 1 day, 1 week, 1 month and in certain embodiments up to more than 1 year. In certain embodiments, the compositions provided herein are delivered to the oral mucosa or nasal mucosa. In certain embodiments, the compositions are delivered to intestinal mucosa.

Also provided herein are methods of using the compositions. In certain embodiments, the methods provided herein are used for delivery of one or more agents to be delivered including, but not limited to biologically active agent such as minerals, vitamins, synthetic or natural compounds, pharmaceutical drugs, nutritional supplements, herbs, hormones, or the like, which when introduced into the body cause a desired biological response, such as altering body function at the cellular, tissue or organ level and/or altering cosmetic appearance. In certain embodiments, the methods are used to deliver a biological agent, wherein the agent is a drug or other pharmaceutical ingredient which suffers significant loss of activity in the lumen of the gastrointestinal tract or in the tissues of the gastrointestinal tract during absorption process or upon passage through the liver after absorption in the intestinal tract.

In certain embodiments, the methods provided herein are useful for delivery of therapeutics used in treatment of various disorders, such as neural disorders, respiratory disorders, immune system disorders, muscular disorders, reproductive disorders, gastrointestinal disorders, pulmonary disorders, digestive disorders, metabolic disorders, cardiovascular disorders, renal disorders, proliferative disorders, cancerous diseases and inflammation. The therapeutics delivered using the methods provided herein include, but are not limited to anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides, polysaccharides, and nutritional supplements including herbal supplements. In certain embodiments, the methods are for delivery of dietary supplements, including but not limited to vitamins, minerals, hormones and antioxidants.

Methods of making the compositions are also provided. The compositions provided herein are prepared by mixing an oil phase with a water phase at a mixing speed that does not degrade and disintegrate any of the active ingredients of the composition. The mixing speed can range from about 100 RPM up to about 60,000 RPM. The temperature, pressure, and pH conditions during the mixing step are maintained so that all the components in the oil and water phase are dissolved and the active ingredients are not degraded in any way. A suitable temperature during the mixing step can be determined empirically for a particular combination of ingredients in the composition. Typically, the temperature is maintained at about 100-120° F., in some embodiments at about 115° F. The pressure during the mixing is maintained at about 25 PSI (pounds per square inch). The pH during the mixing step is a function of the particular mucoadhesive protein and the agent to be delivered in the composition. Typically the pH is basic or neutral.

The compositions can be prepared by mixing the water phase with an oil phase to form a water-in-oil emulsion. The agent to be delivered can be dissolved in the oil phase or in the water phase. Typically, a mucoadhesive protein is present in the water phase in an amount sufficient to confer mucoadhesive property to the composition. In certain embodiments, the compositions adhere or anchor to the mucosal surface for an amount of time sufficient to achieve quantitative delivery of the agent to be delivered. The compositions provided herein can also include one or more surface active agent, and one or more additives, such as a polymer, a cosolvent, an antioxidant, an antiseptic, a buffering agent, a chelating agent, a colorant, a flavorant, an odorant, an osmotic modifier, a preservative, a solubilizer, a tonicifier, a trace element, a viscomodulator, or a mixture thereof. Such additives are known to those of skill in the art and are described herein.

Articles of manufacture, containing packaging material for a composition for mucosal delivery and administration, a composition for mucosal delivery of biologically active agents and a label that indicates that the composition is for achieving a desired biological response, such as altering body function or altering cosmetic appearance. In certain embodiments, the articles of manufacture, contain a packaging material, a composition for mucosal delivery of biologically active agents and a label that indicates that the composition is useful for treatment, prevention or amelioration of one or more symptoms of diseases or disorders contemplated herein.

BRIEF DESCRIPTION OF THE DRAWINGS

FIG. 1 indicates variance in blood glucose levels in a human after administration of a composition provided herein for 3 consecutive days.

DETAILED DESCRIPTION

A. Definitions

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, mucosa or mucus membrane refers to epithelial tissue that lines the internal cavities of the body, such as oral cavity, the respiratory tract, the gastrointestinal tract, the lungs, and the genitalia. The mucous membrane or mucosa protects the body from foreign matter and pathogens and is permeable to a certain extent. Agents delivered through the mucosa enter circulation in hours or for as long as about 24 hours after administration (i.e. about 4-24 hours for insulin). Entry of the agent to be delivered is a function of the drug and the mucoadhesive protein selected. The compositions provided herein exploit the limited permeability of the mucosa and generally are formulated for delivery through the oral and nasal mucosa, although they can be used formulated for delivery through any mucosal surface, including the mouth, nasal passages, gastrointestinal tract, lungs and the mucosal layer of other tissues and organs.

As used herein, mucosal delivery refers to delivery of an agent in which the agent is introduced to the body across a mucous membrane which allows for the avoidance of the gastrointestinal tract and first pass liver metabolism and consequently allows the agent to directly enter into circulation. This can include passage through the gastrointestinal tract as by oral ingestion, but refers to delivery through the muscosa of such locus.

As used herein, "contact to mucosal surface" refers to contact of the composition into the mucosal surface for an amount of time sufficient to achieve quantitative delivery of the composition. Contact of the composition can result in adhesion and/or penetration of the composition into the mucosal surface. The compositions provided herein can contact the mucosal surface from 30 seconds up to about 24 hours. In certain embodiments, the composition contacts the mucosal surface for about 5, 10, 12, 14, 16, 18, 20, 22 or up to 24 hours. In some embodiments, the compositions provided herein contact the mucosal membrane from about 1 minute up to about 180, 120, 100, 60, 40, 30, 20, 10, 5, 4, 3, or 2 minutes.

As used herein, mucoadhesive property refers to a property whereby a natural or synthetic substance, such as a protein, when applied to a mucosal epithelium adheres to or penetrates a subject's mucous membrane for a period of time sufficient to quantitatively deliver a composition provided herein to the subject. The composition can anchor in and/or penetrate into a mucosal surface. Adhesion of mucoadhesives to a mucous membrane occurs generally, although not necessarily or exclusively, via secondary chemical bonds, such as hydrogen bonding and Van der Waal forces (Tabor et al., 1977 J. Colloid Interface Sci. 58:2 and Good 1977 J. Colloid Interface Sci. 59:398). Parameters, such as mechanical binding to mucous membrane per se or the degree of biological effect of an agent delivered can be used as a measurement parameter to detect and quantitate mucoadhesion.

As used herein, mucoadhesive compositions are viscous aqueous solutions. Their mucoadhesive (or penetrative) properties can be assessed by comparison to a control composition that does not contain the mucoadhesive protein(s) added to the mucoadhesvie composition. At similar viscosities, the emulsion prepared with a mucoadhesive protein or protein binds to a mucosal surface more strongly (i.e. more is bound or penetrates or is delivered) compared to a control emulsion without the mucoadhesive protein or protein(s). Such increase in delivery or binding or penetration is at least about 10%, 20%, 30%, 40%, 50%, 60%, 70%, 80%, 90% or 100% greater mucosal binding than a control emulsion.

As used herein, mucoadhesive proteins refer to any natural or synthetic proteins, polypeptides or fragments thereof that possess the mucoadhesive property. Non-limiting examples of mucoadhesive proteins include mucin proteins and transferrins. In certain embodiments, the protein for use in the compositions and methods provided herein is lactoferrin. In certain embodiments, the mucoadhesive protein present in a composition provided herein is in an amount sufficient to confer a mucoadhesive property to the composition.

As used herein, "biologically compatible substance" refers to a substance which when administered to a subject, such as a human, does not produce undesired or toxic effects.

As used herein, "an agent," is any substance that can be delivered via compositions provided herein to a mucosal surface of a subject.

As used herein, "a biologically active agent," "a biological agent," or "an agent," is any substance which when introduced into the body causes a desired biological response, such as altering body function at the cellular, tissue or organ level and/or altering cosmetic appearance. Such substance can be any synthetic or natural element or compound, protein, cell, or tissue including a pharmaceutical, drug, therapeutic, nutritional supplement, herb, hormone, or the like, or any combinations thereof. The terms also encompass pharmaceutically acceptable, pharmacologically active derivatives of those active agents specifically mentioned herein, including, but not limited to, salts, esters, amides, prodrugs, active metabolites, isomers, fragments, analogs, and the like. When the terms "biologically active agent," "biological agent" and "agent" are used, then, or when a particular active agent is specifically identified, it is intended to include the active agent per se as well as pharmaceutically acceptable, pharmacologically active salts, esters, amides, prodrugs, active metabolites, isomers, fragments and analogs.

As used herein, a subject is defined as an animal, including a mammal, typically a human.

As used herein, quantitative delivery refers to delivery of a substantial portion of the amount administered, and is typically, greater than 50%, 60%, 70%, 80%, 85%, 90%, 91%, 92%, 93%, 94%, 95%, 96%, 97%, 98%, or 99%.

As used herein, therapeutically effective amount refers to an amount of the active agent for a desired therapeutic, prophylactic, or other biological effect or response when a composition is administered to a subject in a single dosage form. The particular amount of active agent in a dosage will vary widely according to conditions such as the nature of the active agent, the nature of the condition being treated, the age and size of the subject.

As used herein, an emulsion is defined as a colloidal dispersion of two immiscible liquids, such as oil and water, in the form of droplets. The emulsions are generally stabilized by an interfacial film of surface active agents or surfactant molecules, such as polysorbate-80 and the stability of an emulsion can be determined by well known routine methods.

As used herein, surfactants (or "surface-active agents") are chemical or naturally occurring entities which, when dissolved in an aqueous solution, reduce the surface tension of the solution or the interfacial tension between the aqueous phase and the oil phase, to form a stable oil in water or water in oil emulsion. The surfactant molecules are amphiphilic and contain hydrophilic head groups and hydrophobic tails. The surfactant molecules form various macro-molecular structures in an emulsion, such as micelles, inverse micelles, lipid bilayers (liposomes) and cubosomes. The exact macromolecular structure which is formed depends on the relative sizes of the hydrophilic and hydrophobic regions of the surface active molecules.

Micelle formation is favored when the cross sectional area of the hydrophilic region of the surface active molecule is greater than that of the hydrophobic part of the molecule. For example, sodium palmitate contains a hydrocarbon chain (the hydrophobic portion of the molecule) and an ionic base (the hydrophilic portion of the molecule), and acts as an emulsifying agent that binds water and oil phases. That is, it allows oil and water to be broken into tiny droplets suspended or dispersed in water as spherical micelles, wherein the hydrophilic head groups arrange at the periphery of the sphere and hydrophobic tails are at the center.

When the cross sectional area of the hydrophobic region of the molecule is greater than that of the hydrophilic part of the molecule, the formation of hexagonal phase structures, sometimes referred to as an inverse micelle is favored, e.g., dimyristoyl-phosphatidylethanolamine (DMPE).

For surface active molecules in which the cross sectional area of the hydrophilic region of the molecule is slightly less than, or equal to, that of the hydrophobic part of the molecule, such as many phospholipids (which are amphipathic type of lipids that contain phosphate, that is, molecules containing one phosphate, a glycerol and one or more fatty acids), the formation of bilayers is favored, e.g., dipalmitoylphosphatidylcholine (DPPC). These bilayers are two dimensional sheets in which all of the hydrophobic portions, e.g., acyl side chains, are shielded from interaction with water except those at the ends of the sheet. An energetically unfavorable interaction of the acyl chains with water results in the folding of the bilayers to form three-dimensional vesicles. These vesicles are referred to as "liposomes." Liposomes may be formed as a single bilayer enclosing a single aqueous space (small unilamellar vesicles; SUVS) or may be composed of concentric bilayers with many aqueous spaces alternating with the bilayers (multilamellar vesicles; MLVS). Liposomes can be used to encapsulate both hydrophobic and hydrophilic active agents. Hydrophobic active agents are typically partitioned within the bilayers whereas hydrophilic active agents are typically trapped within the aqueous compartments. The advantages of using liposomes as a carrier/encapsulation system is that they are stable and can protect the active agents from degradation, e.g., by oxygen, digestive enzymes, etc.

As used herein, a "delivery vehicle" refers to macro-molecular structures in an emulsion, such as micelles, inverse micelles, lipid bilayers (liposomes) and cubosomes or a mixture thereof.

As used herein, "protein is associated with a delivery vehicle" means the mucoadhesive protein is associated with a delivery vehicle via chemical or physical interaction, such as hydrogen bond or van der waal's forces. The mucoadhesive protein, such as lactoferrin can be for example, associated with the polar head groups of the delivery vehicles, such as micelles via a chemical interaction, such as a hydrogen bond.

As used herein, "agent is associated with a delivery vehicle" means the delivery vehicle contains the agent to be delivered. The agent can be for example, encapsulated in a micelle or encapsulated in the liposome bilayers.

As used herein, viscosity refers to a physical property of fluids that determines the internal resistance to shear forces and is expressed in centipoise (cp).

The oil phase in the emulsion provided herein can be any nontoxic oil, biocompatible oil, which includes, but is not limited to mono-, di- and triglycerides, fatty acids and their esters, ethers and esters of propylene glycol or other polyols. The fatty acids and esters (used as such or where they form part of a glyceride) can be short chain, medium chain or long chain. As used herein, medium chain represents a hydrocarbon chain of $C_8$ to $C_{12}$ and short chain is a hydrocarbon chain of less than $C_8$ and long chain means a hydrocarbon chain of more than $C_{12}$. The water phase in the emulsion can be water, aqueous solutions, alcohols, alcohol solutions, and the like.

As used herein, the stability of a composition provided herein refers to the length of time at a given temperature that greater than 10%, 20%, 30%, 40%, 50%, 60%, 70%, 80%, 85%, 90%, 91%, 92%, 93%, 94%, 95%, 96%, 97%, 98% or 99% of the initial amount of the agent to be delivered, e.g., insulin, is present in the composition. Thus, for example, a composition that is stable for 30 days at 25° C. would have greater than 10%, 20%, 30%, 40%, 50%, 60%, 70%, 80%, 85%, 90% 91%, 92%, 93%, 94%, 95%, 96%, 97%, 98% or 99% of the initial amount of active ingredient present in the composition at 30 days following storage at 25° C.

As used herein, pharmaceutically acceptable derivatives of a compound include salts, esters, enol ethers, enol esters, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Pharmaceutically acceptable solvates and hydrates are complexes of a compound with one or more solvent or water molecule, in certain embodiments 1 to about 100, in other embodiments 1 to about 10, in further embodiments one to about 2, 3 or 4, solvent or water molecules.

As used herein, treatment means any manner in which one or more of the symptoms of a condition, disorder or disease are ameliorated or otherwise beneficially altered. Treatment also encompasses any pharmaceutical use of the compositions herein, such as use for treating diabetes.

As used herein, amelioration of the symptoms of a particular disorder by administration of a particular pharmaceutical composition refers to any lessening, whether permanent or temporary, lasting or transient that can be attributed to or associated with administration of the composition.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

It is to be understood that the compounds for use in the compositions and methods provided herein can contain chiral centers. Such chiral centers may be of either the (R) or (S) configuration, or may be a mixture thereof. Thus, the compounds for use in the compositions provided herein may be enantiomerically pure, or be stereoisomeric or diastereomeric mixtures. It is to be understood that the chiral centers of the compounds provided herein may undergo epimerization in vivo. Thus, one of skill in the art will recognize that administration of a compound in its (R) form is equivalent, for compounds that undergo epimerization in vivo, to administration of the compound in its (S) form.

B. Compositions

1. Mucosal Delivery

Provided herein are compositions and methods for mucosal delivery of agents, particularly agents that are normally difficult to administer or ineffective when administered orally or nasally. The compositions provided herein contain one or more mucoadhesive proteins that impart a mucoadhesive property to the composition. Contacting a mucosal surface in a subject with a composition results in delivery of composition, including active and inactive components into circulation. The compositions provided herein are for delivery of agents, such as biologically active agents, through mucosa, such as oral, nasal or intestinal mucosa.

Mucosal delivery systems offer benefits over other methods of delivery. For example, absorption through the mucous membrane leads the delivered active agent directly into the circulatory system. This allows such agents, in certain embodiments, to bypass the gastrointestinal tract as well as first pass liver metabolism. Secondly, the biologically active agents such as drugs directly enter the circulatory system, which allows the therapeutic to be rapidly transported to the site of need. The faster the drug reaches its target area, the faster it can begin to elicit its desired effect. Further, the avoidance of the gastrointestinal tract and first pass metabolism means that much less of the drug can be administered to achieve the same effect, allowing for lower dosages to be administered and fewer side effects.

Some common modes of mucosal administration include oral and nasal administrations. Those of skill in the art are familiar with a variety of modes of administration (see, e.g., Almeida et al. *Journal of Drug Targeting* 3, 456-467 (1996), which provides a review of mucosal administration of vaccines in general, and nasal administration of vaccines in particular). The compositions upon contacting with the mucosal surface, adhere thereto or penetrate through the mucosal surface, for an amount of time sufficient to achieve quantitative delivery of the composition, including, but not limited to less than 1 minute up to more than 3 hours. Various parameters known in the art can be used for measurement of mucoadhesion. Such parameters include, but are not limited to, mechanical binding to mucous membrane per se or the degree of biological effect of an agent delivered. The compositions are formulated to adhere to or penetrate into the mucosal surface for about 1, 2, 3, 4, 5, 10, 15, 20, 25, 30, 35, 40, 50, 60, 70, 80, 90, 100, 120, 150 minutes or up to more than 180 minutes after being delivered to the mucosa. In certain embodiments, compositions are formulated to adhere to or penetrate into the mucosal surface for about 1, 2, 3, 4, 5, 6, 7, 8, 9, 10, 12, 14, 16, 18, 20, 22, 24 or more hours.

Mucosal delivery of agents can be effected either in the absence or in the presence of a carrier. Mucosal administration in the presence of a carrier serves various purposes, such as controlled release of biologically active molecules, targeting of biologically active molecules to specific tissues, and facilitating penetration into the mucosal layer.

2. Compositions

The compositions provided herein, which provide mucosal delivery of agents, are formulated as emulsions, including oil in water and water in oil emulsions. In preparing the compositions, an agent to be delivered is dissolved either in the oil phase or the water phase prior to forming an emulsion. The compositions optionally include additional ingredients, such as surface active agents for stabilizing the emulsions.

Compositions provided herein can have a wide range of viscosities, typically ranging from about 10 cps; 50 cps; 100 cps; 300 cps; 500 cps; 750 cps; 1000 cps; 3000 cps; 6000 cps; 8000 cps; 10,000 cps; 20,000 cps; 30,000 cps; 40,000 cps; 50,000 cps; 60,000 cps; 70,000 cps; 80,000 cps; 90,000 cps; 100,000 cps; 150,000 cps; 200,000 cps; 130,000 cps; 250,000 cps; or 280,000 cps up to more than 500,000 cps at 72° F. The viscosity of the compositions can be measured by methods known to those of skill in the art, including measurement by using a viscometer such as Brookfield LVDV-I+ viscometer and T spindles with a heliopath adapter.

In the compositions provided herein, oil phase, aqueous phase and emulsifier can be used in a wide range of ratios to make the emulsions. The oil-in-water emulsions contain at least 25% of water by weight, in one embodiment between 30% and 80% and in another embodiment between 40% and 95%. The oil phase in the oil in water emulsions is at least 1%, 2%, 3%, 4%, 5%, 6%, 7%, 8%, 9%, 10%, 15%, 20%, 25%, 30% or more by weight of the emulsion. The emulsifier or surfactant in the emulsions is at least 0.5%, 1%, 2%, 3%, 4%, 5%, 6%, 7%, 8%, 9%, 10%, 15%, 20%, or 25% by weight of the emulsion.

The water-in-oil emulsions contain at least 25% of oil by weight, in one embodiment between 30% and 80% and in another embodiment between 40% and 95% of oil by weight.

The water phase in the water in oil emulsions is at least 1%, 2%, 3%, 4%, 5%, 6%, 7%, 8%, 9%, 10%, 15%, 20%, 25%, 30% or more by weight of the emulsion. The emulsifier or surfactant in the emulsions is at least 0.5%, 1%, 2%, 3%, 4%, 5%, 6%, 7%, 8%, 9%, 10%, 15%, 20%, or 25% by weight of the emulsion.

The compositions provided herein also can include one or more other additives, such as a polymer, a cosolvent, an antioxidant, an antiseptic, a buffering agent, a chelating agent, a colorant, a flavorant, an odorant, an osmotic modifier, a preservative, a solubilizer, a tonicifier, a trace element, a viscomodulator and a mixture thereof. Such additional additives can be present in the oil phase, the aqueous phase, or both.

a. Mucoadhesive Proteins

The compositions contain one or more mucoadhesive proteins. The mucoadhesive proteins for use in the compositions and methods provided herein include any protein that imparts a mucoadhesive property to the composition whereby the composition when administered to a subject's mucosal surface, such as oral or nasal mucosa, adheres or penetrates into the mucosal epithelium of the subject for a period of time sufficient to achieve quantitative delivery of an agent to be delivered. In certain embodiments, the compositions adhere to or penetrate through the mucosal membrane for a period of time sufficient to locally deliver a therapeutically-effective amount of an active agent in the composition. Adhesion of mucoadhesive protein to the mucous membrane occurs primarily via secondary chemical bonds, such as hydrogen bonding and Van der Waal forces.

Any mucoadhesive protein that is biologically compatible can be employed. Mucoadhesive proteins for use herein include, but are not limited to natural or synthetic proteins, polypeptides or fragments thereof that possess the mucoadhesive property. Mucoadhesive proteins can be screened for their ability to be used as mucoadhesives for mucosal delivery of compositions provided herein according to the methodology described in Smart et al., 1982 *J. Pharm. Pharmacol.* 34:70 P and Smart et al., 1984 *J. Pharm. Pharmacol.* 36:295. The methodology involves estimating values of adhesive strength between the mucoadhesive protein and the mucous membrane.

In certain embodiments, the mucoadhesive proteins are selected from a family of mucin proteins and transferrins. In certain embodiments, the mucoadhesive protein is from the transferrin family and is selected from bovine lactoferrin, human lactoferrin, lactoferrin binding proteins, recombinant human lactoferrin, lactoferricin, lactoferricin b, transferrin binding proteins, bovine transferrin, ovotransferrin, neutrophil granules, apo-lactoferrin and lanthanide-lactoferrin. In certain embodiments, the mucoadhesive proteins are selected from among lactoferrin, lactoferrin binding proteins, recombinant lactoferrin, lactoferricin, lactoferricin b, transferrin binding proteins, transferrin, ovotransferrin, neutrophil granules, apo-lactoferrin, immunoglobulin, albumin and lanthanide-lactoferrin. In certain embodiments, the mucoadhesive protein is selected from albumin, immunoglobulin and lactoferrin.

In certain embodiments, the mucoadhesive protein for use in the compositions and methods provided herein is lactoferrin. In certain embodiments, the compositions contain one, two or three mucoadhesive proteins. In certain embodiments, the compositions contain one mucoadhesive protein. In certain embodiments, the mucoadhesive protein in the compositions provided herein is present in an amount sufficient to confer a mucoadhesive property to the composition.

The mucoadhesive proteins can associate with the delivery vehicle via chemical or physical interaction. For example, the mucoadhesive protein can be hydrogen bonded with polar head groups of the micelles or the liposomes or other vehicles that are present in the emulsion in the compositions provided herein. Such compositions when administered either orally or nasally, to a subject in need thereof, adhere to or penetrate through the mucosal membrane via chemical or physical bond, such as secondary chemical bonds, including hydrogen bonding and Van der Waal forces, thereby providing sustained or prolonged coating of the composition on the epithelium of the oral cavity or nasal cavity depending on the mode of administration. The sustained coating of the composition allows for increased contact time between the composition and the epithelial layer, which in turn results in enhanced absorption of the active agent in to the mucosal layer.

The amount of mucoadhesive protein in the compositions provided herein, is an amount that results in quantitative delivery of an agent formulated therewith. The amount to be added can vary depending upon the agent delivered and other components of a composition, but it can be determined empirically by formulating compositions and testing them for delivery using any suitable assay known to those of skill in the art or as described herein.

Typically, the mucoadhesive protein is present at a concentration of about 0.05% by weight up to about 80%, generally 0.1, 0.2, 0.3, 0.4, 0.5, 1, 2, 3, 4, 5, 6, 7, 8, 9, 10, 15, 20, 25, 30, or 40% by weight up to about 50% by weight, of the total weight of the composition. In other embodiments, the mucoadhesive protein is present at a concentration of about 0.1% by weight up to about 30% by weight of the total weight of the composition. In other embodiments, the mucoadhesive protein is present at a concentration of about 0.1% by weight up to about 20% by weight of the total weight of the composition. In other embodiments, the mucoadhesive protein is present at a concentration of about 0.05% by weight up to about 15% by weight of the total weight of the composition. In other embodiments, the mucoadhesive protein is present at a concentration of about 0.05% by weight up to about 12% by weight of the total weight of the composition. In other embodiments, the mucoadhesive protein is present at a concentration of about 0.05% by weight up to about 10% by weight of the total weight of the composition. In other embodiments, the mucoadhesive protein is present at a concentration of about 0.05% by weight up to about 8% by weight of the total weight of the composition. In other embodiments, the mucoadhesive protein is present at a concentration of about 0.05% by weight up to about 5% by weight of the total weight of the composition. In other embodiments, the mucoadhesive protein is present at a concentration of about 8% by weight up to about 10% by weight of the total weight of the composition. In other embodiments, the mucoadhesive protein is present at a concentration of about 9% by weight up to about 10% by weight of the total weight of the composition. In other embodiments, the mucoadhesive protein is present at a concentration of about 15% by weight of the total weight of the composition. In other embodiments, the mucoadhesive protein is present at a concentration of about 12% by weight of the total weight of the composition. In other embodiments, the mucoadhesive protein is present at a concentration of about 10% by weight of the total weight of the composition. In other embodiments, the mucoadhesive protein is present at a concentration of about 9.5% by weight of the total weight of the composition. In other embodiments, the mucoadhesive protein is present at a concentration of about 9% by weight of the total weight of the composition. In other embodiments, the mucoadhesive protein is present at a concentration of about 8% by weight of the total weight of the composition. In other embodiments, the mucoadhesive protein is present at a concentration of about 6% by weight of the total weight of the composition. In other embodiments, the mucoadhesive protein is present at a concentration of about 4% by weight of the total weight of the composition. In other embodiments, the mucoadhesive protein is present at a concentration of about 2% by weight of the total weight of the composition. In other embodiments, the mucoadhesive protein is present at a concentration of about 1% by weight of the total weight of the composition. In other embodiments, the mucoadhesive protein is present at a concentration of about 0.8% by weight of the total weight of the composition. In other embodiments, the mucoadhesive protein is present at a concentration of about 0.6% by weight of the total weight of the composition. In other embodiments, the mucoadhesive protein is present at a concentration of about 0.4% by weight of the total weight of the composition. In other embodiments, the mucoadhesive protein is present at a concentration of about 0.1% by weight of the total weight of the composition. In other embodiments, the mucoadhesive protein is present at a concentration of about 0.05% by weight of the total weight of the composition.

b. Oils

The oils for use in the compositions include any oil obtained from a natural or synthetic source that is suitable for consumption by a subject. Oils suitable for administration to subjects, including humans, are known. Any such oil can be used. The oil can be of vegetable or animal origin. The oil phase also can be synthetic or semisynthetic oils that are nontoxic to a subject. Exemplary of oils for use herein include, but are not limited to mono-, di- and triglycerides, fatty acids, such as oleic, linoleic, palmitic, stearic, conjugated forms thereof and their esters, ethers and esters of propylene glycol or other polyols. In certain embodiments, the oils are short, medium or long chain triglycerides. In certain embodiments, the oils are medium chain triglycerides (MCTs). In certain embodiments, the MCT is tricaprylic triglyceride ester (also known as Neobee® M5). Exemplary sources for oils contemplated herein include, but are not limited to All Spice, Almond, Anise, Apple, Apricot, Avocado, Basil, Bayberry, Benzoin, Bergamot, Borage Seed, Cajeput, Calendula, Canola, Carnation, Carrot seed, Cassia bark, Castor, Cayenne, Cedarwood, Chamomile, Cinnamon, Citronella, Conjugated Linolenic Acid, Clary sage, Clove bud, Coconut, Cod Liver, Corn, Cranberry, Cypress, Evening Primrose, Eucalyptus, Evergreen, Fir, Fish 18:12, Flax Seed, Frangipani, Frankincense, Freesia, Gardenia, Ginger, Grape Seed, Grapefruit, Heather, Honeysuckle, Hyacinth, Jasmine, Jojoba, Juniper berry, Lavender, Lecithin, Lemon, Lemon balm, Lemon, verbena, Lemongrass, Lilac, Lily of the valley, Lime, Magnolia, MCT, Menthol, Mulberry, Musk, Myrrh Oat, Olive, Orange, Oregano, Palm, Patchouli, Peach, Pennyroyal, Peppermint, Petitgrain, Pine, Pumpkin Seed, Rice Bran, Rose, Rosemary, Rosewood, Safflower, Sage, Salmon, Sandalwood, Sesame, Shark Liver, Soy Bean, Spearmint, Squalene, Strawberry, Sunflower, Tangerine, Tea tree, Thuja (Cedar leaf), Thyme, Tuna, Vanilla, Vitamin E, Wheat Germ, Wintergreen and Ylang ylang. In certain embodiments, the oil phase contains oat oil and tri caprylic triglyceride ester (also known as Neobee® M5).

The oil is present in an amount sufficient to dissolve the oil soluble ingredients in the composition. The amount generally is a function of the locus of administration, the agent to be administered and other such parameters and can be empirically determined. For example, in some embodiments, the oil is present at a concentration of about 1%, 2%, 3%, 4%, 5%, 10%, 20%, 25%, 30%, 35%, 40%, 45%, 50%, 55%, 60%, 65%, 70%, 75%, 80%, 85%, 90%, 95% or more by weight. Thus, in certain embodiments, the oil is present at about 3, 4, or 5% by weight up to about 90% by weight of the total weight of the composition. In other embodiments, the oil is present at a concentration of about 3, 4, or 5% by weight up to about 85% by weight of the total weight of the composition. In other embodiments, the oil is present at a concentration of about 5% by weight up to about 70% by weight of the total weight of the composition. In other embodiments, the oil is present at a concentration of about 5% by weight up to about 50% by weight of the total weight of the composition. In other embodiments, the oil is present at a concentration of about 5% by weight up to about 45% by weight of the total weight of the composition. In other embodiments, the oil is present at a concentration of about 5% by weight up to about 40% by weight of the total weight of the composition. In other embodiments, the oil is present at a concentration of about 5% by weight up to about 35% by weight of the total weight of the composition. In other embodiments, the oil is present at a concentration of about 5% by weight up to about 30% by weight of the total weight of the composition. In other embodiments, the oil is present at a concentration of about 5% by weight up to about 20% by weight of the total weight of the composition. In other embodiments, the oil is present at a concentration of about 45% by weight of the total weight of the composition. In other embodiments, the oil is present at a concentration of about 40% by weight of the total weight of the composition. In other embodiments, the oil is present at a concentration of about 35% by weight of the total weight of the composition. In other embodiments, the oil is present at a concentration of about 30% by weight of the total weight of the composition. In other embodiments, the oil is present at a concentration of about 20% by weight of the total weight of the composition. In other embodiments, the oil is present at a concentration of about 10% by weight of the total weight of the composition. In other embodiments, the oil is present at a concentration of about 7% by weight of the total weight of the composition. In other embodiments, the oil is present at a concentration of about 5% by weight of the total weight of the composition.

c. Surface Active Agents

The compositions provided herein can contain one or more surface active agents that are added in an amount sufficient to form a stable emulsion. The appropriate amount of surface active agent is a function of the agent for delivery and other components present in the emulsion, since some agents can have self-emulsifying properties and other agents and components affect surface tension.

The surface active agents for use herein are substances which, when dissolved in an aqueous solution, reduce the surface tension of the solution or the interfacial tension between the aqueous phase and the oil phase, to form a stable oil in water or water in oil emulsion. The surfactant molecules are amphiphilic and contain hydrophilic head groups and hydrophobic tails. The surfactant molecules form various macro-molecular structures in an emulsion, such as micelles, inverse micelles, lipid bilayers (liposomes) and cubosomes. The exact macromolecular structure which is formed depends on the relative sizes of the hydrophilic and hydrophobic regions of the surface active molecule. In certain embodiments, the surface active agent is selected from sodium lauryl sulfate; sorbitan laurate, sorbitan palmitate, sorbitan stearate (available under the tradename Span® 20, 40, 60 etc.); polysorbates such as polyoxyethylene (20) sorbitan monolaurate, polyoxyethylene (20) sorbitan monopalmitate, polyoxyethylene (20) sorbitan monostearate (available under the tradename TWEENS® 20, 40, 60 etc.); benzalkonium chloride, mixed chain phospholipids, cationic lipids, oligolipids, phospholipids, carnitines, sphingosines, sphingomyelins, ceramides, glycolipids, lipoproteins, apoproteins, amphiphilic proteins, amphiphilic peptides, amphiphilic synthetic polymers, and combinations thereof. Other exemplary surface active agents for use herein include, but are not limited to:

i) Natural lipids, i.e. Cholesterol, Sphingosine and Derivatives, Gangliosides, Sphingosine derivatives (Soy Bean), Phytosphingosine and derivatives (Yeast), Choline (Phosphatidylcholine), Ethanolamine (Phosphatidylethanolamine), Glycerol (Phosphatidyl-DL-glycerol), Inositol (Phosphatidylinositol), Serine (Phosphatidylserine (Sodium Salt)), Cardiolipin, Phosphatidic Acid, Egg Derived, Lyso (Mono Acyl) Derivatives (Lysophosphatides), Hydrogenated Phospholipids, Lipid Tissue Extracts, ii) Synthetic lipids, i.e. Asymmetric Fatty Acid, Symmetric Fatty Acid—Saturated Series, Symmetric Fatty Acid—Unsaturated Series, Acyl Coenzyme A (Acetoyl Coenzyme A, Butanoyl Coenzyme A, Crotanoyl Coenzyme A, Hexanoyl Coenzyme A, Octanoyl Coenzyme A, Decanoyl Coenzyme A, Lauroyl Coenzyme A, Myristoyl Coenzyme A, Palmitoyl Coenzyme A, Stearoyl Coenzyme A, Oleoyl Coenzyme A, Arachidoyl Coenzyme A, Arachidonoyl Coenzyme A, Behenoyl Coenzyme A, Tricosanoyl Coenzyme A, Lignoceroyl Coenzyme A, Nervonoyl Coenzyme A, Hexacosanoyl Coenzyme A, iii) Sphingolipids, i.e. D-erythro (C-18) Derivatives (Sphingosine, such as: D-erythro Sphingosine (synthetic), Sphingosine-1-Phosphate, N,N Dimethylsphingosine, N,N,N-Trimethylsphingosine, Sphingosylphosphorylcholine, Sphingomyelin and Glycosylated Sphingosine), Ceramide Derivatives (Ceramides, D-erythro Ceramide-1-Phosphate, Glycosulated Ceramides), Sphinganine (Dihydrosphingosine) (Sphinganine-1-Phosphate, Sphinganine (C20), D-erythro Sphinganine, N-Acyl-Sphinganine C2, N-Acyl-Sphinganine C8, N-acyl-Sphinganine C16, N-Acyl-Sphinganine C18, N-Acyl-Sphinganine C24, N-Acyl-Sphinganine C24:1), Glycosylated (C18) Sphingosine and Phospholipid Derivatives (Glycosylated-Sphingosine) (Sphingosine, βD-Glucosyl, Sphingosine, βD-Galactosyl, Sphingosine, βD-Lactosyl), Glycosylated-Ceramide (D-Glucosyl-β1-1' Ceramide (C8), D-Galactosyl-β1-1' Ceramide (C8), D-Lactosyl-β1-1' Ceramide (C8), D-Glucosyl-β1-1' Ceramide (C12), D-Galactosyl-β1-1' Ceramide (C12), D-Lactosyl-β1-1' Ceramide (C12)), Glycosylated-Phosphatidylethanolamine (1,2-Dioleoyl-sn-Glycero-3-Phosphoethanolamine-N-Lactose), D-erythro (C17) Derivatives (D-erythro Sphingosine, D-erythro Sphingosine-1-phosphate), D-erythro (C20) Derivatives (D-erythro Sphingosine), L-threo (C18) Derivatives (L-threo Sphingosine, Safingol (L-threo Dihydrosphingosine)), Sphingosine Derivatives (Egg, Brain & Milk) (D-erythro-Sphingosine, Sphingomyelin, Ceramides, Cerebrosides, Brain Sulfatides), Gangliosides (Gangliosides Structures, Gangliosides—Ovine Brain, Gangliosides—Porcine Brain), Sphingosine Derivatives (Soy Bean) (Glucosylceramide), Phytosphingosine Derivatives (Yeast) (Phytosphingosine, D-ribo-Phytosphingosine-1-Phosphate, N-Acyl Phytosphingosine C2, N-Acyl Phytosphingosine C8, N-Acyl Phytosphingosine C18, iv) Acyl coenzyme A, i.e. Acetoyl Coenzyme A (Ammonium Salt), Butanoyl Coenzyme A (Ammonium Salt), Crotanoyl Coenzyme A (Ammonium Salt), Hexanoyl Coenzyme A (Ammonium Salt), Octanoyl Coenzyme A (Ammonium Salt), Decanoyl Coenzyme A (Ammonium Salt), Lauroyl Coenzyme A (Ammonium Salt), Myristoyl Coenzyme A (Ammonium Salt), Palmitoyl Coenzyme A (Ammonium Salt), Stearoyl Coenzyme A (Ammonium Salt), Oleoyl Coenzyme A (Ammonium Salt), Arachidoyl Coenzyme A (Ammonium Salt), Arachidonoyl Coenzyme A (Ammonium Salt), Behenoyl Coenzyme A (Ammonium Salt), Tricosanoyl Coenzyme A (Ammonium Salt), Lignoceroyl Coenzyme A (Ammonium Salt), Nervonoyl Coenzyme A (Ammonium Salt), Hexacosanoyl Coenzyme A (Ammonium Salt), Docosahexaenoyl Coenzyme A (Ammonium Salt), v) Oxidized lipids, i.e. 1-Palmitoyl-2-Azelaoyl-sn-Glycero-3-Phosphocholine, 1-O-Hexadecyl-2-Azelaoyl-sn-Glycero-3-Phosphocholine, 1-Palmitoyl-2-Glutaroyl-sn-Glycero-3-Phosphocholine (PGPC), 1-Palmitoyl-2-(9'-oxo-Nonanoyl)-sn-Glycero-3-Phosphocholine, 1-Palmitoyl-2-(5'-oxo-Valeroyl)-sn-Glycero-3-Phosphocholine, vi) Ether lipids, i.e.: Diether Lipids (Dialkyl Phosphatidylcholine, Diphytanyl Ether Lipids), Alkyl Phosphocholine (Dodedylphosphocholine), O-Alkyl diacylphosphatidylcholinium (1,2-Diacyl-sn-Glycero-3-Ethylphosphocholine), Synthetic PAF & Derivatives (1-Alkyl-2-Acyl-Glycero-3-Phosphocholine & Derivatives), vii) Fluorescent lipids, i.e.: Glycerol Based (Phosphatidylcholine (NBD), Phosphatidic Acid (NBD), Phosphatidylethanolamine (NBD), Phosphatidylglycerol (NBD), Phosphatidylserine (NBD)), Sphingosine Based (Ceramide (NBD), Sphingomyelin (NBD), Phytosphingosine (NBD), Galactosyl Cerebroside (NBD)), Headgroup Labeled Lipids (Glycerol Based) (Phosphatidylethanolamine (NBD), Phosphatidylethanolamine (Lissamine Rhodamine B), Dioleoyl Phosphatidylethanolamine (Dansyl, Pyrene, Fluorescein), Phosphatidylserine (NBD), Phosphatidylserine (Dansyl)), 25-NBD-Cholesterol, viii) Other lipids including, but not limited to Lecithin, Ultralec-P (ADM), Soy powder, ix) Surfactants including, but not limited to polyethylene glycol 400; sodium lauryl sulfate; sorbitan laurate, sorbitan palmitate, sorbitan stearate (available under the tradename Span® 20-40-60 etc.); polysorbates such as polyoxyethylene (20) sorbitan monolaurate, polyoxyethylene (20) sorbitan monopalmitate, polyoxyethylene (20) sorbitan monostearate (available under the tradename TWEENS® 20-40-60 etc.); benzalkonium chloride.

In certain embodiments, the phospholipids for use are phosphatidylcholines, phosphatidylethanolamines, phosphatidylserines, phosphatidylglycerols, phosphatidylinositols, phosphatidic acids, mixed chain phospholipids, lysophospholipids, hydrogenated phospholipids, partially hydrogenated phospholipids, and mixtures thereof.

In certain embodiments, the surface active agent is selected from polysorbate-80, lecithin and phosphatidylcholine. The surface active agents are present in an amount sufficient to form a stable emulsion.

The amount of surface active agent can be empirically determined and is a function of the agent selected and the desired form of the resulting composition. The amount include can be from less than 0.1% by weight up to 35% or more. In certain embodiments, the surface active agent is present at a concentration of about 1%, 2%, 3%, 4%, 5%, 6%, 7%, 8%, 9%, 10%, 15%, 20% or 25% by weight up to about 30% by weight of the total weight of the composition. In certain embodiments, the surface active agent is present at a concentration of about 1% by weight up to about 20% by weight of the total weight of the composition. In certain embodiments, the surface active agent is present at a concentration of about 1% by weight up to about 15% by weight of the total weight of the composition. In other embodiments, the surface active agent is present at a concentration of about 1% by weight up to about 10% by weight of the total weight of the composition. In other embodiments, the surface active agent is present at a concentration of about 1% by weight up to about 8% by weight of the total weight of the composition. In other embodiments, the surface active agent is present at a concentration of about 1% by weight up to about 6% by weight of the total weight of the composition. In other embodiments, the surface active agent is present at a concentration of about 1% by weight up to about 4% by weight of the total weight of the composition. In other embodiments, the surface active agent is present at a concentration of about 20% by weight of the total weight of the composition. In other embodiments, the surface active agent is present at a concentration of about 15% by weight of the total weight of the composition. In other embodiments, the surface active agent is present at a concentration of about 13% by weight of the total weight of the composition. In other embodiments, the surface active agent is present at a concentration of about 11% by weight of the total weight of the composition. In other embodiments, the surface active agent is present at a concentration of about 8% by weight of the total weight of the composition. In other embodiments, the surface active agent is present at a concentration of about 6% by weight of the total weight of the composition. In other embodiments, the surface active agent is present at a concentration of about 4% by weight of the total weight of the composition. In other embodiments, the surface active agent is present at a concentration of about 2% by weight of the total weight of the composition. In other embodiments, the surface active agent is present at a concentration of about 1% by weight of the total weight of the composition.

The stable emulsions provided herein can contain one or more delivery vehicles selected from among micelles, liposomes and cubosomes and mixtures thereof, that encapsulate the active agent. The delivery vehicles encapsulating the active agent are then absorbed in the epithelium where the active agent is delivered.

d. Agents for Delivery

The compositions provided herein can contain one or more agents for delivery to a subject. Generally the agents are those that confer a biological effect. Any agent that can be formulated as described herein can be administered in the compositions provided herein. Where the agent is a therapeutic, the compositions contain a therapeutically effective amount of an agent to be delivered. The particular amount of active agent in a dosage will vary widely according to the nature of the active agent, the nature of the condition being treated, the age and size of the subject, and other parameters.

Generally, the amount of active agent in the composition will vary from less than about 0.01% by weight to about 20% by weight of the composition or more and typically are formulated for single dosage administration. A single dosage can vary from about 0.01 μg to 10 mg of an agent per kilogram of body weight of the host, with dosages from about 0.1 μg to 1 mg/kg being commonly employed. These concentrations, however, are general guidelines only and particular amounts and dosages may be selected based on the active agent being administered, the condition being treated, and the treatment regimen being employed. The concentration can be an amount of a drug or an active agent that is sufficient to provide the desired local or systemic effect and performance at a reasonable benefit/risk ratio to a subject attending any medical treatment.

Agents for delivery are selected from inorganic and organic drugs including, but not limited to drugs that act on the peripheral nerves, adrenergic receptors, cholinergic receptors, nervous system, skeletal muscles, cardiovascular system, smooth muscles, blood circulatory system, synaptic sites, neuro-effector junctional sites, endocrine system, hormone systems, immunological system, reproductive system, skeletal system, autocoid systems, alimentary and excretory systems, histamine systems, and the like. The active agents that can be delivered using the compositions provided herein include, but are not limited to, anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides, polysaccharides, and nutritional supplements including herbal supplements.

The level of agent to be delivered is from about 0.01% up to about 50%, from about 0.1% up to about 40%, from about 0.1% up to about 30%, from about 0.1% up to about 20%, from about 0.1% up to about 10%, from about 0.1% up to about 9%, from about 0.1% up to about 8%, from about 0.1% up to about 7%, from about 0.1% up to about 6%, from about 0.1% up to about 5%, from about 0.1% up to about 4%, from about 0.1% up to about 3%, from about 0.1% up to about 2%, or from about 0.1% up to about 1% by weight of the composition. The agent to be delivered can be water soluble, slightly water soluble, or oil soluble. In certain embodiments, the agent to be delivered is selected from anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, non denatured whey protein, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides, polysaccharides, and nutritional supplements including herbal supplements.

In certain embodiments, the active agent is selected as follows:

α-Adrenergic agonists such as Adrafinil, Adrenolone, Amidephrine, Apraclonidine, Budralazine, Clonidine, Cyclopentamine, Detomidine, Dimetofrine, Dipivefrin, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine Hydrochloride, Methylhexaneamine, Metizolene, Midodrine, Naphazoline, Norepinephrine, Norfenefrine, Octodrine, Octopamine, Oxymetazoline, Phenylephrine Hydrochloride, Phenylpropanolamine Hydrochloride, Phenylpropylmethylamine, Pholedrine, Propylhexedrine, Pseudoephedrine, Rilmenidine, Synephrine, Tetrahydrozoline, Tiamenidine, Tramazoline, Tuaminoheptane, Tymazoline, Tyramine and Xylometazoline;

β-Adrenergic agonists such as Albuterol, Bambuterol, Bitolterol, Carbuterol, Clenbuterol, Clorprenaline, Denopamine, Dioxethedrine, Dopexamine, Ephedrine, Epinephrine, Etafedrine, Ethylnorepinephrine, Fenoterol, Formoterol, Hexoprenaline, Ibopamine, Isoetharine, Isoproterenal, Mabuterol, Metaproterenol, Methoxyphenamine, Oxyfedrine, Pirbuterol, Prenalterol, Procaterol, Protokylol, Reproterol, Rimiterol, Ritodrine, Soterenol, Terbuterol and Xamoterol;

α-Adrenergic blockers such as Amosulalol, Arotinolol, Dapiprazole, Doxazosin, Ergoloid Mesylates, Fenspiride, Indoramin, Labetalol, Nicergoline, Prazosin, Terazosin, Tolazoline, Trimazosin and Yohimbine;

β-Adrenergic blockers such as Acebutolol, Alprenolol, Amosulalol, Arotinolol, Atenolol, Befunolol, Betaxolol, Bevantolol, Bisoprolol, Bopindolol, Bucumolol, Befetolol, Bufuralol, Bunitrolol, Bupranolol, Butidrine Hydrochloride, Butofilolol, Carazolol, Carteolol, Carvedilol, Celiprolol, Cetamolol, Cloranolol, Dilevalol, Epanolol, Esmolol, Indenolol, Labetalol, Levobunolol, Mepindolol, Metipranalol, Metoprolol, Moprolol, Nadoxolol, Nifenalol, Nipradilol, Oxprenolol, Penbutolol, Pindolol, Practolol, Pronethalol, Propranolol, Sotalol, Sulfinalol, Talinolol, Tertatolol, Timolol, Toliprolol and Xibenolol;

Alcohol deterrents such as Calcium Cyanamide Citrated, Disulfuram, Nadide and Nitrefazole;

Aldose reductase inhibitors such as Epalrestat, Ponalrestat, Sorbinil and Tolrestat;

Anabolics such as Androisoxazole, Androstenediol, Bolandiol, Bolasterone, Clostebol, Ethylestrenol; Formyldienolone, 4-Hydroxy-19-nortestosterone, Methandriol, Methenolone, Methyltrienolone, Nandrolone, Nandrolone Decanoate, Nandrolone p-Hexyloxyphenylpropionate, Nandrolone Phenpropionate, Norbolethone, Oxymesterone, Pizotyline, Quinbolone, Stenbolone and Trenbolone;

Analgesics (dental) such as Chlorobutanol, Clove and Eugenol;

Analgesics (narcotic) such as Alfentanil, Allylprodine, Alphaprodine, Anileridine, Benzylmorphine, Bezitramide, Buprenorphine, Butorphanol, Clonitazene, Codeine, Codeine Methyl Bromide, Codeine Phosphate, Codeine Sulfate, Desomorphine, Dextromoramide, Dezocine, Diampromide, Dihydrocodeine, Dihydrocodeinone Enol Acetate, Dihydromorphine, Dimenoxadol, Dimepheptanol, Dimethylthiambutene, Dioxaphetyl Butyrate, Dipipanone, Eptazocine, Ethoheptazine, Ethylmethlythiambutene, Ethylmorphine, Etonitazene, Fentanyl, Hydrocodone, Hydrocodone Bitartrate, Hydromorphone, Hydroxypethidine, Isomethadone, Ketobemidone, Levorphanol, Lofentanil, Meperidine, Meptazinol, Metazocine, Methadone Hydrochloride, Metopon, Morphine, Morphine Derivatives, Myrophine, Nalbuphine, Narceine, Nicomorphine, Norlevorphanol, Normethadone, Normorphine, Norpipanone, Opium, Oxycodone, Oxymorphone, Papavereturn, Pentazocine, Phenadoxone, Phenazocine, Pheoperidine, Piminodine, Piritramide, Proheptazine, Promedol, Properidine, Propiram, Propoxyphene, Sufentanil and Tilidine;

Analgesics (non-narcotic) such as Acetaminophen, Acetaminosalol, Acetanilide, Acetylsalicylsalicylic Acid, Alclofenac, Alminoprofen, Aloxiprin, Aluminum Bis(acetylsalicylate), Aminochlorthenoxazin, 2-Amino-4-picoline, Aminopropylon, Aminopyrine, Ammonium Salicylate, Antipyrine, Antipyrine Salicylate, Antrafenine, Apazone, Aspirin, Benorylate, Benoxaprofen, Benzpiperylon, Benzydamine, p-Bromoacetanilide, 5-Bromosalicylic Acid Acetate, Bucetin, Bufexamac, Bumadizon, Butacetin, Calcium Acetylsalicylate, Carbamazepine, Carbetidine, Carbiphene, Carsalam, Chloralantipyrine, Chlorthenoxazin(e), Choline Salicylate, Cinchophen, Ciramadol, Clometacin, Cropropamide, Crotethamide, Dexoxadrol, Difenamizole, Diflunisal, Dihydroxyaluminum Acetylsalicylate, Dipyrocetyl, Dipyrone, Emorfazone, Enfenamic Acid, Epirizole, Etersalate, Ethenzamide, Ethoxazene, Etodolac, Felbinac, Fenoprofen, Floctafenine, Flufenamic Acid, Fluoresone, Flupirtine, Fluproquazone, Flurbiprofen, Fosfosal, Gentisic Acid, Glafenine, Ibufenac, Imidazole Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Magnesium Acetylsalicylate, Methotrimeprazine, Metofoline, Miroprofen, Morazone, Morpholine Salicylate, Naproxen, Nefopam, Nifenazone, 5' Nitro-2' propoxyacetanilide, Parsalmide, Perisoxal, Phenacetin, Phenazopyridine Hydrochloride, Phenocoll, Phenopyrazone, Phenyl Acetylsalicylate, Phenyl Salicylate, Phenyramidol, Pipebuzone, Piperylone, Prodilidine, Propacetamol, Propyphenazone, Proxazole, Quinine Salicylate, Ramifenazone, Rimazolium Metilsulfate, Salacetamide, Salicin, Salicylamide, Salicylamide O-Acetic Acid, Salicylsulfuric Acid, Salsalte, Salverine, Simetride, Sodium Salicylate, Sulfamipyrine, Suprofen, Talniflumate, Tenoxicam, Terofenamate, Tetradrine, Tinoridine, Tolfenamic Acid, Tolpronine, Tramadol, Viminol, Xenbucin and Zomepirac;

Androgens such as Androsterone, Boldenone, Dehydroepiandrosterone, Fluoxymesterone, Mestanolone, Mesterolone, Methandrostenolone, 17-Methyltestosterone, 17α-Methyltestosterone 3-Cyclopentyl Enol Ether, Norethandrolone, Normethandrone, Oxandrolone, Oxymesterone, Oxymetholone, Prasterone, Stanlolone, Stanozolol, Testosterone, Testosterone 17-Chloral Hemiacetal, Testosterone 17β-Cypionate, Testosterone Enanthate, Testosterone Nicotinate, Testosterone Pheynylacetate, Testosterone Propionate and Tiomesterone;

Anesthetics such as Acetamidoeugenol, Alfadolone Acetate, Alfaxalone, Amucaine, Amolanone, Amylocalne Hydrochloride, Benoxinate, Benzocaine, Betoxycaine, Biphenamine, Bupivacaine, Butacaine, Butaben, Butanilicaine, Burethamine, Buthalital Sodium, Butoxycaine, Carticaine, 2-Chloroprocaine Hydrochloride, Cocaethylene, Cocaine, Cyclomethycaine, Dibucaine Hydrochloride, Dimethisoquin, Dimethocaine, Diperadon Hydrochloride, Dyclonine, Ecgonidine, Ecgonine, Ethyl Aminobenzoate, Ethyl Chloride, Etidocaine, Etoxadrol, β-Eucaine, Euprocin, Fenalcomine, Fomocaine, Hexobarbital, Hexylcaine Hydrochloride, Hydroxydione Sodium, Hydroxyprocaine, Hydroxytetracaine, Isobutyl p-Aminobenzoate, Kentamine, Leucinocaine Mesylate, Levoxadrol, Lidocaine, Mepivacaine, Meprylcaine Hydrochloride, Metabutoxycaine Hydrochloride, Methohexital Sodium, Methyl Chloride, Midazolam, Myrtecaine, Naepaine, Octacaine, Orthocaine, Oxethazaine, Parethoxycaine, Phenacaine Hydrochloride, Phencyclidine, Phenol, Piperocaine, Piridocaine, Polidocanol, Pramoxine, Prilocalne, Procaine, Propanidid, Propanocaine, Proparacaine, Propipocaine, Propofol, Propoxycaine Hydrochloride, Pseudococaine, Pyrrocaine, Quinine Urea Hydrochloride, Risocaine, Salicyl Alcohol, Tetracaine Hydrochloride, Thialbarbital, Thimylal, Thiobutabarbital, Thiopental Sodium, Tolycaine, Trimecaine and Zolamine;

Anorexics such as Aminorex, Amphecloral, Amphetamine, Benzaphetamine, Chlorphentermine, Clobenzorex, Cloforex, Clortermine, Cyclexedrine, Destroamphetamine Sulfate, Diethylpropion, Diphemethoxidine, N-Ethylamphetamine, Fenbutrazate, Fenfluramine, Fenproporex, Furfurylmethylamphetamine, Levophacetoperate, Mazindol, Mefenorex, Metamfeproamone, Methamphetamine, Norpseudoephedrine, Phendimetrazine, Phendimetrazine Tartrate, Phenmetrazine, Phenpentermine, Phenylpropanolamine Hydrochloride and Picilorex;

Anthelmintics (Cestodes) such as Arecoline, Aspidin, Aspidinol, Dichlorophen(e), Embelin, Kosin, Napthalene, Niclosamide, Pellertierine, Pellertierine Tannate and Quinacrine;

Anthelmintics (Nematodes) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dymanthine, Gentian Violet, 4-Hexylresorcinol, Kainic Acid, Mebendazole, 2-Napthol, Oxantel, Papain, piperazine, piperazine Adipate, piperazine Citrate, piperazine Edetate Calcium, piperazine Tartrate, Pyrantel, Pyrvinium Pamoate, α-Santonin, Stilbazium Iodide, Tetrachloroethylene, Tetramisole, thiabendazole, Thymol, Thymyl N-Isoamylcarbamate, Triclofenol piperazine and Urea Stibamine;

Anthelmintics (Onchocerca) such as Ivermectin and Suramin Sodium;

Anthelmintics (Schistosoma) such as Amoscanate, Amphotalide, Antimony Potassium Tartrate, Antimony Sodium Gluconate, Antimony Sodium Tartrate, Antimony Sodium Thioglycollate, Antimony Thioglycollamide, Becanthone, Hycanthone, Lucanthone Hydrochloride, Niridazole, Oxamniquine, Praziquantel, Stibocaptate, Stibophen and Urea Stibamine;

Anthelmintics (Trematodes) such as Anthiolimine and Tetrachloroethylene;

Antiacne drugs such as Adapelene, Algestone Acetophenide, Azelaic Acid, Benzoyl Peroxide, Cyoctol, Cyproterone, Motretinide, Resorcinol, Retinoic Acid, Tetroquinone and Tretinonine;

Antiallergics such as Amlexanox, Astemizole, Azelastine, Cromolyn, Fenpiprane, Histamine, Ibudilast, Nedocromil, Oxatomide, Pentigetide, Poison Ivy Extract, Poison Oak Extract, Poison Sumac Extract, Repirinast, Tranilast, Traxanox and Urushiol;

Antiamebics such as Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Dephetarsone, Emetine, Fumagillin, Glaucarubin, Glycobiarsol, 8-Hydroxy-7-iodo-5-quinolinesulfonic Acid, Iodochlorhydroxyquin, Iodoquinol, Paromomycin, Phanquinone, Phearsone Sulfoxylate, Polybenzarsol, Propamidine, Quinfamide, Secnidazole, Sulfarside, Teclozan, Tetracycline, Thiocarbamizine, Thiocarbarsone and Timidazole;

Antiandrogens such as Bifluranol, Cyoctol, Cyproterone, Delmadinone Acetate, Flutimide, Nilutamide and Oxendolone;

Antianginals such as Acebutolol, Alprenolol, Amiodarone, Amlodipine,

Arotinolol, Atenolol, Bepridil, Bevantolol, Bucumolol, Bufetolol, Bufuralol, Bunitrolol, Bupranolol, Carazolol, Carteolol, Carvedilol, Celiprolol, Cinepazet Maleate, Diltiazem, Epanolol, Felodipine, Gallopamil, Imolamine, Indenolol, Isosorbide Dinitrate, Isradipine, Limaprost, Mepindolol, Metoprolol, Molsidomine, Nadolol, Nicardipine, Nifedipine, Nifenalol, Nilvadipine, Nipradilol, Nisoldipine, Nitroglycerin, Oxprenolol, Oxyfedrine, Ozagrel, Penbutolol, Pentaerythritol Tetranitrate, Pindolol, Pronethalol, Propranolol, Sotalol, Terodiline, Timolol, Toliprolol and Verapamil;

Antiarrhythmics such as Acebutolol, Acecaine, Adenosine, Ajmaline, Alprenolol, Amiodarone, Amoproxan, Aprindine, Arotinolol, Atenolol, Bevantolol, Bretylium Tosylate, Bucumolol, Bufetolol, Bunaftine, Bunitrolol, Bupranolol, Butidrine Hydrochloride, Butobendine, Capobenic Acid, Carazolol, Carteolol, Cifenline, Cloranolol, Disopyramide, Encamide, Esmolol, Flecamide, Gallopamil, Hydroquinidine, Indecamide, Indenolol, Ipratropium Bromide, Lidocaine, Lorajmine, Lorcamide, Meobentine, Metipranolol, Mexiletine, Moricizine, Nadoxolol, Nifenalol, Oxprenolol, Penbutolol, Pindolol, Pirmenol, Practolol, Prajmaline, Procainamide Hydrochloride, Pronethalol, Propafenone, Propranolol, Pyrinoline, Quinidine Sulfate, Quinidine, Sotalol, Talinolol, Timolol, Tocamide, Verapamil, Viquidil and Xibenolol;

Antiarteriosclerotics such as Pyridinol Carbamate;

Antiarthritic/Antirheumatics such as Allocupreide Sodium, Auranofin, Aurothioglucose, Aurothioglycanide, Azathioprine, Calcium 3-Aurothio-2-propanol-1-sulfonate, Celecoxib, Chloroquine, Clobuzarit, Cuproxoline, Diacerein, Glucosamine, Gold Sodium Thiomalate, Gold Sodium Thiosulfate, Hydroxychloroquine, Kebuzone, Lobenzarit, Melittin, Methotrexate, Myloral and Penicillamine;

Antibacterial (antibiotic) drugs including: Aminoglycosides such as Amikacin, Apramycin, Arbekacin, Bambermycins, Butirosin, Dibekacin, Dihydrostreptomycin, Fortimicin(s), Gentamicin, Isepamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols such as Azidamfenicol, Chloramphenicol, Chloramphenicol Palmitate, Chloramphenicol Pantothenate, Florfenicol and Thiamphenicol;

Ansamycins such as Rifamide, Rifampin, Rifamycin and Rifaximin;

β-Lactams, including: Carbapenems such as Imipenem;

Cephalosporins such as Cefactor, Cefadroxil, Cefamandole, Cefatrizine, Cefazedone, Cefazolin, Cefixime, Cefinenoxime, Cefodizime, Cefonicid, Cefoperazone, Cefo- ranide, Cefotaxime, Cefotiam, Cefpimizole, Cefpiramide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefotan and Cefoxitin;

Monobactams such as Aztreonam, Carumonam and Tigemonam;

Oxacephems such as Flomoxef and Moxalactam;

Penicillins such as Amdinocillin, Amdinocillin Pivoxil, Amoxicillin, Ampicillin, Apalcillin, Aspoxicillin, Azidocillin, Azlocillin, Bacampicillin, Benzylpenicillinic Acid, Benzylpenicillin Sodium, Carbenicillin, Carfecillin Sodium, Carindacillin, Clometocillin, Cloxacillin, Cyclacillin, Dicloxacillin, Diphenicillin Sodium, Epicillin, Fenbenicillin, Floxacillin, Hetacillin, Lenampicillin, Metampicillin, Methicillin Sodium, Mezlocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillin N, Penicillin O, Penicillin V, Penicillin V Benzathine, Penicillin V Hydrabamine, Penimepicycline, Phenethicillin Potassium, Piperacillin, Pivampicillin, Propicillin, Quinacillin, Sulbenicillin, Talampicillin, Temocillin and Ticarcillin;

Lincosamides such as Clindamycin and Lincomycin;

Macrolides such as Azithromycin, Carbomycin, Clarithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin, Viomycin Pantothenate, Virginiamycin and Zinc Bacitracin;

Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and other antibiotics such as Cycloserine, Mupirocin and Tuberin;

Antibacterial drugs (synthetic), including: 2,4-Diaminopyrimidines such as Brodimoprim, Tetroxoprim and Trimethoprim;

Nitrofurans such as Furaltadone, Furazolium Chloride, Nifuradene, Nifuratel, Nifurfoline, Nifurpirinol, Nifurprazine, Nifurtoinol and Nitrofurantoin;

Quinolones and Analogs such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, $N_2$ Formylsulfisomidine, $N^2$-β-D-Glucosylsulfanilamide, Mafenide, 4'-(Methylsulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanole, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, Sulfanilamidomethanesulfonic Acid Triethanolamine Salt, 4-Sulfanilamidosalicylic Acid, N-Sulfanilylsulfanilamide, Sulfanilylurea, Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones such as Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, p,p'-Sulfonyldianiline-N,N'digalactoside, Sulfoxone Sodium and Thiazolsulfone; and others such as Clofoctol, Hexedine, Methenamine, Methenamine Anhydromethylene-citrate, Methenamine Hippurate, Methenamine Mandelate, Methenamine Sulfosalicylate, Nitroxoline and Xibornol;

Anticholinergics such as Adiphenine Hydrochloride, Alverine, Ambutonomium Bromide, Aminopentamide, Amixetrine, Amprotropine Phosphate, Anisotropine Methylbromide, Apoatropine, Atropine, Atropine N-Oxide, Benactyzine, Benapryzine, Benzetimide, Benzilonium Bromide, Benztropine Mesylate, Bevonium Methyl Sulfate, Biperiden, Butropium Bromide, N-Butylscopolammonium Bromide, Buzepide, Camylofine, Caramiphen Hydrochloride, Chlorbenzoxamine, Chlorphenoxamine, Cimetropium Bromide, Clidinium Bromide, Cyclodrine, Cyclonium Iodide, Cycrimine Hydrochloride, Deptropine, Dexetimide Dibutoline Sulfate, Dicyclomine Hydrochloride, Diethazine, Difemerine, Dihexyverine, Diphemanil Methylsulfate, N-(1,2-Diphenylethyl) nicotinamide, Dipiproverine, Diponium Bromide, Emepronium Bromide, Endobenzyline Bromide, Ethopropazine, Ethybenztropine, Ethylbenzhydramine, Etomidoline, Eucatropine, Fenpiverinium Bromide, Fentonium Bromide, Flutropium Bromide, Glycopyrrolate, Heteronium Bromide, Hexocyclium Methyl Sulfate, Homatropine, Hyoscyamine, Ipratropium Bromide, Isopropamide, Levomepate, Mecloxamine, Mepenzolate Bromide, Metcaraphen, Methantheline Bromide, Methixene, Methscopolamine Bromide, Octamylamine, Oxybutynin Chloride, Oxyphencyclimine, Oxyphenonium Bromide, Pentapiperide, Penthienate Bromide, Phencarbamide, Phenglutarimide, Pipenzolate Bromide, Piperidolate, Piperilate, Poldine Methysulfate, Pridinol, Prifinium Bromide, Procyclidine, Propantheline Bromide, Propenzolate, Propyromazine, Scopolamine, Scopolamine N-Oxide, Stilonium Iodide, Stramonium, Sultroponium, Thihexinol, Thiphenamil, Tiemonium Iodide, Timepidium Bromide, Tiquizium Bromide, Tridihexethyl Iodide, Trihexyphenidyl Hydrochloride, Tropacine, Tropenzile, Tropicamide, Trospium Chloride, Valethamate Bromide and Xenytropium Bromide;

Anticonvulsants such as Acetylpheneturide, Albutoin, Aloxidone, Aminoglutethimide, 4-Amino-3-hydroxybutyric Acid, Atrolactamide, Beclamide, Buramate, Calcium Bromide, Carbamazepine, Cinromide, Clomethiazole, Clonazepam, Decimemide, Diethadione, Dimethadione, Doxenitoin, Eterobarb, Ethadione, Ethosuximide, Ethotoin, Fluoresone, Garbapentin, 5-Hydroxytryptophan, Lamotrigine, Lamictal, Magnesium Bromide, Magnesium Sulfate, Mephenyloin, Mephobarbital, Metharbital, Methetoin, Methsuximide, 5-Methyl-5-(3-phenanthryl)hydantoin, 3-Methyl-5-phenylhydantoin, Narcobarbital, Nimetazepam, Nitrazepam, Paramethadione, Phenacemide, Phenetharbital, Pheneturide, Phenobarbital, Phenobarbital Sodium, Phensuximide, Phenylmethylbarbituric Acid, Phenyloin, Phethenylate Sodium, Potassium Bromide, Pregabalin, Primidone, Progabide, Sodium Bromide, Sodium Valproate, Solanum, Strontium Bromide, Suclofenide, Sulthiame, Tetrantoin, Tiagabine, Trimethadione, Valproic Acid, Valpromide, Vigabatrin and Zonisamide;

Antidepressants, including: Bicyclics such as Binedaline, Caroxazone, Citalopram, Dimethazan, Indalpine, Fencamine, Fluvoxamine Maleate, Indeloxazine Hydrochloride, Nefopam, Nomifensine, Oxitriptan, Oxypertine, Paroxetine, Sertraline, Thiazesim, Trazodone, Venlafaxine and Zometapine;

Hydrazides/Hydrazines such as Benmoxine, Iproclozide, Iproniazid, Isocarboxazid, Nialamide, Octamoxin and Phenelzine;

Pyrrolidones such as Cotinine, Rolicyprine and Rolipram;

Tetracyclics such as Maprotiline, Metralindole, Mianserin and Oxaprotiline;

Tricyclics such as Adinazolam, Amitriptyline, Amitriptylinoxide, Amoxapine, Butriptyline, Clomipramine, Demexiptiline, Desipramine, Dibenzepin, Dimetacrine, Dothiepin, Doxepin, Fluacizine, Imipramine, Imipramine N-Oxide, Iprindole, Lofepramine, Melitracen, Metapramine, Nortriptyline, Noxiptilin, Opipramol, Pizotyline, Propizepine, Protriptyline, Quinupramine, Tianeptine and Trimipramine; and others such as Adrafinil, Benactyzine, Bupropion, Butacetin, Deanol, Deanol Aceglumate, Deanol Acetamidobenzoate, Dioxadrol, Etoperidone, Febarbamate, Femoxetine, Fenpentadiol, Fluoxetine, Fluvoxamine, Hematoporphyrin, Hypercinin, Levophacetoperane, Medifoxamine, Minaprine, Moclobemide, Oxaflozane, Piberaline, Prolintane, Pyrisuccideanol, Rubidium Chloride, Sulpiride, Sultopride, Teniloxazine, Thozalinone, Tofenacin, Toloxatone, Tranylcypromine, L-Tryptophan, Viloxazine and Zimeldine;

Antidiabetics, including: Biguanides such as Buformin, Metformin and Phenformin;

Hormones such as Glucagon, Insulin, Insulin Injection, Insulin Zinc Suspension, Isophane Insulin Suspension, Protamine Zinc Insulin Suspension and Zinc Insulin Crystals;

Sulfonylurea derivatives such as Acetohexamide, 1-Butyl-3-metanilylurea, Carbutamide, Chlorpropamide, Glibornuride, Gliclazide, Glipizide, Gliquidone, Glisoxepid, Glyburide, Glybuthiazol(e), Glybuzole, Glyhexamide, Glymidine, Glypinamide, Phenbutamide, Tolazamide, Tolbutamide and Tolcyclamide; and others such as Acarbose, Calcium Mesoxalate and Miglitol;

Antidiarrheal drugs such as Acetyltannic Acid, Albumin Tannate, Alkofanone, Aluminum Salicylates—Basic, Catechin, Difenoxin, Diphenoxylate, Lidamidine, Loperamide, Mebiquine, Trillium and Uzarin;

Antidiuretics such as Desmopressin, Felypressin, Lypressin, Ornipressin, Oxycinchophen, Pituitary—Posterior, Terlipressin and Vasopressin;

Antiestrogens such as Delmadinone Acetate, Ethamoxytriphetol, Tamoxifen and Toremifene;

Antifungal drugs (antibiotics), including: Polyenes such as Amphotericin-B, Candicidin, Dermostatin, Filipin, Fungichromin, Hachimycin, Hamycin, Lucensomycin, Mepartricin, Natamycin, Nystatin, Pecilocin and Perimycin; and others such as Azaserine, Griseofulvin, Oligomycins, Neomycin Undecylenate, PyrroInitrin, Siccanin, Tubercidin and Viridin;

Antifungal drugs (synthetic), including: Allylamines such as Naftifine and Terbinafine;

Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole, Nitrate, Sulconazole and Tioconazole;

Triazoles such as Fluconazole, Itraconazole and Terconazole; and others such as Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Tolciclate, Tolindate, Tolnaftate, Tricetin, Ujothion, Undecylenic Acid and Zinc Propionate;

Antiglaucoma drugs such as Acetazolamide, Befunolol, Betaxolol, Bupranolol, Carteolol, Dapiprazoke, Dichlorphenamide, Dipivefrin, Epinephrine, Levobunolol, Methazolamide, Metipranolol, Pilocarpine, Pindolol and Timolol;

Antigonadotropins such as Danazol, Gestrinone and Paroxypropione;

Antigout drugs such as Allopurinol, Carprofen, Colchicine, Probenecid and Sulfinpyrazone;

Antihistamines, including: Alkylamine derivatives such as Acrivastine, Bamipine, Brompheniramine, Chlorpheniramine, Dimethindene, Metron S, Pheniramine, Pyrrobutamine, Thenaldine, Tolpropamine and Triprolidine;

Aminoalkyl ethers such as Bietanautine, Bromodiphenhydramine, Carbinoxamine, Clemastine, Diphenylpyraline, Doxylamine, Embramine, Medrylamine, Mephenphydramine, p-Methyldiphenhydramine, Orphenadrine, Phenyltoloxamine, Piprinhydrinate and Setasine;

Ethylenediamine derivatives such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine Hydrochloride, Tripelennamine and Zolamine;

Piperazines such as Cetirizine, Chlorcyclizine, Cinnarizine, Clocinizine and Hydroxyzine;

Tricyclics, including: Phenothiazines such as Ahistan, Etymemazine, Fenethazine, N-Hydroxyethylpromethazine Chloride, Isopromethazine, Mequitazine, Promethazine, Pyrathiazine and Thiazinamium Methyl Sulfate; and others such as Azatadine, Clobenzepam, Cyproheptadine, Deptropine, Isothipendyl, Loratadine and Prothipendyl; and other antihistamines such as Antazoline, Astemizole, Azelastine, Cetoxime, Clemizole, Clobenztropine, Diphenazoline, Diphenhydramine, Fluticasone Propionate, Mebhydroline, Phenindamine, Terfenadine and Tritoqualine;

Antihyperlipoproteinemics, including: Aryloxyalkanoic acid derivatives such as Beclorbrate, Bezafibrate, Binifibrate, Ciprofibrate, Clinofibrate, Clofibrate, Clofibric Acid, Etofibrate, Fenofibrate, Gemfibrozil, Nicofibrate, Pirifibrate, Ronifibrate, Simfibrate and Theofibrate;

Bile acid sequesterants such as Cholestyramine Resin, Colestipol and Polidexide;

HMG CoA reductase inhibitors such as Fluvastatin, Lovastatin, Pravastatin Sodium and Simvastatin;

Nicotinic acid derivatives Aluminum Nicotinate, Acipimox, Niceritrol, Nicoclonate, Nicomol and Oxiniacic Acid;

Thyroid hormones and analogs such as Etiroxate, Thyropropic Acid and Thyroxine; and others such as Acifran, Azacosterol, Benfluorex, β-Benzalbutyramide, Carnitine, Chondroitin Sulfate, Clomestone, Detaxtran, Dextran Sulfate Sodium, 5,8,11,14,17-Eicosapentaenoic Acid, Eritadenine, Furazabol, Meglutol, Melinamide, Mytatrienediol, Ornithine, γ-Oryzanol, Pantethine, Pentaerythritol Tetraacetate, α-Phenylbutyramide, Pirozadil, Probucol, α-Sitosterol, Sultosilic Acid, piperazine Salt, Tiadenol, Triparanol and Xenbucin;

Antihypertensive drugs, including: Arylethanolamine derivatives such as Amosulalol, Bufuralol, Dilevalol, Labetalol, Pronethalol, Sotalol and Sulfinalol;

Aryloxypropanolamine derivatives such as Acebutolol, Alprenolol, Arotinolol, Atenolol, Betaxolol, Bevantolol, Bisoprolol, Bopindolol, Bunitrolol, Bupranolol, Butofilolol, Carazolol, Cartezolol, Carvedilol, Celiprolol, Cetamolol, Epanolol, Indenolol, Mepindolol, Metipranolol, Metoprolol, Moprolol, Nadolol, Nipradilol, Oxprenolol, Penbutolol, Pindolol, Propranolol, Talinolol, Tetraolol, Timolol and Toliprolol;

Benzothiadiazine derivatives such as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide, Meticrane, Metolazone, Paraflutizide, Polythiazide, Tetrachlormethiazide and Trichlormethiazide;

N-Carboxyalkyl (peptide/lactam) derivatives such as Alacepril, Captopril, Cilazapril, Delapril, Enalapril, Enalaprilat, Fosinopril, Lisinopril, Moveltipril, Perindopril, Quinapril and Ramipril;

Dihydropyridine derivatives such as Amlodipine, Felodipine, Isradipine, Nicardipine, Nifedipine, Nilvadipine, Nisoldipine and Nitrendipine;

Guanidine derivatives such as Bethanidine, Debrisoquin, Guanabenz, Guanacline, Guanadrel, Guanazodine, Guanethidine, Guanfacine, Guanochlor, Guanoxabenz and Guanoxan;

Hydrazines and phthalazines such as Budralazine, Cadralazine, Dihydralazine, Endralazine, Hydracarbazine, Hydralazine, Pheniprazine, Pildralazine and Todralazine;

Imidazole derivatives such as Clonidine, Lofexidine, Phentolamine, Phentolamine Mesylate, Tiamenidine and Tolonidine;

Quaternary ammonium compounds Azamethonium Bromide, Chlorisondamine Chloride, Hexamethonium, Pentacynium Bis(methyl sulfate), Pentamethonium Bromide, Pentolinium Tartrate, Phenactropinium Chloride and Trimethidinium Methosulfate;

Quinazoline derivatives such as Alfuzosin, Bunazosin, Doxazosin, Prasosin, Terazosin and Trimazosin;

Reserpine derivatives such as Bietaserpine, Deserpidine, Rescinnamine, Reserpine and Syrosingopine;

Sulfonamide derivatives such as Ambuside, Clopamide, Furosemide, Indapamide, Quinethazone, Tripamide and Xipamide; and others such as Ajmaline, γ-Aminobutyric Acid, Bufeniode, Candesartan, Chlorthalidone, Cicletanine, Ciclosidomine, Cryptenamine Tannates, Eprosartan, Fenoldopam, Flosequinan, Indoramin, Irbesartan, Ketanserin, Losartan, Mebutamate, Mecamylamine, Methyldopa, Methyl 4-Pyridyl Ketone Thiosemicarbazone, Metolazone, Minoxidil, Muzolimine, Pargyline, Pempidine, Pinacidil, Piperoxan, Primaperone, Protoveratrines, Raubasine, Rescimetol, Rilmenidine, Saralasin, Sodium Nitroprusside, Ticrynafen, Trimethaphan Camsylate, Tyrosinase, Urapidil and Valsartan;

Antihyperthyroids such as 2-Amino-4-methylthiazole, 2-Aminothiazole, Carbimazole, 3,5-Dibromo-L-tyrosine, 3,5-Diiodotyrosine, Hinderin, Iodine, lothiouracil, Methimazole, Methylthiouracil, Propylthiouracil, Sodium Perchlorate, Thibenzazoline, Thiobarbital and 2-Thiouracil;

Antihypotensive drugs such as Amezinium Methyl Sulfate, Angiotensin Amide, Dimetofrine, Dopamine, Etifelmine, Etilefrine, Gepefrine, Metaraminol, Midodrine, Norepinephrine, Pholedrine and Synephrine;

Antihypothyroid drugs such as Levothyroxine Sodium, Liothyronine, Thyroid, Thyroidin, Thyroxine, Tiratricol and TSH;

Anti-Inflammatory (non-steroidal) drugs, including: Aminoarylcarboxylic acid derivatives such as Enfenamic Acid, Etofenamate, Flufenamic Acid, Isonixin, Meclofenamic Acid, Mefanamic Acid, Niflumic Acid, Talniflumate, Terofenamate and Tolfenamic Acid;

Arylacetic acid derivatives such as Acemetacin, Alclofenac, Amfenac, Bufexamac, Cinmetacin, Clopirac, Diclofenac Sodium, Etodolac, Felbinac, Fenclofenac, Fenclorac, Fenclozic Acid, Fentiazac, Glucametacin, Ibufenac, Indomethacin, Isofezolac, Isoxepac, Lonazolac, Metiazinic Acid, Oxametacine, Proglumetacin, Sulindac, Tiaramide, Tolmetin and Zomepirac;

Arylbutyric acid derivatives such as Bumadizone, Butibufen, Fenbufen and Xenbucin;

Arylcarboxylic acids such as Clidanac, Ketorolac and Tinoridine;

Arylpropionic acid derivatives such as Alminoprofen, Benoxaprofen, Bucloxic Acid, Carprofen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Piketoprofen, Pirprofen, Pranoprofen, Protizinic Acid, Suprofen and Tiaprofenic Acid;

Pyrazoles such as Difenamizole and Epirizole;

Pyrazolones such as Apazone, Benzpiperylon, Feprazone, Mofebutazone, Morazone, Oxyphenbutazone, Phenybutazone, Pipebuzone, Propyphenazone, Ramifenazone, Suxibuzone and Thiazolinobutazone;

Salicylic acid derivatives such as Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, 1-Naphthyl Salicylate, Olsalazine, Parsalmide, Phenyl Acetylsalicylate, Phenyl Salicylate, Salacetamide, Salicylamine O-Acetic Acid, Salicylsulfuric Acid, Salsalate and Sulfasalazine;

Thiazinecarboxamides such as Droxicam, Isoxicam, Piroxicam and Tenoxicam; and others such as ε-Acetamidocaproic Acid, S-Adenosylmethionine, 3-Amino-4-hydroxybutyric Acid, Amixetrine, Bendazac, Benzydamine, Bucolome, Difenpiramide, Ditazol, Emorfazone, Guaiazulene, Nabumetone, Nimesulide, Orgotein, Oxaceprol, Paranyline, Perisoxal, Pifoxime, Proquazone, Proxazole and Tenidap;

Antimalarial drugs such as Acedapsone, Amodiaquin, Arteether, Artemether, Artemisinin, Artesunate, Bebeerine, Berberine, Chirata, Chlorguanide, Chloroquine, Chlorproguanil, Cinchona, Cinchonidine, Cinchonine, Cycloguanil, Gentiopicrin, Halofantrine, Hydroxychloroquine, Mefloquine Hydrochloride, 3-Methylarsacetin, Pamaquine, Plasmocid, Primaquine, Pyrimethamine, Quinacrine, Quinine, Quinine Bisulfate, Quinine Carbonate, Quinine Dihydrobromide, Quinine Dihydrochloride, Quinine Ethylcarbonate, Quinine Formate, Quinine Gluconate, Quinine Hydriodide, Quinine Hydrochloride, Quinine Salicylate, Quinine Sulfate, Quinine Tannate, Quinine Urea Hydrochloride, Quinocide, Quinoline and Sodium Arsenate Diabasic;

Antimigraine drugs such as Alpiropride, Dihydroergotamine, Eletriptan, Ergocornine, Ergocorninine, Ergocryptine, Ergot, Ergotamine, Flumedroxone acetate, Fonazine, Lisuride, Methysergid(e), Naratriptan, Oxetorone, Pizotyline, Rizatriptan and Sumatriptan;

Antinauseant drugs such as Acetylleucine Monoethanolamine, Alizapride, Benzquinamide, Bietanautine, Bromopride, Buclizine, Chlorpromazine, Clebopride, Cyclizine, Dimenhydrinate, Diphenidol, Domperidone, Granisetron, Meclizine, Methalltal, Metoclopramide, Metopimazine, Nabilone, Ondansetron, Oxypendyl, Pipamazine, Piprinhydrinate, Prochlorperazine, Scopolamine, Tetrahydrocannabinols, Thiethylperazine, Thioproperazine and Trimethobenzamide;

Antineoplastic drugs, including: Alkylating agents, such as Alkyl sulfonates such as Busulfan, Improsulfan and Piposulfan;

Aziridines such as Benzodepa, Carboquone, Meturedepa and Uredepa;

Ethylenimines and methylmelamines such as Altretamine, Triethylenemelamine, Triethylenephosphoramide, Triethylenethiophosphoramide and Trimethylolomelamine;

Nitrogen mustards such as Chlorambucil, Chlornaphazine, Cyclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard;

Nitrosoureas such as Carmustine, Chlorozotocin, Fotemustine, Lomustine, Nimustine and Ranimustine; and others such as Camptothecin, Dacarbazine, Mannomustine, Mitobronitol, Mitolactol and Pipobroman;

Antibiotics such as Aclacinomycins, Actinomycin $F_1$, Anthramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, Plicamycin, Porfiromycin, Puromycin, Streptonigrin, Streptozocin, Tubercidin, Ubenimex, Zinostatin and Zorubicin;

Antimetabolites, including: Folic acid analogs such as Denopterin, Methotrexate, Pteropterin and Trimetrexate;

Purine analogs such as Fludarabine, 6-Mercaptopurine, Thiamiprine and Thioguanine; and Pyrimidine analogs such as Ancitabine, Azacitidine, 6-Azauridine, Carmofur, Cytarabine, Doxifluridine, Enocitabine, Floxuridine Fluorouracil and Tegafur;

Enzymes such as L-Asparaginase; and others such as Aceglatone, Amsacrine, Bestrabucil, Bisantrene, Bryostatin 1, Carboplatin, Cisplatin, Defosfamide, Demecolcine, Diaziquone, Eflornithine, Elliptinium Acetate, Etoglucid, Etoposide, Gallium Nitrate, Hydroxyurea, Interferon-$\alpha$, Interferon-$\beta$, Interferon-$\gamma$, Interleukin-2, Lentinan, Letrozole, Lonidamine, Mitoguazone, Mitoxantrone, Mopidamol, Nitracrine, Pentostatin, Phenamet, Pirarubicin, Podophyllinic Acid, 2-Ethylhydrazide, Polynitrocubanes, Procarbazine, PSK7, Razoxane, Sizofuran, Spirogermanium, Taxol, Teniposide, Tenuazonic Acid, Triaziquone, 2.2'.2"-Trichlorotriethylamine, Urethan, Vinblastine, Vincristine, Vindesine and Vinorelbine;

Antineoplastic (hormonal) drugs, including: Androgens such as Calusterone, Dromostanolone Propionate, Epitiostanol, Mepitiostane and Testolactone;

Antiadrenals such as Aminoglutethimide, Mitotane and Trilostane;

Antiandrogens such as Flutamide and Nilutamide; and

Antiestrogens such as Tamoxifen and Toremifene;

Antineoplastic adjuncts including folic acid replenishers such as Frolinic Acid;

Antiparkinsonian drugs such as Amantadine, Benserazide, Bietanautine, Biperiden, Bromocriptine, Budipine, Cabergoline, Carbidopa, Deprenyl (a/k/a L-deprenyl, L-deprenil, L-deprenaline and selegiline), Dexetimide, Diethazine, Diphenhydramine, Droxidopa, Ethopropazine, Ethylbenzhydramine, Levodopa, Naxagolide, Pergolide, Piroheptine, Pramipexole, Pridinol, Prodipine, Quinpirole, Remacemide, Ropinirole, Terguride, Tigloidine and Trihexyphenidyl Hydrochloride;

Antipheochromocytoma drugs such as Metyrosine, Phenoxybenzamine and Phentolamine;

Antipneumocystis drugs such as Eflornithine, Pentamidine and Sulfamethoxazole;

Antiprostatic hypertrophydrugs such as Gestonorone Caproate, Mepartricin, Oxendolone and Proscar;

Antiprotozoal drugs (Leishmania) such as Antimony Sodium Gluconate, Ethylstibamine, Hydroxystilbamidine, N-Methylglucamine, Pentamidine, Stilbamidine and Urea Stibamine;

Antiprotozoal drugs (Trichomonas) such as Acetarsone, Aminitrozole, Anisomycin, Azanidazole, Forminitrazole, Furazolidone, Hachimycin, Lauroguadine, Mepartricin, Metronidazole, Nifuratel, Nifuroxime, Nimorazole, Secnidazole, Silver Picrate, Tenonitrozole and Tinidazole;

Antiprotozoal drugs (Trypanosoma) such as Benznidazole, Eflornithine, Melarsoprol, Nifurtimox, Oxophenarsine, Hydrochloride, Pentamidine, Propamidine, Puromycin, Quinapyramine, Stilbamidine, Suramin Sodium, Trypan Red and Tryparasmide;

Antipuritics such as Camphor, Cyproheptadine, Dichlorisone, Glycine, Halometasone, 3-Hydroxycamphor, Menthol, Mesulphen, Methdilazine, Phenol, Polidocanol, Risocaine, Spirit of Camphor, Thenaldine, Tolpropamine and Trimeprazine;

Antipsoriatic drugs such as Acitretin, Ammonium Salicylate, Anthralin, 6-Azauridine, Bergapten(e), Chrysarobin, Etretinate and Pyrogallol;

Antipsychotic drugs, including: Butyrophenones such as Benperidol, Bromperidol, Droperidol, Fluanisone, Haloperidol, Melperone, Moperone, Pipamperone, Spiperone, Timiperone and Trifluperidol;

Phenothiazines such as Acetophenazine, Butaperazine, Carphenazine, Chlorproethazine, Chlorpromazine, Clospirazine, Cyamemazine, Dixyrazine, Fluphenazine, Imiclopazine, Mepazine, Mesoridazine, Methoxypromazine, Metofenazate, Oxaflumazine, Perazine, Pericyazine, Perimethazine, Perphenazine, Piperacetazine, Pipotiazine, Prochlorperazine, Promazine, Sulforidazine, Thiopropazate, Thioridazine, Trifluoperazine and Triflupromazine;

Thioxanthenes such as Chlorprothixene, Clopenthixol, Flupentixol and Thiothixene;

other tricyclics such as Benzquinamide, Carpipramine, Clocapramine, Clomacran, Clothiapine, Clozapine, Opipramol, Prothipendyl, Tetrabenazine, and Zotepine; and others such as Alizapride, Amisulpride, Buramate, Fluspirilene, Molindone, Penfluridol, Pimozide, Spirilene and Sulpiride;

Antipyretics such as Acetaminophen, Acetaminosalol, Acetanilide, Aconine, Aconite, Aconitine, Alclofenac, Aluminum Bis(acetylsalicylate), Aminochlorthenoxazin, Aminopyrine, Aspirin, Benorylate, Benzydamine, Berberine, p-Bromoacetanilide, Bufexamac, Bumadizon, Calcium Acetylsalicylate, Chlorthenoxazin(e), Choline Salicylate, Clidanac, Dihydroxyaluminum Acetylsalicylate, Dipyrocetyl, Dipyrone, Epirizole, Etersalate, Imidazole Salicylate, Indomethacin, Isofezolac, p-Lactophenetide, Lysine Acetylsalicylate, Magnesium Acetylsalicylate, Meclofenamic Acid, Morazone, Morpholine Salicylate, Naproxen, Nifenazone, 51-Nitro-2'-propoxyacetanilide, Phenacetin, Phenicarbazide, Phenocoll, Phenopyrazone, Phenyl Acetylsalicylate, Phenyl Salicylate, Pipebuzone, Propacetamol, Propyphenazone, Ramifenazone, Salacetamide, Salicylamide O-Acetic Acid, Sodium Salicylate, Sulfamipyrine, Tetrandrine and Tinoridine;

Antirickettsial drugs such as p-Aminobenzoic Acid, Chloramphenicol, Chloramphenicol Palmitate, Chloramphenicol Pantothenate and Tetracycline;

Antiseborrheic drugs such as Chloroxine, 3-O-Lauroylpyridoxol Diacetate, Piroctone, Pyrithione, Resorcinol, Selenium Sulfides and Tioxolone;

Antiseptics, including: Guanidines such as Alexidine, Ambazone, Chlorhexidine and Picloxydine;

Halogens and halogen compounds such as Bismuth Iodide Oxide, Bismuth Iodosubgallate, Bismuth Tribromophenate, Bornyl Chloride, Calcium Iodate, Chlorinated Lime, Cloflucarban, Fluorosalan, Iodic Acid, Iodine, Iodine Monochloride, Iodine Trichloride, Iodoform, Methenamine Tetraiodine, Oxychlorosene, Povidone-Iodine, Sodium Hypochlorite, Sodium Iodate, Symclosene, Thymol Iodide, Triclocarban, Triclosan and Troclosene Potassium;

Mercurial compounds such as Hydrargaphen, Meralein Sodium, Merbromin, Mercuric Chloride, Mercuric Chloride, Ammoniated, Mercuric Sodium p-Phenol-sulfonate, Mercuric Succinimide, Mercuric Sulfide, Red, Mercurophen, Mercurous Acetate, Mercurous Chloride, Mercurous Iodide, Nitromersol, Potassium Tetraiodo-mercurate(II), Potassium Triiodomercurate (II) Solution, Thimerfonate Sodium and Thimerosal;

Nitrofurans such as Furazolidone, 2-(Methoxymethyl)-5-nitrofuran, Nidroxyzone, Nifuroxime, Nifurzide and Nitrofurazone;

Phenols such as Acetomeroctol, Bithionol, Cadmium Salicylate, Carvacrol, Chloroxylenol, Clorophene, Cresote, Cresol(s), p-Cresol, Fenticlor, Hexachlorophene, 1-Naphthyl Salicylate, 2-Naphthyl Salicylate, 2,4,6-Tribromo-m-cresol, and 3',4',5'-Trichlorosalicylanilide;

Quinolines such as Aminoquinuride, Benzoxiquine, Broxyquinoline, Chloroxine, Chlorquinaldol, Cloxyquin, Ethylhydrocupreine, Euprocin, Halquinol, Hydrastine, 8-Hydroxyquinoline, 8-Hydroxyquinoline Sulfate and Iodochlorhydroxyquin; and others such as Aluminum Acetate Solution, Aluminum Subacetate Solution, Aluminum Sulfate, 3-Amino-4-hydroxybutyric Acid, Boric Acid, Chlorhexidine, Chloroazodin, m-Cresyl Acetate, Cupric Sulfate, Dibromopropamidine, Ichthammol, Negatol, Noxytiolin, Ornidazole, β-Propiolactone, α-Terpineol;

Antispasmodic drugs such as Alibendol, Ambucetamide, Aminopromazine, Apoatropine, Bevonium Methyl Sulfate, Bietamiverine, Butaverine, Butropium Bromide, N-Butylscopolammonium Bromide, Caroverine, Cimetropium Bromide, Cinnamedrine, Clebopride, Coniine Hydrobromide, Coniine Hydrochloride, Cyclonium Iodide, Difemerine, Diisopromine, Dioxaphetyl Butyrate, Diponium Bromide, Drofenine, Emepronium Bromide, Ethaverine, Feclemine, Fenalamide, Fenoverine, Fenpiprane, Fenpiverinium Bromide, Fentonium Bromide, Flavoxate, Flopropione, Gluconic Acid, Guaiactamine, Hydramitrazine, Hymecromone, Leiopyrrole, Mebeverine, Moxaverine, Nafiverine, Octamylamine, Octaverine, Pentapiperide, Phenamacide Hydrochloride, Phloroglucinol, Pinaverium Bromide, Piperilate, Pipoxolan Hydrochloride, Pramiverin, Prifinium Bromide, Properidine, Propivane, Propyromazine, Prozapine, Racefemine, Rociverine, Spasmolytol, Stilonium Iodide, Sultroponium, Tiemonium Iodide, Tiquizium Bromide, Tiropramide, Trepibutone, Tricromyl, Trifolium, Trimebutine, N,N-Dimethyl-3,3-diphenyl-propylamine, Tropenzile, Trospium Chloride and Xenytropium Bromide;

Antithrombotic drugs such as Anagrelide, Argatroban, Cilostazol, Chrysoptin, Daltroban, Defibrotide, Enoxaparin, Fraxiparine, Indobufen, Lamoparan, Ozagrel, Picotamide, Plafibride, Reviparin, Tedelparin, Ticlopidine, Triflusal and Warfarin;

Antitussive drugs such as Alloclamide, Amicibone, Benproperine, Benzonatate, Bibenzonium Bromide, Bromoform, Butamirate, Butethamate, Caramiphen Ethanedisulfonate, Carbetapentane, Chlophedianol, Clobutinol, Cloperastine, Codeine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Enol Acetate, Dimemorfan, Dimethoxanate, α,α-Diphenyl-2-piperidinepropanol, Dropropizine, Drotebanol, Eprazinone, Ethyl Dibunate, Ethylmorphine, Fominoben, Guaiapate, Hydrocodone, Isoaminile, Levopropoxyphene, Morclofone, Narceine, Normethadone, Noscapine, Oxeladin, Oxolamine, Pholcodine, Picoperine, Pipazethate, Piperidione, Prenoxdiazine Hydrochloride, Racemethorphan, Taziprinone Hydrochloride, Tipepidine and Zipeprol;

Antiulcerative drugs such as Aceglutamide Aluminum Complex, ε-Acetamido-caproic Acid Zinc Salt, Acetoxolone, Arbaprostil, Benexate Hydrochloride, Bismuth Subcitrate Sol (Dried), Carbenoxolone, Cetraxate, Cimetidine, Enprostil, Esaprazole, Famotidine, Ftaxilide, Gefarnate, Guaiazulene, Irsogladine, Misoprostol, Nizatidine, Omeprazole, Ornoprostil, γ-Oryzanol, Pifamine, Pirenzepine, Plaunotol, Ranitidine, Rioprostil, Rosaprostol, Rotraxate, Roxatidine Acetate, Sofalcone, Spizofurone, Sucralfate, Teprenone, Trimoprostil, Trithiozine, Troxipide and Zolimidine;

Antiurolithic drugs such as Acetohydroxamic Acid, Allopurinol, Potassium Citrate and Succinimide;

Antivenin drugs such as Lyovac antivenin;

Antiviral drugs, including: Purines and pyrimidinones such as Acyclovir, Cytarabine, Dideoxyadenosine, Dideoxycytidine, Dideoxyinosine, Edoxudine, Floxuridine, Ganciclovir, Idoxuridine, Inosine Pranobex, MADU, Penciclovir, Trifluridine, Vidarabine and Zidovudine; and others such as Acetylleucine Monoethanolamine, Amantadine, Amidinomycin, Cosalane, Cuminaldehyde Thiosemicarbazone, Foscarnet Sodium, Imiquimod, Interferon-α, Interferon-β, Interferon-γ, Kethoxal, Lysozyme, Methisazone, Moroxydine, Podophyllotoxin, Ribavirin, Rimantadine, Stallimycin, Statolon, Tromantadine and Xenazoic Acid;

Anxiolytic drugs, including: Arylpiperazines such as Buspirone, Gepirone, Ipsapirone and Tandospirone;

Benzodiazepine derivatives such as Alprazolam, Bromazepam, Camazepam, Chlordiazepoxide, Clobazam, Clorazepate, Clotiazepam, Cloxazolam, Diazepam, Ethyl Loflazepate, Etizolam, Fludiazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam and Tofisopam;

Carbamates such as Cyclarbamate, Emylcamate, Hydroxyphenamate, Meprobamate, Phenprobamate and Tybamate; and others such as Alpidem, Benzoctamine, Captodiamine, Chlormezanone, Etifoxine, Flesinoxan, Fluoresone, Glutamic Acid, Hydroxyzine, Lesopitron, Mecloralurea, Mephenoxalone, Mirtazapine, Oxanamide, Phenaglycodol, Suriclone and Zatosetron;

Benzodiazepine antagonists such as Flumazenil;

Bronchodilators, including: Ephedrine derivatives such as Albuterol, Bambuterol, Bitolterol, Carbuterol, Clenbuterol, Clorprenaline, Dioxethedrin, Ephedrine, Epinephrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Salmeterol, Soterenol, Terbutaline and Tulobuterol;

Quaternary ammonium compounds such as Bevonium Methyl Sulfate, Clutropium Bromide, Ipratropium Bromide and Oxitropium Bromide;

Xanthine derivatives such as Acefylline, Acefylline piperazine, Ambuphylline, Aminophylline, Bamifylline, choline Theophyllinate, Doxofylline, Dyphylline, Enprofylline, Etamiphyllin, Etofylline, Guaithylline, Proxyphylline, Theobromine, 1-Theobromineacetic Acid and Theophylline; and others such as Fenspiride, Medibazine, Montelukast, Methoxyphenamine, Tretoquinol and Zafirlukast;

Calcium channel blockers, including: Arylalkylamines such as Bepridil, Ditiazem, Fendiline, Gallopamil, Prenylamine, Terodiline and Verapamil;

Dihydropyridine derivatives such as Felodipine, Isradipine, Nicardipine, Nifedipine, Nilvadipine, Nimodipine, Nisoldipine and Nitrendipine;

Piperazine derivatives such as Cinnarizine, Flunarizine and Lidoflazine; and others such as Bencyclane, Etafenone and Perhexyline;

Calcium regulators such as Calcifediol, Calcitonin, Calcitriol, Clodronic Acid, Dihydrotachysterol, Elcatonin, Etidronic Acid, Ipriflavone, Pamidronic Acid, Parathyroid Hormone and Teriparatide Acetate;

Cardiotonics such as Acefylline, Acetyldigititoxins, 2-Amino-4-picoline, Amrinone, Benfurodil Hemisuccinate, Buclasdesine, Cerberoside, Camphotamide, Convallatoxin, Cymarin, Denopamine, Deslanoside, Ditalin, Digitalis, Digitoxin, Digoxin, Dobutamine, Dopamine, Dopexamine, Enoximone, Erythropheine, Fenalcomine, Gitalin, Gitoxin, Glycocyamine, Heptaminol, Hydrastinine, Ibopamine, Lanotodises, Metamivam, Milrinone, Neriifolin, Oleandrin, Ouabain, Oxyfedrine, Prenalterol, Proscillaridin, Resibufogenin, Scillaren, Scillarenin, Strophanthin, Sulmazole, Theobromine and Xamoterol;

Chelating agents such as Deferoxamine, Ditiocarb Sodium, Edetate Calcium Disodium, Edetate Disodium, Edetate Sodium, Edetate Trisodium, Penicillamine, Pentetate Calcium Trisodium, Pentetic Acid, Succimer and Trientine;

Cholecystokinin antagonists such as Proglumide;

Cholelitholytic agents such as Chenodiol, Methyl tert-Butyl Ether, Monooctanoin and Ursodiol;

Choleretics such as Alibendol, Anethole Trithione, Azintamide, Cholic Acid, Cicrotoic Acid, Clanobutin, Cyclobutyrol, Cyclovalone, Cynarin(e), Dehydrocholic Acid, Deoxycholic Acid, Dimecrotic Acid, α-Ethylbenzyl Alcohol, Exiproben, Febuprol, Fencibutirol, Fenipentol, Florantyrone, Hymecromone, Menbutone, 3-(o-Methoxyphenyl)-2-phenylacrylic Acid, Metochalcone, Moquizone, Osalmid, Ox Bile Extract, 4.4'-Oxydi-2-butanol, Piprozolin, Prozapine, 4-Salicyloylmorpholine, Sincalide, Taurocholic Acid, Timonacic, Tocamphyl, Trepibutone and Vanitiolide;

Cholinergic agents such as Aceclidine, Acetylcholine Bromide, Acetycholide Chloride, Aclatonium Napadisilate, Benzpyrinium Bromide, Bethanechol chloride, Carbachol, Carpronium chloride, Demecarium Bromide, Dexpanthenol, Diisopropyl Paraoxon, Echothiophate Iodide, Edrophonium chloride, Eseridine, Furtrethonium, Isofluorophate, Methacholine chloride, Muscarine, Neostigmine, Oxapropanium Iodide, Physostigmine and Pyridostigmine Bromide;

Cholinesterase inhibitors such as Ambenonium Chloride, Distigmine Bromide and Galanthamine;

Cholinesterase reactivators such as Obidoxime Chloride and Pralidoxime Chloride;

Central nervous system stimulants and agents such as Amineptine. Amphetimine, Amphetaminil, Bemegride, Benzphetamine, Brucine, Caffeine, Chlorphentermine, Clofenciclan, Clortermine, Coca, Demanyl Phosphate, Dexoxadrol, Dextroamphetamine Sulfate, Diethylpropion, N-Ethylamphetamine, Ethamivan, Etifelmin, Etryptamine, Fencamfamine, Fenethylline, Fenozolone, Fluorothyl, Galanthamine, Hexacyclonate Sodium, Homocamfin, Mazindol, Mefexamide, Methamphetamine, Methylphenidate, Nikethamide, Pemoline, Pentylenetetrazole, Phendimetrazine, Phenmetrazine, Phentermine, Picrotoxin, Pipradrol, Prolintane and Pyrovalerone;

Decongestants such as Amidephrine, Cafaminol, Cyclopentamine, Ephedrine, Epinephrine, Fenoxazoline, Indanazoline, Metizoline, Naphazoline, Nordefrin Hydrochloride, Octodrine, oxymetazoline, Phenylephrine Hydrochloride, Phenylpropanolamine Hydrochloride, Phenylpropylmethylamine, Propylhexedrine, Pseudoephedrine, Tetrahydrozoline, Tymazoline and Xylometazoline;

Dental agents, including: Bisphosphonates (anti-periodontal disease and bone resorption) such as Alendronate, Clodronate, Etidronate, Pamidronate and Tiludronate; Carries Prophylactics such as Arginine and Sodium Fluoride;

Desensitizing Agents such as Potassium Nitrate and Citrate Oxalate;

Depigmentors such as Hydroquinine, Hydroquinone and Monobenzone;

Diuretics, including: Organomercurials such as Chlormerodrin, Meralluride, Mercamphamide, Mercaptomerin Sodium, Mercumallylic Acid, Mercumatilin Sodium, Mercurous Chloride and Mersalyl;

Pteridines such as Furterene and Triamterene;

Purines such as Acefylline, 7-Morpholinomethyltheophylline, Pamabrom, Protheobromine and Theobromine;

Steroids such as Canrenone, Oleandrin and Spironolactone;

Sulfonamide derivatives such as Acetazolamide, Ambuside, Azosemide, Bumetanide, Butazolamide, Chloraminophenamide, Clofenamide, Clopamide, Clorexolone, Diphenylmethane-4.4'-disulfonamide, Disulfamide, Ethoxzolamide, Furosemide, Indapamide, Mefruside, Methazolamide, Piretanide, Quinethazone, Torasemide, Tripamide and Xipamide;

Uracils such as Aminometradine and Amisometradine;

others such as Amanozine, Amiloride, Arbutin, Chlorazanil, Ethacrynic Acid, Etozolin, Hydracarbazine, Isosorbide, Mannitol, Metochalcone, Muzolimine, Perhexyline, Ticrynafen and Urea;

Dopamine receptor agonists such as Bromocriptine, Dopexamine, Fenoldopam, lbopamine, Lisuride, Naxagolide and Pergolide;

Ectoparasiticides such as Amitraz, Benzyl Benzoate, Carbaryl, Crotamiton, DDT, Dixanthogen, Isobornyl Thiocyanoacetate—Technical, Lime Sulfurated Solution, Lindane, Malathion, Mercuric Oleate, Mesulphen and Sulphur—Pharmaceutical;

Enzymes, including: Digestive enzymes such as α-Amylase (Swine Pancreas), Lipase, Pancrelipase, Pepsin and Rennin;

Mucolytic enzymes such as Lysozyme;

Penicillin inactivating enzymes such as Penicillinase; and

Proteolytic enzymes such as Collagenase, Chymopapain, Chymotrypsins, Papain and Trypsin;

Enzyme inducers (hepatic) such as Flumecinol;

Estrogens, including: Nonsteroidal estrogens such as Benzestrol, Broparestrol, Chlorotrianisene, Dienestrol, Diethylstilbestrol, Diethylstilbestrol Diprorionate, Dimestrol, Fosfestrol, Hexestrol, Methallenestril and Methestrol; and Steroidal estrogens such as Colpormon, Conjugated Estrogenic Hormones, Equilenin, Equilin, Estradiol, Estradiol Benzoate, Estradiol 17β-Cypionate, Estriol, Estrone, Ethinyl Estradiol, Mestranol, Moxestrol, Mytatrienediol, Quinestradiol and Quinestrol;

Gastric secretion inhibitors such as Enterogastrone and Octreotide;

Glucocorticoids such as 21-Acetoxypregnenolone, Alclometasone, Algestone, Amicinonide, Beclomethasone, Betamethasone, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumethasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Formocortal, Halcinonide, Halometasone, Halopredone Acetate, Hydrocortamate, Hydrocortisone, Hydrocortisone Acetate, Hydrocortisone Phosphate, Hydrocortisone 21-Sodium Succinate, Hydrocortisone Tebutate, Mazipredone, Medrysone, Meprednisone, Methylprednisolone, Mometasone Furoate, Paramethasone, Prednicarbate, Prednisolone, Prednisolone 21-Diethylaminoacetate, Prednisone Sodium Phosphate, Prednisolone Sodium Succinate, Prednisolone Sodium 21-m-Sulfobenzoate, Prednisolone 21-Stearoylglycolate, Prednisolone Tebutate, Prednisolone 21-Trimethylacetate, Prednisone, Prednival, Prednylidene, Prednylidene 21-Diethylaminoacetate, Tixocortol, Triamcinolone, Triamcinolone Acetonide, Triamcinolone Benetonide and Triamcinolone Hexacetonide;

Gonad-Stimulating principles such as Buserelin, Clomiphene, Cyclofenil, Epimestrol, FSH, HCG and LH-RH;

Gonadotropic hormones such as LH and PMSG;

Growth hormone inhibitors such as Octreotide and Somatostatin;

Growth hormone releasing factors such as Sermorelin;

Growth stimulants such as Somatotropin;

Hemolytic agents such as Phenylhydrazine and Phenylhydrazine Hydrochloride;

Heparin antagonists such as Hexadimethrine Bromide and Protamines;

Hepatoprotectants such as S-Adenosylmethionine, Betaine, Catechin, Citiolone, Malotilate, Orazamide, Phosphorylcholine, Protoporphyrin IX, Silymarin-Group, Thioctic Acid and Tiopronin;

Immunomodulators such as Amiprilose, Bucillamine, Ditiocarb Sodium, Inosine Pranobex, Interferon-y, Interleukin-2, Lentinan, Muroctasin, Platonin, Procodazole, Tetramisole, Thymomodulin, Thymopentin and Ubenimex;

Immunosuppressants such as Azathioprine, Cyclosporins and Mizoribine;

Ion exchange resins such as Carbacrylic Resins, Cholestyramine Resin, Colestipol, Polidexide, Resodec and Sodium Polystyrene Sulfonate;

Lactation stimulating hormone such as Prolactin;

LH-RH agonists such as Buserelin, Goserelin, Leuprolide, Nafarelin, and Triptorelin;

Lipotropic agents such as N-Acetylmethionine, Choline Chloride, Choline Dehydrocholate, Choline Dihydrogen Citrate, Inositol, Lecithin and Methionine;

Lupus erythematosus suppressants such as Bismuth Sodium Triglycollamate, Bismuth Subsalicylate, Chloroquine and Hydroxychloroquine;

Mineralocorticoids such as Aldosterone, Deoxycorticosterone, Deoxycorticosterone Acetate and Fludrocortisone;

Miotic drugs such as Carbachol, Physostigmine, Pilocarpine and Pilocarpus;

Monoamine oxidase inhibitors such as Deprenyl, Iproclozide, Iproniazid, Isocarboxazid, Moclobemide, Octamoxin, Pargyline, Phenelzine, Phenoxypropazine, Pivalylbenzhydrazine, Prodipine, Toloxatone and Tranylcypromine;

Mucolytic agents such as Acetylcysteine, Bromhexine, Carbocysteine, Domiodol, Letosteine, Lysozyme, Mecysteine Hydrochloride, Mesna, Sobrerol, Stepronin, Tiopronin and Tyloxapol;

Muscle relaxants (skeletal) such as Afloqualone, Alcuronium, Atracurium Besylate, Baclofen, Benzoctamine, Benzoquinonium Chloride, C-Calebassine, Carisoprodol, Chlormezanone, Chlorphenesin Carbamate, Chlorproethazine, Chlorzoxazone, Curare, Cyclarbamate, Cyclobenzaprine, Dantrolene, Decamethonium Bromide, Diazepam, Eperisone, Fazadinium Bromide, Flumetramide, Gallamine Triethiodide, Hexacarbacholine Bromide, Hexafluorenium Bromide, Idrocilamide, Laudexium Methyl Sulfate, Leptodactyline, Memantine, Mephenesin, Mephenoxalone, Metaxalone, Methocarbamol, Metocurine Iodide, Nimetazepam, Orphenadrine, Pancuronium Bromide, Phenprobamate, Phenyramidol, Pipecurium Bromide, Promoxolane, Quinine Sulfate, Styramate, Succinylcholine Bromide, Succinylcholine Chloride, Succinylcholine Iodine, Suxethonium Bromide, Tetrazepam, Thiocolchicoside, Tizanidine, Tolperisone, Tubocurarine Chloride, Vecuronium Bromide and Zoxolamine;

Narcotic antagonists such as Amiphenazole, Cyclazocine, Levallorphan, Nadide, Nalmefene, Nalorphine, Nalorphine Dinicotinate, Naloxone and Naltrexone;

Neuroprotective agents such as Dizocilpine;

Nootropic agents such as Aceglutamide, Acetylcarnitine, Aniracetam, Bifematlane, Exifone, Fipexide, ldebenone, lndeloxazine Hydrochloride, Nizofenone, Oxiracetam, Piracetam, Propentofylline, Pyritinol and Tacrine;

Ophthalmic agents such as 15-ketoprostaglandins;

Ovarian hormone such as Relaxin;

Oxytocic drugs such as Carboprost, Cargutocin, Deaminooxytocin, Ergonovine, Gemeprost, Methylergonovine, Oxytocin, Pituitary (Posterior), Prostaglandin $E_2$, Prostaglandin $F_{2a}$ and Sparteine;

Pepsin inhibitors such as Sodium Amylosulfate;

Peristaltic stimulants such as Cisapride;

Progestogens such as Allylestrenol, Anagestone, Chlormadinone Acetate, Delmadinone Acetate, Demegestone, Desogestrel, Dimethisterone, Dydrogesterone, Ethisterone, Ethynodiol, Fluorogestone Acetate, Gestodene, Gestonorone Caproate, Haloprogesterone, 17-Hydroxy-16-methylene—progesterone, 17α-Hydroxyprogesterone, 17α-Hydroxyprogesterone Caproate, Lynestrenol, Medrogestone, Medroxyprogesterone, Megestrol Acetate, Melengestrol, Norethindrone, Norethynodrel, Norgesterone, Norgestimate, Norgestrel, Norgestrienone, Norvinisterone, Pentagestrone, Progesterone, Promegestone, Quingestrone and Trengestone;

Prolactin inhibitors such as Metergoline;

Prostaglandins and prostaglandin analogs such as Arbaprostil, Carboprost, Enprostil, Gemeprost, Limaprost, Misoprostol, Ornoprostil, Prostacyclin, Prostaglandin $E_1$, Prostaglandin $E_2$, Prostaglandin $F_{2a}$, Rioprostil, Rosaprostol, Sulprostone and Trimoprostil;

Protease inhibitors such as Aprotinin, Camostat, Gabexate and Nafamostat;

Respiratory stimulants such as Almitrine, Bemegride, Carbon Dioxide, Cropropamide, Crotethamide, Dimefline, Dimorpholamine, Doxapram, Ethamivan, Fominoben, Lobeline, Mepixanox, Metamivam, Nikethamide, Picrotoxin, Pimeclone, Pyridofylline, Sodium Succinate and Tacrine;

Sclerosing agents such as Ethanolamine, Ethylamine, 2-Hexyl-decanoic Acid, Polidocanol, Quinine Bisulfate, Quinine Urea Hydrochloride, Sodium Ricinoleate, Sodium Tetradecyl Sulfate and Tribenoside;

Sedatives and hypnotics, including: Acyclic ureides such as Acecarbromal, Apronalide, Bromisovalum, Capuride, Carbromal and Ectylurea;

Alcohols such as Chlorhexadol, Ethchlorvynol, Meparfynol, 4-Methyl-5-thiazoleethanol, tert-Pentyl Alcohol and 2,2,2-Trichloroethanol;

Amides such as Butoctamide, Diethylbromoacetamide, Ibrotamide, Isovaleryl Diethylamide, Niaprazine, Tricetamide, Trimetozine, Zolpidem and Zopiclone;

Barbituric acid derivatives such as Allobarbital, Amobarbital, Aprobarbital, Barbital, Brallobarbital, Butabarbital Sodium, Butalbital, Butallylonal, Butethal, Carbubarb, Cyclobarbital, Cyclopentobarbital, Enallylpropymal, 5-Ethyl-5-(1-piperidyl) barbituric Acid, 5-Furfuryl-5-isopropylbarbituric Acid, Heptabarbital, Hexethal Sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetrabarbital, Vinbarbital Sodium and Vinylbital;

Benzodiazepine derivatives such as Brotizolam, Doxefazepam, Estazolam, Flunitrazepam, Flurazepam, Haloxazolam, Loprazolam, Lormetazepam, Nitrazepam, Quazepam, Temazepam and Triazolam;

Bromides such as Ammonium Bromide, Calcium Bromide, Calcium Bromolactobionate, Lithium Bromide, Magnesium Bromide, Potassium Bromide and Sodium Bromide;

Carbamates such as Amyl Carbamate—Tertiary, Ethinamate, Hexapropymate, Meparfynol Carbamate, Novonal and Tricholorourethan;

Chloral derivatives such as Carbocloral, Chloral Betaine, Chloral Formamide, Chloral Hydrate, Chloralantipyrine, Dichloralphenazone, Pentaerythritol Chloral and Triclofos;

Piperidinediones such as Glutethimide, Methyprylon, Piperidione, Pyrithyldione, Taglutimide and Thalidomide;

Quinazolone derivatives such as Etaqualone, Mecloqualone and Methaqualone; and others such as Acetal, Acetophenone, Aldol, Ammonium Valerate, Amphenidone, d-Bornyl α-Bromoisovalerate, d-Bornyl Isovalerate, Bromoform, Calcium 2-Ethylbutanoate, Carfimate, α-Chloralose, Clomethiazole, Cypripedium, Doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone, Sodium Oxybate, Sulfonethylmethane and Sulfonmethane;

Thrombolytic agents such as APSAC, Plasmin, Pro-Urokinase, Streptokinase, Tissue Plasminogen Activator and Urokinase;

Thyrotropic hormones such as TRH and TSH;

Uricosurics such as Benzbromarone, Ethebenecid, Orotic Acid, Oxycinchophen, Probenecid, Sulfinpyrazone, Ticrynafen and Zoxazolamine;

Vasodilators (cerebral) such as Bencyclane, Cinnarizine, Citicoline, Cyclandelate, Ciclonicate, Diisopropylamine Dichloroacetate, Eburnamonine, Fenoxedil, Flunarizine, Ibudilast, Ifenprodil, Nafronyl, Nicametate, Nicergoline, Nimodipine, Papaverine, Pentifylline, Tinofedrine, Vincamine, Vinpocetine and Viquidil;

Vasodilators (coronary) such as Amotriphene, Bendazol, Benfurodil Hemisuccinate, Benziodarone, Chloacizine, Chromonar, Clobenfurol, Clonitrate, Dilazep, Dipyridamole, Droprenilamine, Efloxate, Erythritol, Erythrityl Tetranitrate, Etafenone, Fendiline, Floredil, Ganglefene, Hexestrol Bis(β-diethylaminoethyl ether), Hexobendine, Itramin Tosylate, Khellin, Lidoflazine, Mannitol Hexanitrate, Medibazine, Nicorandil, Nitroglycerin, Pentaerythritol Tetranitrate, Pentrinitrol, Perhexyline, Pimethylline, Prenylamine, Propatyl Nitrate, Pyridofylline, Trapidil, Tricromyl, Trimetazidine, TroInitrate Phosphate and Visnadine;

Vasodilators (peripheral) such as Aluminum Nicotinate, Bamethan, Bencyclane, Betahistine, Bradykinin, Brovincamine, Bufeniode, Buflomedil, Butalamine, Cetiedil, Ciclonicate, Cinepazide, Cinnarizine, Cyclandelate, Diisopropylamine Dichloroacetate, Eledoisin, Fenoxedil, Flunarizine, Hepronicate, Ifenprodil, Inositol Niacinate, Isoxsuprine, Kallidin, Kallikrein, Moxisylyte, Nafronyl, Nicametate, Nicergoline, Nicofuranose, Nicotinyl Alcohol, Nylidrin, Pentifylline, Pentoxifylline, Piribedil, Prostaglandin $E_1$, Suloctidil and Xanthinol Niacinate;

Vasoprotectants such as Benzarone, Bioflavonoids, Chromocarb, Clobenoside, Diosmin, Dobesilate Calcium, Escin, Folescutol, Leucocyanidin, Metescufylline, Quercetin, Rutin and Troxerutin;

Vitamins, vitamin sources, and vitamin extracts such as Vitamins A, B, C, D, E, and K and derivatives thereof, Calciferols, Glycyrrhiza and Mecobalamin;

Vulnerary agents such as Acetylcysteine, Allantoin, Asiaticoside, Cadexomer Iodine, Chitin, Dextranomer and Oxaceprol;

Anticoagulants such as heparin; and

Miscellaneous such as Erythropoietin (Hematinic), Filgrastim, Finasteride (Benign Prostate Hypertrophy) and Interferon $\beta 1$-$\alpha$ (Multiple Sclerosis).

In certain embodiments, the agent to be delivered is one or more proteins, hormones, vitamins or minerals. In certain embodiments, the agent to be delivered is selected from insulin, IGF-1, testosterone, vinpocetine, hexarelin, GHRP-6 or calcium. In certain embodiments, the compositions contain two or more agents.

The above list of active agents is based upon those categories and species of drugs set forth on pages THER-1 to THER-28 of The Merck Index, 12th Edition, Merck & Co. Rahway, N.J. (1996). This reference is incorporated by reference in its entirety.

IV. Polymers

The compositions optionally contain one or more polymers that modify the viscosity of the composition. The polymer used can coat the liposome/micelle/proteins to keep the solution from degrading until it reaches the site of absorption, such as the mucosal lining. In certain embodiments, the polymers for use herein are selected from homopolymers such as polyolefins including polyethylene, polypropylene, polybutene, and polymers of higher alpha-olefins; styrenic polymers including polystyrene, polymers made from styrene monomers with pendant alkyl groups such as poly(alpha-methylstyrene) and poly(para-methyl styrene), and halogenated versions of the above styrenic polymers; polydienes including polybutadiene, polyisoprene, and other polymers made from alkylated diene monomers; polyamides; polyimides; polycarbonates; polyisobutylene; acrylics such as poly (methyl methacrylate), poly(butyl methacrylate), poly (acrylic acid); silicones such as poly(dimethyl siloxane) and the like; polysulfones; vinyl polymers such as poly(vinyl chloride), poly(vinyl flouride), poly(vinyl alcohol), poly(vinyl phenol), poly(vinylidene chloride), poly(vinylidene flouride), poly(tetrafluoro ethylene), poly(acrylonitrile), and the like; polyesters including poly(ethylene glycol) esters, poly (ethylene terephthalate), poly(butylene terephthalate), and the like; polyethers including poly(ethylene oxide), poly(propyleneoxide), poly(oxymethylene), and the like; poly(phenylene oxide); poly(phenylene sulfide); poly(acrylates); poly (benzimidazoles) and the like; and other polymers made from polymerizable monomers; statistical copolymers of the monomers or repeat units described above including for example copolymers of ethylene with other monomers such as alpha-olefins including propylene, butene-1, hexene, octene, and the like; dienes; vinyl acetate; vinyl alcohol; vinyl chloride; vinylidene chloride; copolymers of isobutylene with other monomers including isoprene, butadiene, para methylstyrene, styrene, and the like; copolymers of styrene with other monomers including butadiene, isoprene, maleic anhydride, acrylonitrile, oxazoline, and the like; copolymers of butadiene with other monomers including acrylonitrile;

copolymers of propylene with other monomers including ethylene, butene, hexane, dienes, and the like; block copolymers made from units of any of the above homopolymers or copolymers including styrene-diene block polymers such as styrene-isoprene-styrene triblock copolymer, styrene-butadiene-styrene triblock copolymers, styrene-ethylene/propylene-styrene triblock copolymers (all ratios of ethylene to propylene), and the like; graft copolymers made from units of any of the above homopolymers or copolymers including poly(ethylene-graft-propylene), poly(styrene-graft-butadiene) and the like; and derivatized versions of any of the above homopolymers or copolymers including for example those made by sulfonation, amination, and carboxylation and the like, such as sulfonated polystyrene, sulfonated ethylene-propylene-diene monomer, and the like. The term "polymer" as used herein also includes combinations or mixtures of more than one polymer wherein such combination or mixture exists in single or multiphase blends.

Generally the identity and composition (i.e. the ratio or amount of each type of copolymer unit desired) of the copolymer can be varied depending on the characteristics desired in the end product. It is within the skill of one ordinarily skilled in the art to make such selections.

In certain embodiments, the polymer for use herein is polyethylene glycol ester. In certain embodiments, the polyethylene glycol ester is selected from PEG 200 monolaurate, PEG 200 dilaurate, PEG 300 monolaurate, PEG 300 dilaurate, PEG 400 monolaurate, PEG 600 dilaurate, PEG 600 monolaurate, PEG 200 dilaurate, PEG 1000 monolaurate, PEG 1000 dilaurate, PEG 1540 monolaurate, PEG 1540 dilaurate, PEG 4000 monolaurate, PEG 4000 dilaurate, PEG 6000 monolaurate, PEG 6000 dilaurate, PEG 200 monostearate, PEG 200 distearate, PEG 300 monostearate, PEG 300 distearate, PEG 400 monostearate, PEG 600 distearate, PEG 600 monostearate, PEG 200 distearate, PEG 1000 monostearate, PEG 1000 distearate, PEG 1540 monostearate, PEG 1540 distearate, PEG 4000 monostearate, PEG 4000 distearate, PEG 6000 monostearate, PEG 6000 distearate, PEG 200 monooleate, PEG 200 dioleate, PEG 300 monooleate, PEG 300 dioleate, PEG 400 monooleate, PEG 600 dioleate, PEG 600 monooleate, PEG 200 dioleate, PEG 1000 monooleate, PEG 1000 dioleate, PEG 1540 monooleate, PEG 1540 dioleate, PEG 4000 monooleate, PEG 4000 dioleate, PEG 6000 monooleate and PEG 6000 dioleate.

In certain embodiments, the polymer used herein is PEG 400 distearate. In certain embodiments, PEG 400 distearate is present at a concentration of about 0.1% by weight up to about 10% by weight of the total weight of the composition. In other embodiments, PEG 400 distearate is present at a concentration of about 0.1% by weight up to about 8% by weight of the total weight of the composition. In other embodiments, PEG 400 distearate is present at a concentration of about 0.1% by weight up to about 6% by weight of the total weight of the composition. In other embodiments, PEG 400 distearate is present at a concentration of about 0.1% by weight up to about 4% by weight of the total weight of the composition. In other embodiments, PEG 400 distearate is present at a concentration of about 0.1% by weight up to about 2% by weight of the total weight of the composition. In other embodiments, PEG 400 distearate is present at a concentration of about 2% by weight of the total weight of the composition. In other embodiments, PEG 400 distearate is present at a concentration of about 1.8% by weight of the total weight of the composition. In other embodiments, PEG 400 distearate is present at a concentration of about 1.5% by weight of the total weight of the composition. In other embodiments, PEG 400 distearate is present at a concentration of about 1% by weight of the total weight of the composition. In other embodiments, PEG 400 distearate is present at a concentration of about 0.1% by weight of the total weight of the composition.

e. Cosolvent

The compositions provided herein can also contain one or more cosolvents. Such cosolvents are non-toxic, pharmaceutically acceptable substances, typically liquids, which do not substantially negatively affect the solubility of the active agents at the concentrations used. The cosolvent can aid in dissolving the active agent or for the mucoadhesive materials, or both. The cosolvent in certain embodiments, is a polyhydric alcohol or combination of polyhydric alcohols. In certain embodiments, the cosolvent is ethylene glycol, dipropylene glycol, propylene glycol, polyethylene glycol, glycerin, butylene glycol, hexylene glycol, polyoxyethylene, polypropylene glycol, sorbitol, ethylene glycol, or a mixture thereof.

The amount of cosolvent in the compositions provided herein depends on the solubility of the active agent and/or the mucoadhesive substance in the oil or water phase. Typically, the cosolvent is present in an amount sufficient to achieve complete dissolution of the active agent. In certain embodiments, the cosolvent is propylene glycol and is present at a concentration of about 1% by weight up to about 30% by weight of the total weight of the total composition. In other embodiments, propylene glycol is present at a concentration of about 1% by weight up to about 20% by weight of the total weight of the total composition. In other embodiments, propylene glycol is present at a concentration of about 1% by weight up to about 15% by weight of the total weight of the total composition. In other embodiments, propylene glycol is present at a concentration of about 1% by weight up to about 10% by weight of the total weight of the total composition. In other embodiments, propylene glycol is present at a concentration of about 15% by weight of the total weight of the total composition. In other embodiments, propylene glycol is present at a concentration of about 13% by weight of the total weight of the total composition. In other embodiments, propylene glycol is present at a concentration of about 11% by weight of the total weight of the total composition. In other embodiments, propylene glycol is present at a concentration of about 9.5% by weight of the total weight of the total composition. In other embodiments, propylene glycol is present at a concentration of about 7.5% by weight of the total weight of the total composition. In other embodiments, propylene glycol is present at a concentration of about 5% by weight of the total weight of the total composition. In other embodiments, propylene glycol is present at a concentration of about 3% by weight of the total weight of the total composition. In other embodiments, propylene glycol is present at a concentration of about 1% by weight of the total weight of the total composition.

f. Other Additives

The compositions provided herein can further contain one or more other additives such as taste modifying agents, a buffering agent, a chelating agent, a colorant, an osmotic modifier, a preservative, a sterilizer, a solubilizer, a tonicifier, a trace element, and a viscomodulator.

Taste modifying agents for use herein include, but are not limited to flavoring agents, sweetening agents and taste masking agents and are exemplified by: the essential oils or water soluble extracts of menthol, wintergreen, peppermint, sweet mint, spearmint, natural and artificial vanilla, cherry, chocolate, fudge, butterscotch, cinnamon, clove, lemon, orange, raspberry, rose, spice, violet, herbal, fruit, strawberry, grape, pineapple, peach, kiwi, papaya, mango, coconut, apple, coffee, plum, watermelon, nuts, durean, green tea, grapefruit, banana, butter, cream custard, camomile, sugar, dextrose, lactose, mannitol, sucrose, xylitol, maltitol, acesulfame potassium, talin, glycyrrhizin, sucralose, aspartame, saccharin, sodium saccharin, sodium cyclamate and honey. In certain embodiments, the taste modifying agent is selected from natural and artificial vanilla, cream custard, banana, fudge, butterscotch, coconut and chocolate.

Buffering agents include, but are not limited to acidulants and alkalizing agents exemplified by citric acid, fumaric acid, lactic acid, tartaric acid, malic acid, as well as sodium citrate, sodium bicarbonate and carbonate, sodium or potassium phosphate and magnesium oxide.

Coloring agents for use in the compositions include, but are not limited to FD & C coloring agents, natural coloring agents, and natural juice concentrates, pigments such as titanium oxide, silicon dioxide and zinc oxide.

Stabilizers as used in the compositions provided herein, include, but are not limited to anti-oxidants, chelating agents, and enzyme inhibitors as exemplified by ascorbic acid, vitamin E, butylated hydroxyanisole (BHA), butylated hydroxytoluene (BHT), propyl gallate, dilauryl thiodipropionate, thiodiproprionic acid, gum guaiac, citric acid, edetic acid and its salts and glutathione.

The compositions can contain preservatives which include, but are not limited sodium benzoate, potassium sorbate, parabens and derivatives, such as methyl paraben, propyl paraben, sorbic acid and its salts, propionic acids and its salts, sulfur dioxide and sulfites, acetic acid and acetates, and nitrites and nitrates.

g. Exemplary Compositions

Provided herein are compositions containing one or more agents formulated for mucosal delivery. The compositions provided are oil in water or water in oil emulsions. In certain embodiments, the oil phase in the compositions contains oat oil. The oil phase further contains one or more ingredients selected from the agent to be delivered, medium chain triglycerides, propylene glycol, preservatives and surfactants. The water phase of the compositions contains water and one or more ingredients selected from preservatives, surfactants, agent to be delivered and mucoadhesive proteins. In an exemplary embodiment, the mucoadhesive protein is albumin, immunoglobulin or lactoferrin; preservatives are selected from one among potassium sorbate, sodium benzoate, methyl paraben, propyl paraben and benzyl alcohol; the surfactants are phosphatidylcholine and polysorbate-80.

The compositions can contain oat oil from about 3% by weight up to about 25% by weight, generally about 3%, 4%, 7%, 7.5%, 8%, 15% or 25% by weight of the composition. The amount of MCT in the composition can be from about 10% by weight up to about 35% by weight, generally, 11%, 13%, 17%. 30% or 31% by weight of the composition. An exemplary composition can contain propylene glycol from about 8% by weight up to about 12% by weight, typically, 1%, 8%, 9%, 10% or 11% by weight of the composition. The mucoadhesive proteins are present, for example, from about 1% by weight up to about 11% by weight, typically 9%, 9.5% or 10% by weight of the composition.

C. Methods of Manufacturing the Compositions

The compositions provided herein are stable emulsions of oil in water or water in oil and are prepared by dissolving the components of the composition in the oil and/or water phases and mixing the two phases under constant temperature and pressure. They can be prepared by any suitable method for making emulsions.

1. Equipment Used in Exemplary Procedures Provided Herein Include:

i) Tanks

Two tanks, one for the oil phase and the other for a water phase. The size of the tank can vary depending on the amount of oil and water required to prepare the emulsion.

ii) Mixers

Mixers are used to blend, mix, emulsify and keep the material circulating in order to maintain temperature, viscosity, and other parameters to ensure the product meets the desired consistency. Mixers used in the procedures herein are: shears, inline mixers/mixing, Ribbon, Plow/Paddle Blenders, Forberg Mixers, Conveyors, Bag Dumps & Compactors, V-Blenders, Blade Mixers, Double Cone Mixers, Continuous Mixers, Speedflow Mixers, Batch Mixers, Double Ribbon Blenders, Paddle and Ribbon Mixers with Choppers, Plow Blenders/Turbulent Mixers, Fluidizing Forberg-Type Mixers, Air Mixers, Active Mixers, Passive Mixers, Top Entry Mixers, Side Entry Mixers, Static Mixers, Fixed Entry Mixers, Portable Mixers—both direct and gear drive, Sanitary Mixers, Drum Mixers, Bulk Container (IBC) Mixers, Lab Stirrers, Variable Speed Mixers, dough mixer, vertical mixer, spiral mixer, twin arm mixer, fork mixer, double spiral mixer, all agitators, and any other mixer applicable, agitator mixer, Banbury Mixer, Rubber Mixer, Blondheim Mixer, Chum Mixer, Conical Mixer, Continuous Mixer, Disperser Mixer, Pan Mixer, Emulsifier Mixer, Hobart Mixer, Liquifier Mixer, Littleford Mixer, Meat Mixer, Plow Mixer, Mixmuller Mixer, Nauta Mixer, Oakes Mixer, Planetary Mixer, Pony Mixer, PUG Mixer, Ribbon Mixer, Ross Mixer, Rotary Mixer, Sigma Mixer, Single Arm Mixer, Tote Bin Mixer, Tumble Mixer, Tumble Mixer, Vacuum Mixer, Turbolizer Mixer, Twin Shell Mixer, V-Type Mixer, Zig-Zag Mixer or side arm mixer.

iii) Heating Apparatus

Heating apparatus are used to heat the oil, water and emulsion phases and for cleaning/sanitizing equipment before and after use. Exemplary heating apparatus that can be used in the procedures provided herein are: Electrical jacketed tanks/kettles, water jacketed tanks/kettles, submersible heaters, semi-submersible heaters, immersible heaters, over-the-side heaters, straight hairpin heater tubes, steel sheath heaters, circular shaped heater tubes, incoloy sheath heaters, strip heaters, finned strip heaters, enclosure heaters, cartridge heaters, bolt heaters, component tubular heaters, finned tubular heaters, explosion resistant heaters, preweld heaters, bushing heaters, flanged heaters, bottom outlet heaters, circulation heaters, low temperature duct heaters and process heaters and other applicable heater apparatus.

Temperatures for heating solution and for cleaning/sanitizing range from 65° F. to about 220° F. During the dissolving and mixing steps, the temperature of the oil, water and emulsion phase is maintained at a level where the components of the composition retain their activity, for example the temperature is maintained such that the mucoadhesive protein does not denature during the process and the agent to be delivered does not degrade. A suitable temperature during the mixing step can be determined empirically for a particular combination of ingredients in the composition. Typically, the temperature is maintained at about 100-120° F., in some embodiments, at about 115° F. In certain embodiments, the temperature of the oil, water and emulsion phase during the process is maintained at about 120° F. In other embodiments, the temperature of the oil, water and emulsion phase is maintained at about 100° F. In other embodiments, the temperature is maintained at about 60-70° F. In other embodiments, the temperature is maintained at about 50° F.

The pressure for water jackets is maintained at a level selected so that the components of the composition do not degrade. In certain embodiments, the pressure is maintained at a range from 1 PSI to 120 PSI (pounds per square inch). In certain embodiments, the pressure is 50 PSI. In other embodiments, the pressure is 30 PSI. In other embodiments, the pressure is 25 PSI. In other embodiments, the pressure is 10 PSI.

2. Exemplary Procedures for Preparing the Compositions

Exemplary procedures for preparing the compositions are described below:

a. Procedure A

Included among the compositions provided herein are oil in water emulsions where the agent to be delivered is soluble in the water phase or in the oil phase. Such compositions can be prepared by any suitable method known in the art, including the following procedure. The compositions are prepared at a temperature and pressure at which all the oil and water soluble components are soluble in the oil and water phases, respectively and the mucoadhesive protein and the agent to be delivered are not degraded in any way. For example, the temperature for heating the solution can be maintained at about 100°-150° F., in certain embodiments, 115° F., for all phases; and the pressure is at maintained about 20-30 pounds-per-square inch (PSI). In certain embodiments, when using this range and a water jacket, the pressure can be about 25 PSI.

i) Oil Phase

The oils used in the oil phase are weighed, added in a suitable vessel, such as a reactor tank and mixed to form a solution. The solution is heated and maintained at a temperature where all the oil soluble components can be dissolved in the oil phase while retaining their activity. A suitable temperature during the mixing step can be determined empirically for a particular combination of ingredients in the composition. Typically, the temperature is maintained at about 100-120° F., in some embodiments at about 115° F. A cosolvent, such as propylene glycol, is weighed and mixed with the oil solution at a speed where complete dissolution of the ingredients is achieved without denaturing or otherwise leading to degradation of the any active ingredients. Generally, mixing is carried out at about 10 rpm, 50 rpm, 100 rpm, 150 rpm, 200 rpm, 250 rpm, 300 rpm or up to about 1000 rpm in oil phase. The oil preservatives, for example, methyl paraben and propyl paraben are weighed and added to the oil phase and the mixture is mixed to dissolve the preservatives. A sterile solution of benzyl hydroxide or benzyl benzoate is added and dissolved in the solution followed by addition of emulsifiers, lipids, phospholipids and polymers. If the agent to be delivered is soluble in the oil phase, it is added and mixed to dissolve. The temperature and pressure are maintained throughout the procedure to retain the activity of the agent to be delivered. In certain embodiments, the reactor vessel is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

ii) Water Phase

The required amount of water used in the water phase is weighed and added in a suitable vessel, such as a reactor tank. The water phase is heated and maintained at a predetermined temperature such that the mucoadhesive protein and the active agent, when soluble in the water phase, retain their activities. For example, in the compositions that contain lactoferrin, the temperature is maintained at or below 100 degrees F. or about 115° F., but not lower than 65-68 degrees F. in order prevent lactoferrin from denaturing. The temperature and pressure are monitored and maintained throughout the procedure. The preservatives, for example, Na Benzoate and K Sorbate are weighed and added to the water phase and the mixture is mixed to dissolve the preservatives. A predetermined amount of lipids, phospholipids and polymers to achieve a stable emulsion is added and dissolved. The temperature of the water phase is maintained at all times at a level that prevents denaturation of the mucoadhesive proteins. The mucoadhesive protein, required in an amount sufficient to achieve quantitative delivery of the agent to be delivered, is added to the water phase and mixed to dissolve. Where the agent to be delivered is water soluble, it is added and mixed to dissolve. The mixing is carried out at a speed where complete dissolution of the ingredients is achieved without denaturing or otherwise leading to degradation of the any active ingredients. Generally, mixing is carried out at about 10 rpm, 50 rpm, 100 rpm, 150 rpm, 200 rpm, 250 rpm, 300 rpm or up to about 1000 rpm in water phase. In certain embodiments, the reactor vessel, such as reactor tank, is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

iii) Formation of Emulsion

The oil phase is added to the water phase. This can be achieved, for example, by pumping, manually adding or any other means of transferring from the oil tank to the water tank. As the oil phase is being added to the water phase, the mixture is mixed at a speed sufficient to create the emulsion without denaturing or otherwise leading to degradation of the any active ingredients. The mixing can be effected at about 100 rpm, 300 rpm, 500 rpm, 700 rpm, 1000 rpm, 10,000 rpm, 20,000 rpm, 30,000 rpm, 40,000 rpm, 50,000 rpm, 60,000 rpm or up to about 100,000 rpm. The mixing step can involve shearing or just light mixing to create the emulsion. In certain embodiments, mixing is achieved by shearing. In certain embodiments, the pH of the emulsion is a function of the mucoadhesive protein used. The emulsion is maintained at neutral or basic pH throughout these steps.

b. Procedure B

Included among the compositions provided herein are water-in-oil emulsions, where the agent for delivery is soluble in the oil phase. They can be prepared by any suitable method, including the following procedure and any modifications thereof. In all phases the temperature and pressure of the solution are maintained at a level sufficient to dissolve all the ingredients while retaining the activity of mucoadhesive protein and the agent to be delivered. The temperature generally is maintained at about 90° F. to 110° F., typically at about 100° F. or 115° F. A suitable temperature during the mixing step can be determined empirically for a particular combination of ingredients in the composition. Typically, the temperature is maintained at about 100-120° F., in some embodiments, at about 115° F. Pressure is adjusted to achieve the dissolution of the components while maintaining the activity of the mucoadhesive protein and the agent to be delivered. For the temperature range used in the procedures provided herein, the pressure (in pounds-per-square inch PSI) is in the range of about 20 to about 30 PSI, typically the pressure in the water jacket for heating the mixture is maintained at about 25 PSI. Generally the water phase is added to the oil phase to produce a composition for mucosal delivery.

i) Oil Phase

The oils used in the oil phase are weighed and mixed. The solution is heated up to and maintained at a temperature where all the oil soluble components can be dissolved in the oil phase while retaining their activity, typical temperature is 100° F. and the temperature is maintained throughout the procedure. In some embodiments, suitable temperature during the mixing step can be determined empirically for a particular combination of ingredients in the composition. Typically, the temperature is maintained at about 115° F. A cosolvent, such as propylene glycol is weighed and dissolved at a predetermined RPM whereby complete dissolution of ingredients is achieved without denaturing or otherwise leading to degradation of the any active ingredients. Required amount of oil preservatives, such as methyl paraben and propyl paraben are added to oil phase, followed by sterile solution of benzyl hydroxide or benzyl benzoate. Emulsifiers are added and mixed to the oil phase, followed by addition of required amounts of lipids, phospholipids and polymers. Any oil soluble active agent is then weighed and added to the oil phase. In certain embodiments, the reactor vessel is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

ii) Water Phase

The required amount of water used in the water phase is weighed and added in a reactor tank. Water is heated and maintained at a temperature suitable for dissolution of the mucoadhesive protein and to prevent any degradation of the agent to be delivered. A cosolvent, such as propylene glycol is weighed and dissolved. Preservatives, for example, Na Benzoate and K Sorbate are weighed and added to the water phase and the mixture is mixed to dissolve the preservatives. Required amount of lipids, phospholipids and polymers to achieve stable emulsion are added and dissolved. For the compositions containing mucoadhesive proteins, such as lactoferrin, temperature is maintained at or below 100 degrees F., in certain embodiments, 115° F., but not lower than room temperature in order prevent the protein from denaturing. Temperature and pressure are maintained throughout the procedure. The mucoadhesive protein, required in an amount sufficient to achieve quantitative delivery of the agent to be delivered, is added to the water phase and mixed to dissolve. An agent to be delivered, if soluble in the water phase, is added and mixed to dissolve. In certain embodiments, the reactor vessel, such as reactor tank, is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

iii) Formation of Emulsion

The water phase is added to the oil phase. This can be achieved, for example, by pumping, manually adding or any other means of transferring from the oil tank to the water tank. As the oil phase is being added to the water phase, the mixture is mixed at a speed sufficient to create the emulsion without denaturing or otherwise leading to degradation of the any active ingredients. The mixing can be effected at about 100 rpm, 300 rpm, 500 rpm, 700 rpm, 1000 rpm, 10,000 rpm, 20,000 rpm, 30,000 rpm, 40,000 rpm, 50,000 rpm, 60,000 rpm or up to about 100,000 rpm. In certain embodiments, mixing is achieved by shearing. The emulsion is maintained at a temperature lower than the denaturing temperature of proteins, typically at about 100° F. or about 115° F. The emulsion is maintained at neutral or basic pH during these steps.

c. Procedure C

This procedure can be used for either oil in water or water in oil emulsion where the agent to be delivered is soluble in the water phase or in the oil phase. Such compositions can be prepared by any suitable method known in the art, including the following procedure. The compositions are prepared at a temperature and pressure at which all the oil and water soluble components are soluble in the oil and water phases, respectively and the mucoadhesive protein and the agent to be delivered are not degraded in any way. For example, the temperature for heating the solution can be maintained at about 100°-150° F. for all phases; and the pressure is at maintained about 20-30 pounds-per-square inch (PSI). For example, when using temperature in this range and a water jacket, the pressure can be about 25 PSI.

i) Oil Phase

Required amounts of all the oils used in this oil phase are weighed and mixed. The solution is heated and maintained at a temperature where all the oil soluble components can be dissolved in the oil phase while retaining their activity. In certain embodiments, the temperature is maintained at about 100° F.-150° F., typically at 100° F., or about 115° F. for all phases. A cosolvent, such as propylene glycol is weighed and dissolved at a predetermined RPM whereby complete dissolution of ingredients is achieved without denaturing or otherwise leading to degradation of the any active ingredients. Required amount of oil preservatives, such as methyl paraben and propyl paraben are added to oil phase, followed by sterile solution of benzyl hydroxide or benzyl benzoate. Emulsifiers are added and mixed in the oil phase, followed by addition of required amounts of lipids, phospholipids and polymers to achieve a stable emulsion. If the agent to be delivered is soluble in the oil phase, it is added and mixed to dissolve. The temperature and pressure are maintained throughout the procedure to retain the activity of the agent to be delivered. In certain embodiments, the reactor vessel, such as reactor tank, is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

ii) Water Phase

The required amount of water used in the water phase is weighed and added in a reactor tank. The water phase is heated and maintained at a predetermined temperature such that the mucoadhesive protein and the active agent, when soluble in water phase, retain their activities. For example, in the compositions that contain lactoferrin, the temperature is maintained at or below 100 degrees F., or about 115° F. but not lower than 65-68 degrees F. in order prevent lactoferrin from denaturing. The temperature and pressure are monitored and maintained throughout the procedure. A cosolvent, such as propylene glycol is weighed and dissolved at a predetermined RPM whereby complete dissolution of the ingredients is achieved without denaturing or otherwise leading to degradation of the any active ingredients. Preservatives, for example, Na Benzoate and K Sorbate are weighed and added to the water phase and the mixture is mixed to dissolve the preservatives. Required amount of lipids, phospholipids and polymers to achieve stable emulsion are added and dissolved. Temperature and pressure are maintained throughout the procedure. The mucoadhesive protein, required in an amount sufficient to achieve quantitative delivery of the agent to be delivered, is added to the water phase and mixed to dissolve. Where the agent to be delivered is water soluble, it is added and mixed to dissolve. In certain embodiments, the reactor vessel, reactor tank is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

iii) Formation of Emulsion

The water phase is added to the oil phase or oil phase can be added to water phase. This can be achieved, for example, by pumping, manually adding or any other means of transferring from the oil tank to the water tank. As the two phases are being added, the mixture is mixed at a speed sufficient to create the emulsion without denaturing or otherwise leading to degradation of the any active ingredients. The mixing can be effected at about 100 rpm, 300 rpm, 500 rpm, 700 rpm, 1000 rpm, 10,000 rpm, 20,000 rpm, 30,000 rpm, 40,000 rpm, 50,000 rpm, 60,000 rpm or up to about 100,000 rpm. The mixing step can involve shearing or just light mixing to create the emulsion. In certain embodiments, mixing is achieved by shearing. The emulsion is maintained at a temperature lower than the denaturing temperature of proteins, typically at about 100° F. or about 115° F. The emulsion is maintained at neutral or basic pH (pH 8-9) throughout these steps.

It is noted that various parameters described in the general procedures described above for the preparation of the water in oil and oil in water emulsions represent exemplary embodiments and are not intended to limit the scope of the subject matter provided herein.

D. Formulations

The compositions provided herein contain one or more agents for administration to a subject via the mucosa. The agents can be anything to be administered and in any amount. Typically the compositions contain therapeutically effective amounts of one or more biologically active agents that alter a biological function, such as a body function at the cellular, tissue or organ level and/or alters cosmetic appearance of a subject. In certain embodiments, the compositions provided herein are intended for delivery of biologically active agents through oral or nasal mucosa, thereby allowing for the avoidance of the gastrointestinal tract and first pass liver metabolism and consequently allowing the biologically active agent to directly enter into circulation.

The compositions provided herein are useful in altering a biological function, such as a body function at the cellular, tissue or organ level and/or altering cosmetic appearance of a subject. In certain embodiments, the compositions provided herein are useful in the prevention, treatment, or amelioration of one or more of the symptoms of diseases or disorders that can be treated by any agent that can be delivered to a mucosal surface via the compositions provided herein. The diseases or disorders treatable by the compositions provided include, but are not limited to neural disorders, respiratory disorders, immune system disorders, muscular disorders, reproductive disorders, gastrointestinal disorders, pulmonary disorders, digestive disorders, metabolic disorders, cardiovascular disorders, renal disorders, proliferative disorders, cancerous diseases and inflammation.

The compositions provided herein contain one or more agent to be delivered or pharmaceutically acceptable derivatives thereof. The compositions can be formulated into stable emulsions for mucosal delivery. In certain embodiments, the compositions have been found to be stable for up to 6 months.

The compositions are formulated as emulsions for administration to the oral or nasal mucosal membranes. Typically the compositions described above are formulated using techniques and procedures well known in the art (see, e.g., Ansel (1985) *Introduction to Pharmaceutical Dosage Forms*, Fourth Edition, p. 126)), including the procedures described above.

Typically, in the compositions provided herein, one or more agents to be delivered or pharmaceutically acceptable derivatives thereof is (are) present in the concentration that is effective for delivery of an amount, upon administration, that alters a biological function, such as a body function at the cellular, tissue or organ level and/or alters cosmetic appearance of a subject. Such alteration of a biological function or cosmetic appearance includes, but is not limited to treatment of diseases or disorders including, but are not limited to, neural disorders, respiratory disorders, immune system disorders, muscular disorders, reproductive disorders, gastrointestinal disorders, pulmonary disorders, digestive disorders, metabolic disorders, cardiovascular disorders, renal disorders, proliferative disorders, cancerous diseases and inflammation.

The compositions typically contain an agent to be delivered in an amount sufficient to exert a therapeutically useful effect in the absence of undesirable side effects on the subject. It is understood that the number and degree of side effects depends upon the condition for which the compositions are administered. For example, certain toxic and undesirable side effects are tolerated when treating life-threatening illnesses, such as tumors, that would not be tolerated when treating disorders of lesser consequence.

The concentration of the agent to be delivered in the composition will depend on absorption, inactivation and excretion rates thereof, the dosage schedule, and amount administered as well as other factors known to those of skill in the art. Typically a therapeutically effective dosage should produce a serum concentration of active ingredient from about 0.1 ng/ml to about 50-100 μg/ml. The compositions typically should provide a dosage of from about 0.01 mg to about 100-2000 mg of the agent to be delivered, depending upon the agent selected and adjusted for body surface area and/or weight. Typically, a daily dosage of about between 0.05 mg/kg and 0.5 mg/kg, in certain embodiments 10 mg/kg should be sufficient. The dosage is a function of the agent delivered. In certain embodiments, single dosages per administration contain 1-2 milliliters of 1, 10, 100, 200, 250, 500, 650, 1000, 1500, or 2000-2500 mgs of total material delivered and is a function of the agent delivered. In certain embodiments, 1, 2, 3, 4, 5 or more servings of the composition can be administered per day depending upon the agent delivered and disease treated. It is understood that the amount to administer is a function of the agent to be delivered, the alteration of a biological function or cosmetic appearance desired, and possibly the side effects that will be tolerated. Dosages can be empirically determined using recognized models for each effect desired.

Typically, the compositions are provided for administration to humans and animals in unit or multiple dosage forms as oil-water emulsions containing suitable quantities of one or more agents to be delivered or pharmaceutically acceptable derivative thereof. The unit-dose forms as used herein refers to physically discrete units suitable for human and animal subjects and packaged individually as is known in the art. Each unit-dose contains a predetermined quantity of the agent to be delivered sufficient to produce the desired effect, in association with the required additives in the composition. Unit-dose forms can be administered in fractions or multiples thereof. Examples of unit dosage include capsules filled with liquid compositions. A multiple-dose form is a plurality of identical unit-dosage forms packaged in a single container to be administered in segregated unit-dose form. Examples of multiple-dose forms include vials and bottles.

E. Methods of Use of the Compositions

Provided herein are methods of mucosal delivery of agents to subjects. The methods for mucosal delivery of an agent provided herein include providing a composition for mucosal delivery and contacting the composition with a mucosal surface of a subject, whereby the agent is delivered into the circulatory system of the subject. Contacting a mucosal surface, such as the oral, nasal or other mucosal surface, of a subject with a composition provided herein permits delivery of the composition and hence of any selected agent that can be formulated as an emulsion. Contacting can be effected by any suitable method. For example, methods provided herein include the steps of providing a pharmaceutical composition as described herein, including an agent for delivery and administering the composition to the mucosa of the subject, generally either by oral, intranasal inhalation or other method whereby the composition contacts mucosa in the subject.

In the methods provided herein, the compositions can contact, adhere and/or penetrate into the mucosal lining from about 1 minute up to about 24 hours or more, typically, about 1, 2, 3, 5, 10, 15, 20, 30, 60, or 120 minutes. In some embodiments, in the methods provided herein, the compositions can contact, adhere and/or penetrate into the mucosal lining for about 2, 3, 4, 6, 8, 10, 12, 14, 16, 18, 20, 22 or up to 24 hours.

The compositions provided herein can be administered by methods known to those of skill in the art, including, but not limited to delivering the composition in oral cavity or nasal cavity. The composition can be sprayed into the oral cavity or nasal cavity, administered as soft capsule filled with the liquid composition or contacted to the mucosal surface in the oral and nasal cavity by any other means known in the art. When delivering with a soft capsule, the capsule can then be chewed by the subject to release the composition into the oral cavity. The intranasal composition is applied to the nasal mucosa via topical application (spray and/or drops) of a safe and effective amount of the composition. The frequency of administration of the composition may vary, depending upon personal or medical needs, but generally ranges from about once per day to about four times daily.

The compositions are designed for delivery to a mucosal membrane whereby the agent to be delivered gets absorbed into the mucosa and directly enters into circulation. The amount of agent that is absorbed through the mucosal lining can be assessed by methods known in the art and described herein. For example, the amount of agent absorbed can be assessed by measuring the amount of agent administered to the subject and comparing it to the amount thereof found in a blood sample. The blood sample can be obtained at different time intervals. The interval of time can be empirically determined based on such factors as the agent to be delivered and the mode of administration. The amount of agent to be delivered per dosage depends on the amount of agent absorbed through the mucosal lining and other factors such as age and physical condition of the subject.

In certain embodiments, the methods are used for delivery of minerals, vitamins, pharmaceutical drugs, nutritional supplements, hormones, or the like, which when introduced into the body cause a desired biological response, such as altering body function at the cellular, tissue or organ level or altering cosmetic appearance. In certain embodiments, the agent delivered is a drug or other pharmaceutical ingredient, particularly one that has a significant loss of activity in the lumen of the gastrointestinal tract or in the tissues of the gastrointestinal tract during the absorption process or upon passage through the liver after absorption in the intestinal tract. In certain embodiments, the methods provided herein are useful for delivery of one or more active agents selected from anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides, polysaccharides, and nutritional supplements including herbal supplements.

Hence, provided herein are methods for treatment of diseases or disorders that can be treated by mucosal administration of active agents, such diseases and disorders include, but are not limited to neural disorders, respiratory disorders, immune system disorders, muscular disorders, reproductive disorders, gastrointestinal disorders, pulmonary disorders, digestive disorders, metabolic disorders, cardiovascular disorders, renal disorders, proliferative disorders, cancerous diseases and inflammation.

The immune system disorders that can be treated by the compositions provided herein include, but are not limited to systemic lupus erythematosus, rheumatoid arthritis, ankylosing spondylitis, multiple sclerosis, insulin resistant diabetes mellitus, autoimmune thyroiditis, Hashimoto's thyroiditis, autoimmune hemolytic anemia, hemolytic anemia, thrombocytopenia, autoimmune thrombocytopenia purpura, autoimmune neonatal thrombocytopenia, idiopathic thrombocytopenia purpura, autoimmunocytopenia, Goodpasture's syndrome, myasthenia gravis, Grave's disease (hyperthyroidism), type II collagen-induced arthritis, antiphospholipid syndrome, dermatitis, allergic encephalomyelitis, myocarditis, relapsing polychondritis, rheumatic heart disease, neuritis, uveitis ophthalmia, polyendocrinopathies, Reiter's Disease, Stiff-Man Syndrome, autoimmune pulmonary inflammation, autism, Guillain-Barre Syndrome, insulin dependent diabetes mellitus, autoimmune inflammatory eye disorders, scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes mellitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies), chronic active hepatitis (often characterized, e.g., by smooth muscle antibodies), primary biliary cirrhosis (often characterized, e.g., by mitochondria antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-M-1 (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulomatous, degenerative, and atrophic disorders.

In certain embodiments, the compositions are used in the methods to treat allergy related conditions, including, but not limited to allergic reactions include, but are not limited to, asthma, rhinitis, and eczema.

In certain embodiments, the compositions are used in the methods to treat inflammatory conditions including, but are not limited to, for example inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, overproduction of cytokines (e.g., TNF or IL-1.), respiratory disorders (e.g., asthma and allergy); gastrointestinal disorders (e.g., inflammatory bowel disease); cancers (e.g., gastric, ovarian, lung, bladder, liver, and breast); CNS disorders (e.g., multiple sclerosis; ischemic brain injury and/or stroke, traumatic brain injury, neurodegenerative disorders (e.g., Parkinson's disease and Alzheimer's disease); AIDS-related dementia; and prion disease); cardiovascular disorders (e.g., atherosclerosis, myocarditis, cardiovascular disease, and cardiopulmonary bypass complications); as well as many additional diseases, conditions, and disorders that are characterized by inflammation (e.g., hepatitis, rheumatoid arthritis, gout, trauma, pancreatitis, sarcoidosis, dermatitis; renal ischemia-reperfusion injury, Grave's disease, systemic lupus erythematosus, diabetes mellitus; and allogenic transplant rejection).

In certain embodiments, the methods provided herein are useful for treatment of cancers or neoplasms that include, but are not limited to, myelogenous leukemia, Hodgkin's disease, non-Hodgkin's lymphoma, lymphocyte leukemia, plasmacytomas, multiple myeloma, Burkitt's lymphoma, EBV-transformed diseases, hyperproliferative disorders Lymphoblastic Leukemia, Myeloid Leukemia, Adrenocortical Carcinoma, Hepatocellular Cancer, Liver Cancer, Soft Tissue Sarcoma, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Cerebellar Astrocytoma, Cerebral Astrocytoma, Cervical Cancer, Colon Cancer, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Breast Cancer, Gaucher's Disease, Gallbladder Cancer, Gastric Cancer, Gastrointestinal Carcinoid Tumor, Germ Cell Tumors, Gestational Trophoblastic Tumor, Hairy Cell Leukemia, Head and Neck Cancer, Hepatocellular Cancer, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Melanoma, Nasal Cavity and Paranasal Sinus Cancer, Nasopharyngeal Cancer, and any other hyperproliferative disease.

In certain embodiments, the methods provided herein are useful for treatment of heart diseases, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, postinfarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome; cardiovascular syphilis, and cardiovascular tuberculosis.

The methods provided in certain embodiment, are used for treatment of diseases and disorders of the respiratory system including, but are not limited to, nasal vestibulitis, nonallergic rhinitis (e.g., acute rhinitis, chronic rhinitis, atrophic rhinitis, vasomotor rhinitis), nasal polyps, and sinusitis, juvenile angiofibromas, cancer of the nose and juvenile papillomas, vocal cord polyps, nodules (singer's nodules), contact ulcers, vocal cord paralysis, laryngoceles, pharyngitis (e.g., viral and bacterial), tonsillitis, tonsillar cellulitis, parapharyngeal, abscess, laryngitis, laryngoceles, allergic disorders (eosinophilic pneumonia, hypersensitivity pneumonitis (e.g., extrinsic allergic alveolitis, allergic interstitial pneumonitis, organic dust pneumoconiosis, allergic bronchopulmonary aspergillosis, asthma, Wegener's granulomatosis (granulomatous vasculitis), Goodpasture's syndrome)), pneumonia (e.g., bacterial pneumonia (e.g., *Streptococcus pneumoniae* (pneumoncoccal pneumonia), *Staphylococcus aureus* (staphylococcal pneumonia), Gram-negative bacterial pneumonia (caused by, e.g., *Klebsiella* and *Pseudomonas* spp.), *Mycoplasma pneumoniae pneumonia, Hemophilus influenzae pneumonia, Legionella pneumophila* (Legionnaires' disease), and *Chlamydia psittaci* (Psittacosis)), and viral pneumonia (e.g., influenza, chickenpox (varicella), obstructive airway diseases (e.g., asthma, chronic obstructive pulmonary disease (COPD), emphysema, chronic or acute bronchitis), occupational lung diseases (e.g., silicosis, black lung (coal workers' pneumoconiosis), asbestosis, berylliosis, occupational asthmas, byssinosis, and benign pneumonioses), Infiltrative Lung Disease (e.g., pulmonary fibrosis (e.g., fibrosing alveolitis, usual interstitial pneumonia), idiopathic pulmonary fibrosis, desquamative interstitial pneumonia, lymphoid interstitial pneumonia, histiocytosis X (e.g., Letterer-Siwe disease, Hand-Schuller-Christian disease, eosinophilic granuloma), idiopathic pulmonary hemosiderosis, sarcoidosis and pulmonary alveolar proteinosis), Acute respiratory distress syndrome (also called, e.g., adult respiratory distress syndrome), edema, pulmonary embolism, bronchitis (e.g., viral, bacterial), bronchiectasis, atelectasis, lung abscess (caused by, e.g., *Staphylococcus aureus* or *Legionella pneumophila*), and cystic fibrosis.

In certain embodiments, the methods are for treatment of autoimmune disorders, such as systemic lupus erythematosus, rheumatoid arthritis, ankylosing spondylitis, multiple sclerosis, autoimmune thyroiditis, Hashimoto's thyroiditis, autoimmune hemolytic anemia, hemolytic anemia, thrombocytopenia, autoimmune thrombocytopenia purpura, autoimmune neonatal thrombocytopenia, idiopathic thrombocytopenia purpura, purpura (e.g., Henoch-Schönlein purpura), autoimmunocytopenia, Goodpasture's syndrome, myasthenia gravis, Grave's disease (hyperthyroidism), and diabetes mellitus. In certain embodiments, the methods are for treatment of diabetes.

In certain embodiments, the methods are for mucosal delivery of insulin to a subject in need thereof. In certain embodiments, the methods are for delivery of dietary supplements, including but not limited to vitamins, minerals, hormones and antioxidants. In certain embodiments, the methods provided herein are for delivery of vitamins. In other embodiments, the methods provided herein are for delivery of minerals. In other embodiments, the methods provided herein are for delivery of calcium. In other embodiments, the methods provided herein are for delivery of COQ10. In other embodiments, the methods provided herein are for delivery of testosterone.

F. Articles of Manufacture

The compositions provided herein can be packaged as articles of manufacture containing packaging material, a composition provided herein, and a label that indicates that the composition is for mucosal delivery. In instances where the active agent is useful for altering a body function or altering cosmetic appearance of the subject, the compositions can be packaged as articles of manufacture containing packaging material, a composition provided herein suitable for mucosal administration, and a label that indicates that the composition is used for altering a body function or altering cosmetic appearance of the subject. In certain embodiments, the compositions can be packaged as articles of manufacture containing packaging material, a composition provided herein suitable for mucosal administration, and a label that indicates that the composition is used for delivery of dietary supplements. In certain embodiments, the compositions can be packaged as articles of manufacture containing packaging material, a composition provided herein suitable for mucosal administration, and a label that indicates that the composition is used for delivering a therapeutic agent to a subject in need thereof.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, bottles, and any packaging material suitable for a selected formulation and intended mode of administration and treatment.

The following examples are exemplary only and are not intended to limit the scope of the subject matter claimed herein.

EXAMPLE 1

Preparation of Calcium Formulation:
Appropriate quantities of the raw materials were weighed for the 1.1 Kg batch as shown below:

| Ingredient (Oil) | mg/serving | %/serving | mg/batch |
|---|---|---|---|
| MCT (Neobee M-5)(in oil) | 1368.7 | 17.10875 | 171087.5 |
| Oat Oil (in oil) | 2046 | 25.575 | 255750 |
| Water | 2088.3 | 26.10375 | 261037.5 |
| Propylene Glycol (In Oil Phase) | 830 | 10.375 | 103750 |
| K-Sorbate (in oil) | 6 | 0.075 | 750 |
| Na-Benzoate (in oil) | 6 | 0.075 | 750 |
| Saladizer ® (In Water phase) | 8 | 0.1 | 1000 |
| Polymer (PEG 400 DS) (in oil) | 170 | 2.125 | 21250 |

-continued

| Ingredient (Oil) | mg/serving | %/serving | mg/batch |
|---|---|---|---|
| Methyl Paraben (in oil) | 3 | 0.0375 | 375 |
| Propyl Paraben (in oil) | 3 | 0.0375 | 375 |
| Lecithin (in oil) | 59 | 0.7375 | 7375 |
| Polysorbate 80 (In water Phase) | 300 | 3.75 | 37500 |
| Calcium Citrate, 17% Ca (168 mg of elemental Ca) | 820 | 10.25 | 102500 |
| Benzyl OH | 35 | 0.4375 | 4375 |
| Lactoferrin 94% (in water) | 50 | 0.625 | 6250 |
| Luo Han Gao 80% | 24 | 0.3 | 3000 |
| Sucralose | 59 | 0.7375 | 7375 |
| Butterscotch (BU-166) | 21 | 0.2625 | 2625 |
| Coconut (CC-116) | 24 | 0.3 | 3000 |
| Nat & Art. Vanilla (L-6729) | 22 | 0.275 | 2750 |
| Fudge (CT-151) | 20 | 0.25 | 2500 |
| Chocolate (CT-147) | 37 | 0.4625 | 4625 |
| Totals | 8000.000 | 100.0000 | 1100000 |

Water phase was prepared by weighing appropriate quantities of water, preservatives, polysorbate 80, lactoferrin, calcium, and Saladizer® gum blend, mixing the ingredients to dissolve all the components at 120° F.

Oil phase was prepared by weighing the appropriate amounts of oat oil, MCT, propylene glycol, methyl & propyl parabens, benzyl OH, PEG, and lecithin, heating the mixture to 120° F. and mixing until all the ingredients dissolve.

Emulsion was prepared by heating the water and oil phases to 160° F., and adding water phase to oil phase slowly while mixing. The emulsion was cooled to 95° F., followed by addition of flavors/sweeteners and additional water if needed to make up the batch of 1.1 Kg.

EXAMPLE 2

Preparation of Libido Formulation:
Appropriate quantities of the raw materials were weighed for the 0.55 Kg batch as shown below:

| Ingredient (Oil) | mg/serving | %/serving | mg/batch |
|---|---|---|---|
| MCT (Neobee M-5) (Oil Phase) | 308 | 30.8 | 154000 |
| Oat Oil (Oil Phase) | 150.2 | 15.02 | 75100 |
| Water | 231 | 23.1 | 115500 |
| Propylene Glycol (In Oil Phase) | 80 | 8 | 40000 |
| K-Sorbate (Preserves) (Water phase) | 2 | 0.2 | 1000 |
| Na-Benzoate (Preserves) (Water phase) | 2 | 0.2 | 1000 |
| Polymer (PEG 400 DS) (Oil Phase) | 20 | 2 | 10000 |
| Methyl Paraben (Oil Preserves) | 1 | 0.1 | 500 |
| Propyl Paraben (Oil Preserves) | 1 | 0.1 | 500 |
| Lecithin (Ultralec-P, Phospholipids) (Oil Phase) | 15 | 1.5 | 7500 |
| Polysorbate-80 (Lipids) (In water Phase, after filter after Salidizer) | 35 | 3.5 | 17500 |
| Benzyl OH (Sterilizer, protein preserver) (Oil Phase) | 5 | 0.5 | 2500 |
| Testosterone (in Oil, in liposome) | 75 | 7.5 | 37500 |
| Vinpocetine (in Oil, in liposome) | 6 | 0.6 | 3000 |
| (Lactoferrin 94% minimum) (Water phase) | 52 | 5.2 | 26000 |
| Sucralose (At the end) | 12 | 1.2 | 6000 |

-continued

| Ingredient (Oil) | mg/serving | %/serving | mg/batch |
| --- | --- | --- | --- |
| Nat. Banana (BA-133) (At the end) | 3.4 | 0.34 | 1700 |
| Nat & Art. Vanilla (VA-158) (At the end) | 1.4 | 0.14 | 700 |
| Totals | 1000.000 | 100.0000 | 550000 |

Water phase was prepared by weighing appropriate quantities of water, preservatives, polysorbate 80, and lactoferrin mixing the ingredients to dissolve all the components at 130-140° F.

Oil phase was prepared by weighing the appropriate amounts of oat oil, MCT, propylene glycol, methyl & propyl parabens, benzyl OH, lecithin, testosterone and vinpocetine and heating the mixture to 130-140° F. and mixing until all the ingredients dissolve.

Emulsion Phase was prepared by mixing the water and oil followed by cooling the emulsion.

EXAMPLE 3

Preparation of COQ10 Formulation:
Appropriate quantities of the raw materials were weighed for the 1.1 Kg batch as shown below:

| Ingredient (Oil) | mg/serving | %/serving | mg/batch |
| --- | --- | --- | --- |
| MCT (Neobee M-5) (Oil Phase) | 311 | 31.1 | 31100 |
| Oat Oil (Oil Phase) | 151 | 15.1 | 15100 |
| Water | 231 | 23.1 | 23100 |
| Propylene Glycol (In Oil Phase) | 83 | 8.3 | 8300 |
| K-Sorbate (Preserves) (Water phase) | 2 | 0.2 | 200 |
| Na-Benzoate (Preserves) (Water phase) | 2 | 0.2 | 200 |
| Polymer (PEG 400 DS) (Oil Phase) | 20 | 2 | 2000 |
| Methyl Paraben (Oil Preserves) | 1 | 0.1 | 100 |
| Propyl Paraben (Oil Preserves) | 1 | 0.1 | 100 |
| Lecithin (Ultralec-P, Phospholipids) (Oil Phase) | 15 | 1.5 | 1500 |
| Polysorbate-80 (Lipids) (In water Phase) | 36 | 3.6 | 3600 |
| Benzyl OH (Sterilizer, preservative) (Oil Phase) | 5 | 0.5 | 500 |
| COQ10 | 30 | 3 | 3000 |
| (Lactoferrin 94% minimum) (Water phase) | 100 | 10 | 10000 |
| Sucralose (At the end) | 3 | 0.3 | 300 |
| Nat. Banana (BA-133) (At the end) | 5 | 0.5 | 500 |
| Nat & Art. Vanilla (L-10181) (At the end) | 3 | 0.3 | 300 |
| Totals | 1000.000 | 100.0000 | 110000 |

Water phase was prepared by weighing appropriate quantities of water, preservatives, polysorbate 80, and lactoferrin mixing the ingredients to dissolve all the components at 98-100° F.

Oil phase was prepared by weighing the appropriate amounts of oat oil, MCT, propylene glycol, methyl & propyl parabens, benzyl OH, lecithin, and COQ10 and heating the mixture to 110° F. and mixing until all the ingredients dissolve.

Emulsion Phase was prepared by adding the oil and water phase followed by cooling the emulsion and addition of flavoring agents.

EXAMPLE 4

Preparation of Insulin Formulation:
Appropriate quantities of the raw materials were weighed for the 0.053 Kg batch as shown below:

| Ingredient (Oil) | mg/serving | %/serving | mg/batch |
| --- | --- | --- | --- |
| MCT (Neobee M-5) (Oil Phase) | 65 | 13.00001 | 6500 |
| Oat Oil (Oil Phase) | 39.9375 | 7.987506 | 3993.75 |
| Water (Water phase) | 162.559 | 32.511824 | 16255.9 |
| Propylene Glycol (In Oil Phase) | 53.25 | 10.650008 | 5325 |
| K-Sorbate (Preserves) (Water phase) | 0.665625 | 0.1331251 | 66.5625 |
| Na-Benzoate (Preserves) (Water phase) | 0.665625 | 0.1331251 | 66.5625 |
| Methyl Paraben (Oil Preservative) | 0.665625 | 0.1331251 | 66.5625 |
| Propyl Paraben (Oil Preservative) | 0.665625 | 0.1331251 | 66.5625 |
| LIPOID 100 S 100 (94% Phosphatidycholine (PC)) Powder | 48 | 9.6000072 | 4800 |
| Polysorbate-80 (Lipids) (In water Phase) | 66.5625 | 13.31251 | 6656.25 |
| Benzyl OH (Sterilizer, preservative) (Oil Phase) | 3.328125 | 0.6656255 | 332.8125 |
| Human Recombinant Insulin (Sigma Aldrich) | 5.1 | 1.0200008 | 510 |
| (Lactoferrin 94% minimum) (Water phase) | 47.5 | 9.5000071 | 4750 |
| Triethanolamine (TEA) Water Phase (add before Insulin) | 4 | 0.8000006 | 400 |
| Triethanolamine (TEA) Oil Phase | 2.1 | 0.4200003 | 210 |
| Totals | 500.000 | 100.0000 | 53177.16012 |

Water phase was prepared by weighing appropriate quantities of water, K-Sorbate, Na benzoate, Polysorbate-80 and triethanolamine was added and dissolved by mixing with a high speed mixer. The solution was maintained at pH 8.00-8.35 and temperature 115° F. Oil phase was prepared in a 600 mL Pyrex beaker. Appropriate quantities of oat oil, MCT, propylene glycol, methyl paraben, propyl paraben, Benzyl OH, Lipoid S 100 and triethanolamine were added and the mixture was heated up to 115° F. to dissolve the ingredients. Emulsion Phase was prepared by mixing the oil and water phase at 115° F., followed by cooling the emulsion and adding additional water to match the volume/weight to the total batch size. The emulsion was sheared at 2000 rpm at 115° F. until it began to thicken.

EXAMPLE 5

Preparation of Anti-Depression Formulation:
Appropriate quantities of the raw materials were weighed for the 1.1 Kg batch as shown below:

| Ingredient (Oil) | mg/serving | %/serving | mg/batch |
| --- | --- | --- | --- |
| MCT (Oil Phase) | 930 | 11.625 | 34875 |
| Oat Oil (Oil Phase) | 330 | 4.125 | 12375 |
| Water | 3967.2 | 49.59 | 148770 |
| Propylene Glycol (In Oil Phase) | 742.8 | 9.285 | 27855 |
| K-Sorbate | 6 | 0.075 | 225 |
| Na-Benzoate | 6 | 0.075 | 225 |

-continued

| Ingredient (Oil) | mg/serving | %/serving | mg/batch |
|---|---|---|---|
| Salidizer (In Oil Phase) | 15 | 0.1875 | 562.5 |
| Carmine Red (at the beginning) | 34 | 0.425 | 1275 |
| Polymer DS (PEG 400DS) | 170 | 2.125 | 6375 |
| Methyl Paraben (Oil Phase) | 3 | 0.0375 | 112.5 |
| Propyl Paraben (Oil Phase) | 3 | 0.0375 | 112.5 |
| Lecithin (Oil Phase) | 40 | 0.5 | 1500 |
| Span 60 (Oil Phase) | 40 | 0.5 | 1500 |
| PS-80 (In Oil) | 190 | 2.375 | 7125 |
| Phycamine | 850 | 10.625 | 31875 |
| Graviola (10:1) | 200 | 2.5 | 7500 |
| L-5-HTP | 150 | 1.875 | 5625 |
| Vinpocetine (Oil Phase) | 8 | 0.1 | 300 |
| Non-denatured whey protein powder | 50 | 0.625 | 1875 |
| BOH (Oil Phase) | 35 | 0.4375 | 1312.5 |
| Sucralose | 76 | 0.95 | 2850 |
| Nat Spearmint (MI-110) | 154 | 1.925 | 5775 |
| Totals | 8000.000 | 100.0000 | 330000 |

Water phase was prepared in a 600 mL Pyrex beaker. Appropriate amount of water, preservatives, color, L-5 HTP, phycomine, graviola (10:1) were added and dissolved by mixing with a slow speed mixer. Non-denatured whey protein was added and mixed while maintaining the temperature at 120° F. Oil phase was prepared in a 600 mL Pyrex beaker. Appropriate quantities of oils, propylene glycol, PS-80, methyl and propyl parabens, PEG, lecithin were added and mixed to dissolve the ingredients followed by addition of vinpocetine and Salidizer® at 120° F. Emulsion Phase was prepared by adding the oil and water phase at 120° F., followed by cooling the emulsion to 95° F. and adding flavoring agents.

EXAMPLE 6

Preparation of Non-Denatured Whey Protein Formulation:

Appropriate quantities of the raw materials were weighed for the 1.1 Kg batch as shown below:

| Ingredient (Oil) | mg/serving | %/serving | mg/batch |
|---|---|---|---|
| Water | 15409 | 51.36333333 | 564996.67 |
| Non-denatured whey protein | 11000 | 36.66666667 | 403333.33 |
| Na Benzoate | 78 | 0.26 | 2860 |
| K-Sorbate | 78 | 0.26 | 2860 |
| Antifoam | 322 | 1.073333333 | 11806.667 |
| Oat Oil | 965 | 3.216666667 | 35383.333 |
| Propylene Glycol | 285 | 0.95 | 10450 |
| Methyl Paraben | 30 | 0.1 | 1100 |
| Propyl Paraben | 30 | 0.1 | 1100 |
| PEG-400 | 628 | 2.093333333 | 23026.667 |
| Lecithin | 400 | 1.333333333 | 14666.667 |
| Span 60 | 69 | 0.23 | 2530 |
| Benzyl OH | 142 | 0.473333333 | 5206.6667 |
| PS-80 | 164 | 0.546666667 | 6013.3333 |
| Sucralose Powder | 97 | 0.323333333 | 3556.6667 |
| Nat. Fudge (CT-151) | 158 | 0.526666667 | 5793.3333 |
| Nat. Chocolate (CT-147) | 145 | 0.483333333 | 5316.6667 |
| Totals (+3.0% of Active) | 30000 | 100.0000 | 1100000 |

Water phase was prepared in a 1500 mL Pyrex beaker. Appropriate amounts of water, K-Sorbate, Na benzoate, Carmine red, and Polysorbate-80 were added and dissolved by mixing with a slow speed mixer. Non-denatured whey protein and anti-foam was mixed at pH 6.80 and a temperature of 115° F. Oil phase was prepared in a 600 mL Pyrex beaker. Appropriate quantities of oat oil, propylene glycol, PEG-400, methyl paraben, propyl paraben, lecithin, and span 60 were added and the mixture was heated up to 115° F. to dissolve the ingredients. Emulsion Phase was prepared by adding the oil and water phase at 115° F., followed by cooling the emulsion and adding flavoring agents.

In Examples 7-12, the amount of each ingredient needed to achieve the indicated amount/serving was calculated based on the specific gravity of the final composition.

EXAMPLE 7

Preparation of CoQ10 Formulation:

Appropriate quantities of the raw materials were weighed for the 1.3 Kg batch as shown below:

| Ingredient (Oil) | mg/serv. | Amount needed (mg) | %/serving | mg/batch |
|---|---|---|---|---|
| MCT (Neobee M-5) (Oil Phase) | 55 | 57.695 | 11.0000 | 144237.5 |
| Oat Oil (Oil Phase) | 39.9375 | 41.8944375 | 7.9875 | 104736.1 |
| Water (Water phase) | 155.909 | 163.548541 | 31.1818 | 408871.4 |
| Propylene Glycol (In Oil Phase) | 45 | 47.205 | 9.0000 | 118012.5 |
| K-Sorbate (Preserves) (Water phase) | 0.665625 | 0.69824063 | 0.1331 | 1745.602 |
| Na-Benzoate (Preserves) (Water phase) | 0.665625 | 0.69824063 | 0.1331 | 1745.602 |
| Methyl Paraben (Oil Preservative) | 0.665625 | 0.69824063 | 0.1331 | 1745.602 |
| Propyl Paraben (Oil Preservative) | 0.665625 | 0.69824063 | 0.1331 | 1745.602 |
| LIPOID 100 S 100 (94% Phosphatidycholine (PC)) Powder | 48 | 50.352 | 9.6000 | 125880 |
| Polysorbate-80 (Lipids) (In water Phase) | 66.5625 | 69.8240625 | 13.3125 | 174560.2 |
| Benzyl OH (Sterilizer, preservative) (Oil Phase) | 3.328125 | 3.49120313 | 0.6656 | 8728.008 |
| COQ10 (Oil Phase) | 30 | 31.47 | 6.0000 | 78675 |
| (Lactoferrin 94% minimum) (Water phase) | 47.5 | 49.8275 | 9.5000 | 124568.8 |
| Triethanolamine (TEA) Water Phase (add before Insulin) | 4 | 4.196 | 0.8000 | 10490 |
| Triethanolamine (TEA) Oil Phase | 2.1 | 2.2029 | 0.4200 | 5507.25 |
| Totals | 500.000 | 524.500 | 100.0000 | 1311249.0 |

-continued

| Procedure # | Phase | pH | Temp ° C. |
|---|---|---|---|
| Step (1) | PS-80/H20/TEA | 8.61 | 45.4 |
| Step (2) | PS-80/IGF-1 | 8.3 | 42.1 |
| Step (3) | PS-80/Lactof | 8.11 | 43.7 |
| Step (4) | Quality Control | 8.34 | 24.5 |

1. Oil Phase: Oil phase was prepared first as follows:

Equipment used: Corning Hot Plate, IKA mixer type RE16 S1 serial No 93-133-35, 600 mL Pyrex Beaker.

Ingredients were added in the following order: Oat Oil, MCT, propylene glycol, methyl and propyl parabens, benzyl OH and TEA. The mixture was heated to 115° F., and mixed at 250 rpm to dissolve the ingredients. Phosphatidylcholine (lipoid S 100) was added at 115° F. at 250 rpm and mixed to dissolve. CoQ10 was added to the mixture and dissolved to a light orange color.

2. Water Phase: Water phase was prepared as follows:

Equipment used: Corning Hot Plate, Arde Barinco Mixer Type 74D serial No L-1274, 1500 ml Pyrex Beaker, Hanna Instruments pH meter model HI 8314.

Ingredients were added in the following order: water, K-Sorbate, Na Benzoate, Polysorbate 80, and TEA. The pH was maintained at >8.30. Solution was heated slowly and stirred with a stirring rod until all the PS-80 was dissolved into the solution (straw yellow color). Temperature was maintained at 115° F. and pH at above 8.30, adjusting with TEA as needed. Lactoferrin was added to the straw-yellow solution while mixing with the Arde Barinco Mixer at 10% RPM on Forward. Temperature was maintained at 115° F. and the mixer at 10% of RPM until a good dispersion was observed. Antifoam was added as needed. All lactoferrin was dissolved until there were no clumps in the solution.

3. Emulsion Phase: Emulsion phase was prepared as follows:

Equipment used: Arde Barinco Mixer Type 74D serial No L-1274

Oil phase was added to water phase (each at 115° F.) at 14% of RPM for 10 minutes while cooling. After 10 minutes, the mixing speed was lowered to 10% RPM. Mixing was continued with Arde Barinco mixer while maintaining enough shear for the emulsion and the mixture was cooled during the process.

4. Finished product: The finished product had a pH above 8.00 and was tested for amount of CoQ10 present.

EXAMPLE 8

Preparation of Oratropin-1 Formulation:

Appropriate quantities of the raw materials were weighed for the 1.3 Kg batch as shown below:

| Ingredient (Oil) | mg/serv. | Amount needed (mg) | %/serving | mg/batch |
|---|---|---|---|---|
| MCT (Neobee M-5) (Oil Phase) | 65 | 68.185 | 13.0000 | 170462.5 |
| Oat Oil (Oil Phase) | 39.9375 | 41.8944375 | 7.9875 | 104736.1 |
| Water (Water phase) | 167.619 | 175.832331 | 33.5238 | 439580.8 |
| Propylene Glycol (In Oil Phase) | 53.25 | 55.85925 | 10.6500 | 139648.1 |
| K-Sorbate (Preserves) (Water phase) | 0.665625 | 0.69824063 | 0.1331 | 1745.602 |
| Na-Benzoate (Preserves) (Water phase) | 0.665625 | 0.69824063 | 0.1331 | 1745.602 |
| Methyl Paraben (Oil Preservative) | 0.665625 | 0.69824063 | 0.1331 | 1745.602 |
| Propyl Paraben (Oil Preservative) | 0.665625 | 0.69824063 | 0.1331 | 1745.602 |
| LIPOID 100 S 100 (94% Phosphatidycholine (PC)) Powder | 48 | 50.352 | 9.6000 | 125880 |
| Polysorbate-80 (Lipids) (In water Phase) | 66.5625 | 69.8240625 | 13.3125 | 174560.2 |
| Benzyl OH (Sterilizer, preservative) (Oil Phase) | 3.328125 | 3.49120313 | 0.6656 | 8728.008 |
| IGF-1 | 0.04 | 0.04196 | 0.0080 | 104.9 |
| (Lactoferrin 94% minimum) (Water phase) | 47.5 | 49.8275 | 9.5000 | 124568.8 |
| Triethanolamine (TEA) Water Phase (add before Insulin) | 4 | 4.196 | 0.8000 | 10490 |
| Triethanolamine (TEA) Oil Phase | 2.1 | 2.2029 | 0.4200 | 5507.25 |
| Totals | 500.000 | 524.500 | 100.0000 | 1311249.0 |

| Procedure # | Phase | pH | Temp ° C. |
|---|---|---|---|
| Step (1) | PS-80/H20/TEA | 8.61 | 45.4 |
| Step (2) | PS-80/IGF-1 | 8.3 | 42.1 |
| Step (3) | PS-80/Lactof | 8.11 | 43.7 |
| Step (4) | Quality Control | 8.34 | 24.5 |

1. Oil Phase: Oil phase was prepared first as follows:

Equipment used: Corning Hot Plate, IKA mixer type RE16 S1 serial No 93-133-35, 600 ml Pyrex Beaker.

Ingredients were added in the following order: Oat Oil, MCT, propylene glycol, methyl and propyl parabens, benzyl OH and TEA. The mixture was heated to 115° F., and mixed at 250 RPM to dissolve the ingredients. Phosphatidylcholine (lipoid S 100) was added at 115° F. at 250 RPM and mixed to dissolve.

2. Water Phase: Water phase was prepared as follows:

Equipment used: Corning Hot Plate, Arde Barinco Mixer Type 74D serial No L-1274, 1500 ml Pyrex Beaker, Hanna Instruments pH meter model HI 8314.

Ingredients were added in the following order: water, K-Sorbate, Na Benzoate, Polysorbate 80, and TEA. The pH was maintained at >8.30. Solution was heated slowly and stirred with a stirring rod until all the PS-80 was dissolved into the solution (straw yellow color). Temperature was maintained at 115° F. pH was maintained at above 8.30, adjusting with TEA as needed. IGF-1 was added to the straw-yellow solution, while maintaining temperature at 115° F. and pH at 8.30. Lactoferrin was added with the Arde Barinco Mixer at 10% RPM on Forward. Temperature was maintained at 115° F. and the mixer at 10% of RPM until a good dispersion was observed. Antifoam was added as needed. All lactoferrin was dissolved so that the solution did not contain any lumps.

3. Emulsion Phase: Emulsion phase was prepared as follows:

Equipment used: Arde Barinco Mixer Type 74D serial No L-1274

Oil phase was added to water phase (each at 115° F.) at 14% of RPM for 10 minutes while cooling. After 10 minutes the mixing speed was lowered to 10% RPM. Mixing was continued with Arde Barinco mixer while maintaining enough shear for the emulsion and the mixture was cooled during the process.

4. Finished product: The finished product had a pH above 8.00 and was tested for the amount of IGF-1.

EXAMPLE 9

Preparation of Hexatropin-6 Formulation:

Appropriate quantities of the raw materials were weighed for the 1.3 Kg batch as shown below:

1. Oil phase: Oil phase was prepared first as follows:

Equipment used: Corning Hot Plate, IKA mixer type RE16 S1 serial No 93-133-35, 600 ml Pyrex Beaker Ingredients were added in the following order: Oat Oil, MCT, propylene glycol, methyl and propyl parabens, benzyl OH and TEA. The mixture was heated to 115° F., and mixed at 250 RPM to dissolve the ingredients. Phosphatidylcholine (lipoid S 100) was added at 115° F. at 250 RPM and mixed to dissolve.

2. Water Phase: Water phase was prepared as follows:

Equipment used: Corning Hot Plate, Arde Barinco Mixer-Type 74D serial No L-1274, 1500 ml Pyrex Beaker, Hanna Instruments pH meter model HI 8314.

Ingredients were added in the following order: water, K-Sorbate, Na Benzoate, Polysorbate 80 (PS-80), and TEA. The pH was maintained at >8.30. Solution was heated slowly and stirred with a stirring rod until all the PS-80 was dissolved into the solution (straw yellow color). Temperature was maintained at 115° F. and pH at above 8.30, adjusting with TEA as needed. Hexarelin & GHRP-6 agonist were added at 115° F. pH was maintained at above 8.30. Lactoferrin was added to the solution while mixing with the Arde Barinco Mixer at 10% RPM on Forward. Temperature was maintained at 115° F. and the mixer at 10% of RPM until a good dispersion was observed. Antifoam was added as needed. All lactoferrin was dissolved until there were no clumps in the solution.

3. Emulsion Phase: Emulsion phase was prepared as follows:

Equipment used: Arde Barinco Mixer Type 74D serial No L-1274

Oil phase was added to water phase (each at 115° F.) at 14% of RPM for 10 minutes while cooling. After 10 minutes the mixing speed was lowered to 10% RPM. Mixing was continued with Arde Barinco mixer while maintaining enough shear for the emulsion and the mixture was cooled during the process.

| Ingredient (Oil) | mg/serv. | Amount needed (mg) | %/serving | mg/batch |
|---|---|---|---|---|
| MCT (Neobee M-5) (Oil Phase) | 65 | 68.185 | 13.0000 | 170462.5 |
| Oat Oil (Oil Phase) | 39.9375 | 41.8944375 | 7.9875 | 104736.1 |
| Water (Water phase) | 167.459 | 175.664491 | 33.4918 | 439161.2 |
| Propylene Glycol (In Oil Phase) | 53.25 | 55.85925 | 10.6500 | 139648.1 |
| K-Sorbate (Preserves) (Water phase) | 0.665625 | 0.69824063 | 0.1331 | 1745.602 |
| Na-Benzoate (Preserves) (Water phase) | 0.665625 | 0.69824063 | 0.1331 | 1745.602 |
| Methyl Paraben (Oil Preservative) | 0.665625 | 0.69824063 | 0.1331 | 1745.602 |
| Propyl Paraben (Oil Preservative) | 0.665625 | 0.69824063 | 0.1331 | 1745.602 |
| LIPOID 100 S 100 (94% Phosphatidycholine (PC)) Powder | 48 | 50.352 | 9.6000 | 125880 |
| Polysorbate-80 (Lipids) (In water Phase) | 66.5625 | 69.8240625 | 13.3125 | 174560.2 |
| Benzyl OH (Sterilizer, preservative) (Oil Phase) | 3.328125 | 3.49120313 | 0.6656 | 8728.008 |
| Hexarelin | 0.1 | 0.1049 | 0.0200 | 262.25 |
| GHRP-6 (Growth Hormone Peptide-6) Agonist | 0.1 | 0.1049 | 0.0200 | 262.25 |
| (Lactoferrin 94% minimum) (Water phase) | 47.5 | 49.8275 | 9.5000 | 124568.8 |
| Triethanolamine (TEA) Water Phase (add before Insulin) | 4 | 4.196 | 0.8000 | 10490 |
| Triethanolamine (TEA) Oil Phase | 2.1 | 2.2029 | 0.4200 | 5507.25 |
| Totals | 500.000 | 524.500 | 100.0000 | 1311249.0 |

| Procedure # | Phase | pH | Temp ° C. |
|---|---|---|---|
| Step (1) | PS-80/H20/TEA | 8.61 | 45.4 |
| Step (2) | PS-80/Hex/GHRP-6 | 8.3 | 42.1 |
| Step (3) | PS-80/Lactof | 8.11 | 43.7 |
| Step (4) | Quality Control | 8.34 | 24.5 |

4. Finished product: The finished product has a pH above 8.00 was tested for contents of GHRP-6 agonist and Hexarelin.

EXAMPLE 10

Preparation of Insulin-Albumin Formulation:
Appropriate quantities of the raw materials were weighed for the 0.11 Kg batch as shown below:

| Ingredients | Mg/serv. | Amount needed (mg) | %/serving | mg/batch |
|---|---|---|---|---|
| MCT (Neobee M-5) (Oil Phase) | 65 | 68.185 | 13.0046 | 13637 |
| Oat Oil (Oil Phase) | 39.9375 | 41.8944375 | 7.9903 | 8378.8875 |
| Water (Water phase) | 150.597 | 157.976253 | 30.1300 | 31595.2506 |
| Propylene Glycol (In Oil Phase) | 53.25 | 55.85925 | 10.6538 | 11171.85 |
| K-Sorbate (Preserves) (Water phase) | 0.665625 | 0.698240625 | 0.1332 | 139.648125 |
| Na-Benzoate (Preserves) (Water phase) | 0.665625 | 0.698240625 | 0.1332 | 139.648125 |
| Methyl Paraben (Oil Preservative) | 0.665625 | 0.698240625 | 0.1332 | 139.648125 |
| Propyl Paraben (Oil Preservative) | 0.665625 | 0.698240625 | 0.1332 | 139.648125 |
| LIPOID 100 S 100 (94% Phosphatidycholine (PC)) Powder | 48 | 50.352 | 9.6034 | 10070.4 |
| Polysorbate-80 (Lipids) (In water Phase) | 66.5625 | 69.8240625 | 13.3172 | 13964.8125 |
| Benzyl OH (Sterilizer, preservative) (Oil Phase) | 3.328125 | 3.491203125 | 0.6659 | 698.240625 |
| Human Recombinant Insulin (Sigma Aldrich) | 10 | 11 | 2.0980 | 2200 |
| (Albumin) (Water phase) | 47.5 | 49.8275 | 9.5033 | 9965.5 |
| Triethanolamine (TEA) Water Phase (add before Insulin) | 10.4 | 10.9096 | 2.0807 | 2181.92 |
| Triethanolamine (TEA) Oil Phase | 2.1 | 2.2029 | 0.4201 | 440.58 |
| Totals | 499.338 | 524.315 | 100.0000 | 104863.0337 |

| Procedure | Phase | pH | Temp ° C. |
|---|---|---|---|
| Step (1) | PS-80/H20/TEA | 8.61 | 45.4 |
| Step (2) | PS-80/Insulin | 8.3 | 42.1 |
| Step (3) | PS-80/Albumin | 8.27 | 43.7 |
| Step (4) | Finished Product | 8.42 | 13.6 |

1. Oil phase: Oil phase was prepared first as follows:
Equipment used: Corning Hot Plate, IKA mixer type RE16 S1 serial No 93-133-35, 80 ml Pyrex Beaker.
Ingredients were added in the following order: Oat Oil, MCT, propylene glycol, methyl and propyl parabens, benzyl OH and TEA. The mixture was heated to 115° F., and mixed at 250 RPM to dissolve the ingredients. Phosphatidylcholine (lipoid S 100) was added at 115° F. at 250 RPM and mixed to dissolve. COQ10 was added to the mixture and dissolved to a light orange color.

2. Water Phase: Water phase was prepared as follows:
Equipment used: Corning Hot Plate, Arde Barinco Mixer Type 74D serial No L-1274, 250 ml Pyrex Beaker, Hanna Instruments pH meter model HI 8314.
Ingredients were added in the following order: water, K-Sorbate, Na Benzoate, Polysorbate 80, and TEA. The pH was maintained at >8.30. Solution was heated slowly and stirred with a stirring rod until all the PS-80 was dissolved into the solution (straw yellow color). Temperature was maintained at 115° F. and pH at above 8.30, adjusting with TEA as needed. Insulin was added to the straw-yellow solution, while maintaining temperature at 115° F. and pH at 8.30. Albumin was added with the Arde Barinco Mixer at 10% RPM on Forward. Temperature was maintained at 115° F. and the mixer at 10% of RPM until a good dispersion was observed. Antifoam was added as needed. All lactoferrin was dissolved so that the solution did not contain any lumps.

3. Emulsion phase: Emulsion phase was prepared as follows:
Equipment used: Arde Barinco Mixer Type 74D serial No L-1274
Oil phase was added to water phase (each at 115° F.) at 14% of RPM for 10 minutes while cooling. After 10 minutes the mixing speed was lowered to 10% RPM. Mixing was continued with Arde Barinco mixer while maintaining enough shear for the emulsion and the mixture was cooled during the process.

4. Finished product: The finished product had a pH above 8.00 and was tested for the amount of insulin.

EXAMPLE 11

Preparation of Insulin-Lactoferrin Formulation:
Appropriate quantities of the raw materials were weighed for the 0.53 Kg batch as shown below:

| Ingredients | mg/serv. | Amount needed | %/serving | mg/batch |
|---|---|---|---|---|
| MCT (Neobee M-5) (Oil Phase) | 65 | 68.185 | 12.9865 | 68185 |
| Oat Oil (Oil Phase) | 39.9375 | 41.8944375 | 7.9792 | 41894.4375 |
| Water (Water phase) | 150.597 | 157.976253 | 30.0882 | 157976.253 |
| Propylene Glycol (In Oil Phase) | 53.25 | 55.85925 | 10.6390 | 55859.25 |
| K-Sorbate (Preserves) (Water phase) | 0.665625 | 0.698240625 | 0.1330 | 698.240625 |

-continued

| | | | | |
|---|---|---|---|---|
| Na-Benzoate (Preserves) (Water phase) | 0.665625 | 0.698240625 | 0.1330 | 698.240625 |
| Methyl Paraben (Oil Preservative) | 0.665625 | 0.698240625 | 0.1330 | 698.240625 |
| Propyl Paraben (Oil Preservative) | 0.665625 | 0.698240625 | 0.1330 | 698.240625 |
| LIPOID 100 S 100 (94% Phosphatidycholine (PC)) Powder | 48 | 50.352 | 9.5901 | 50352 |
| Polysorbate-80 (Lipids) (In water Phase) | 66.5625 | 69.8240625 | 13.2987 | 69824.0625 |
| Benzyl OH (Sterilizer, preservative) (Oil Phase) | 3.328125 | 3.491203125 | 0.6649 | 3491.203125 |
| Human Recombinant Insulin (Sigma Aldrich) | 10.662117 | 11.72832925 | 2.2338 | 11728.32925 |
| (Lactoferrin 94% minimum "transferring") (Water phase) | 47.5 | 49.8275 | 9.4902 | 49827.5 |
| Triethanolamine (TEA) Water Phase (add before Insulin) | 10.4 | 10.9096 | 2.0778 | 10909.6 |
| Triethanolamine (TEA) Oil Phase | 2.1 | 2.2029 | 0.4196 | 2202.9 |
| Totals | 500.000 | 525.043 | 100.0000 | 525043.4979 |

| Procedure # | Phase | pH | Temp ° C. |
|---|---|---|---|
| Step (1) | PS-80/H20/TEA | 8.61 | 45.4 |
| Step (2) | PS-80/Insulin | 8.3 | 42.1 |
| Step (3) | PS-80/Lactof | 8.27 | 43.7 |
| Step (4) | Finished Product | 8.42 | 13.6 |

1. Oil Phase: Oil phase was prepared first as follows:
    Equipment used: Corning Hot Plate, IKA mixer type RE16 S1 serial No 93-133-35, 250 ml Pyrex Beaker
    Ingredients were added in the following order: Oat Oil, MCT, propylene glycol, methyl and propyl parabens, benzyl OH and TEA. The mixture was heated to 115° F., and mixed at 250 RPM to dissolve the ingredients. Phosphatidylcholine (lipoid S 100) was added at 115° F. at 250 RPM and mixed to dissolve.
2. Water Phase: Water phase was prepared as follows:
    Equipment used: Corning Hot Plate, Arde Barinco Mixer Type 74D serial No L-1274, 600 ml Pyrex Beaker, Hanna Instruments pH meter model HI 8314
    Ingredients were added in the following order: water, K-Sorbate, Na Benzoate, Polysorbate 80, and TEA. The pH was maintained at >8.30. Solution was heated slowly and stirred with a stirring rod until all the PS-80 was dissolved into the solution (straw yellow color). Temperature was maintained at 115° F. and pH at above 8.30, adjusting with TEA as needed. Insulin was added to the straw-yellow solution, while maintaining temperature at 115° F. and pH at 8.30. Lactoferrin was added with the Arde Barinco Mixer at 10% RPM on Forward. Temperature was maintained at 115° F. and the mixer at 10% of RPM until a good dispersion was observed. Antifoam was added as needed. All lactoferrin was dissolved so that the solution did not contain any lumps.
3. Emulsion Phase: Emulsion phase was prepared as follows:
    Equipment used: Arde Barinco Mixer Type 74D serial No L-1274
    Oil phase was added to the water phase (each at 115° F.) at 14% of RPM for 10 minutes while cooling. After 10 minutes the mixing speed was lowered to 10% RPM. Mixing was continued with Arde Barinco mixer while maintaining enough shear for the emulsion and the mixture was cooled during the process.
4. Finished product: The finished product had a pH above 8.00 and was tested for the amount of insulin.

EXAMPLE 12

Preparation of Insulin-Lactoferrin Formulation:
    Appropriate quantities of the raw materials were weighed for the 0.65 Kg batch as shown below:

| Ingredients | mg/serv. | Amount needed | %/serving | mg/batch |
|---|---|---|---|---|
| MCT (Neobee M-5) (Oil Phase) | 65 | 84.5 | 13.0428 | 84500 |
| Oat Oil (Oil Phase) | 39.9375 | 51.91875 | 8.0138 | 51918.75 |
| Water (Water phase) | 150.597 | 195.7761 | 30.2186 | 195776.1 |
| Propylene Glycol (In Oil Phase) | 53.25 | 69.225 | 10.6851 | 69225 |
| K-Sorbate (Preserves) (Water phase) | 0.665625 | 0.8653125 | 0.1336 | 865.3125 |
| Na-Benzoate (Preserves) (Water phase) | 0.665625 | 0.8653125 | 0.1336 | 865.3125 |
| Methyl Paraben (Oil Preservative) | 0.665625 | 0.8653125 | 0.1336 | 865.3125 |
| Propyl Paraben (Oil Preservative) | 0.665625 | 0.8653125 | 0.1336 | 865.3125 |
| LIPOID 100 S 100 (94% Phosphatidycholine (PC)) Powder | 48 | 62.4 | 9.6316 | 62400 |
| Polysorbate-80 (Lipids) (In water Phase) | 66.5625 | 86.53125 | 13.3563 | 86531.25 |
| Benzyl OH (Sterilizer, preservative) (Oil Phase) | 3.328125 | 4.3265625 | 0.6678 | 4326.5625 |
| Human Recombinant Insulin (Sigma Aldrich) | 10.662117 | 11.72832925 | 1.8103 | 11728.32925 |
| (Lactoferrin 94% minimum "transferring") (Water phase) | 47.5 | 61.75 | 9.5313 | 61750 |

| | -continued | | | |
|---|---|---|---|---|
| Triethanolamine (TEA) Water Phase (add before Insulin) | 10.4 | 13.52 | 2.0868 | 13520 |
| Triethanolamine (TEA) Oil Phase | 2.1 | 2.73 | 0.4214 | 2730 |
| Totals | | 500.000 | 647.867 | 100.0000 | 647867.2417 |

| Procedure # | Phase | pH | Temp ° C. |
|---|---|---|---|
| Step (1) | PS-80/H20/TEA | 8.61 | 45.4 |
| Step (2) | PS-80/Insulin | 8.3 | 42.1 |
| Step (3) | PS-80/Lactof | 8.27 | 43.7 |
| Step (4) | Finished Product | 8.42 | 13.6 |

1. Oil Phase: Oil phase was prepared first as follows:

Equipment used: Corning Hot Plate, IKA mixer type RE16 S1 serial No 93-133-35, 600 ml Pyrex Beaker Ingredients were added in the following order: Oat Oil, MCT, propylene glycol, methyl and propyl parabens, benzyl OH and TEA. The mixture was heated to 115° F., and mixed at 250 RPM to dissolve the ingredients. Phosphatidylcholine (lipoid S 100) was added at 115° F. at 250 RPM and mixed to dissolve.

2. Water Phase: Water phase was prepared as follows:

Equipment used: Corning Hot Plate, Arde Barinco Mixer Type 74D serial No L-1274, 250 ml Pyrex Beaker, Hanna Instruments pH meter model HI 8314

Ingredients were added in the following order: water, K-Sorbate, Na Benzoate, Polysorbate 80, and TEA. The pH was maintained at >8.30. Solution was heated slowly and stirred with a stirring rod until all the PS-80 was dissolved into the solution (straw yellow color). Temperature was maintained at 115° F. and pH at above 8.30, adjusting with TEA as needed. Insulin was added to the straw-yellow solution, while maintaining temperature at 115° F. and pH at 8.30. Lactoferrin was added while mixing the solution with the Arde Barinco Mixer at 10% RPM on Forward. Temperature was maintained at 115° F. and the mixer at 10% of RPM until a good dispersion was observed. Antifoam was added as needed. All lactoferrin was dissolved so that the solution did not contain any lumps.

3. Emulsion Phase: Emulsion phase was prepared as follows:

Equipment used: Arde Barinco Mixer Type 74D serial No L-1274

Oil phase was added to water phase (each at 115° F.) at 14% of RPM for 10 minutes while cooling. After 10 minutes the mixing speed was lowered to 10% RPM. Mixing was continued with Arde Barinco mixer while maintaining enough shear for the emulsion and the mixture was cooled during the process.

4. Finished product: The finished product had a pH above 8.00 and was tested for the amount of insulin.

EXAMPLE 13

Preparation of Insulin-Immunoglobulin Formulation:

Appropriate quantities of the raw materials were weighed for the 0.11 Kg batch as shown below:

| Ingredients | mg/serv. | Amount needed | %/serving | mg/batch |
|---|---|---|---|---|
| MCT (Neobee M-5) (Oil Phase) | 65 | 68.185 | 13.0046 | 13637 |
| Oat Oil (Oil Phase) | 39.9375 | 41.8944375 | 7.9903 | 8378.8875 |
| Water (Water phase) | 150.597 | 157.976253 | 30.1300 | 31595.2506 |
| Propylene Glycol (In Oil Phase) | 53.25 | 55.85925 | 10.6538 | 11171.85 |
| K-Sorbate (Preservs) (Water phase) | 0.665625 | 0.698240625 | 0.1332 | 139.648125 |
| Na-Benzoate (Preservs) (Water phase) | 0.665625 | 0.698240625 | 0.1332 | 139.648125 |
| Methyl Paraben (Oil Preservative) | 0.665625 | 0.698240625 | 0.1332 | 139.648125 |
| Propyl Paraben (Oil Preservative) | 0.665625 | 0.698240625 | 0.1332 | 139.648125 |
| LIPOID 100 S 100 (94% Phosphatidycholine (PC)) Powder | 48 | 50.352 | 9.6034 | 10070.4 |
| Polysorbate-80 (Lipids) (In water Phase) | 66.5625 | 69.8240625 | 13.3172 | 13964.8125 |
| Benzyl OH (Sterilizer, preservatizer) (Oil Phase) | 3.328125 | 3.491203125 | 0.6659 | 698.240625 |
| Human Recombinant Insulin (Sigma Aldrich) | 10 | 11 | 2.0980 | 2200 |
| IGG (Immunoglobulin) (Water phase) | 47.5 | 49.8275 | 9.5033 | 9965.5 |
| Triethanolamine (TEA) Water Phase (add before Insulin) | 10.4 | 10.9096 | 2.0807 | 2181.92 |
| Triethanolamine (TEA) Oil Phase | 2.1 | 2.2029 | 0.4201 | 440.58 |
| Totals | 499.338 | 524.315 | 100.0000 | 104863.0337 |

| Procedure # | Phase | pH | Temp ° C. |
|---|---|---|---|
| Step (1) | PS-80/H20/TEA | 8.61 | 45.4 |
| Step (2) | PS-80/Insulin | 8.3 | 42.1 |
| Step (3) | PS-80/IGG | 8.27 | 43.7 |
| Step (4) | Finished Product | 8.42 | 13.6 |

1. Oil Phase: Oil phase was prepared first as follows:

Equipment used: Corning Hot Plate, IKA mixer type RE 16 S1 serial No 93-133-35, 80 ml Pyrex Beaker.

Ingredients were added in the following order: Oat Oil, MCT, propylene glycol, methyl and propyl parabens, benzyl OH and TEA. The mixture was heated to 115° F., and mixed at 250 RPM to dissolve the ingredients. Phosphatidylcholine (lipoid S 100) was added at 115° F. at 250 RPM and mixed to dissolve.

2. Water Phase: Water phase was prepared as follows:
Equipment used: Corning Hot Plate, Arde Barinco Mixer Type 74D serial No L-1274, 250 ml Pyrex Beaker, Hanna Instruments pH meter model HI 8314.

Ingredients were added in the following order: water, K-Sorbate, Na Benzoate, Polysorbate 80, and TEA. The pH was maintained at >8.30. Solution was heated slowly and stirred with a stirring rod until all the PS-80 was dissolved into the solution (straw yellow color). Temperature was maintained at 115° F. and pH at above 8.30, adjusting with TEA as needed. Insulin was added to the straw-yellow solution, while maintaining temperature at 115° F. and pH at 8.30. Immunoglobulin was added with the Arde Barinco Mixer at 10% RPM on Forward. Temperature was maintained at 115° F. and the mixer at 10% of RPM until a good dispersion was observed. Antifoam was added as needed. All immunoglobulin was dissolved so that the solution did not contain any lumps.

3. Emulsion Phase: Emulsion phase was prepared as follows:
Equipment used: Arde Barinco Mixer Type 74D serial No L-1274

Oil phase was added to water phase (each at 115° F.) at 14% of RPM for 10 minutes while cooling. After 10 minutes the mixing speed was lowered to 10% RPM. Mixing was continued with Arde Barinco mixer while maintaining enough shear for the emulsion and the mixture was cooled during the process.

4. Finished product: The finished product had a pH above 8.00 and was tested for the amount of insulin.

EXAMPLE 14

Oral Bioavailability and Pharmacokinetic Studies in Dogs

Oral bioavailability of insulin composition was determined using an IV study followed by an oral crossover study and the relative areas of under the curve, plasma half life, $C_{max}$, and $T_{max}$ was calculated.

Protocol Outline

Mongrel dogs (20-30 kg) were used (n=2) for the study. The dogs were fasted overnight for both the studies in order to achieve baseline glucose and insulin levels.

IV Study: IV injection of 0.01 mg/kg human insulin was administered to the dogs. Blood samples were taken at: 2, 5, 10, 15, 20, 25, 40, 60, 120, 180, and 240 minutes. Blood was analyzed for glucose and insulin levels for all time points.

Oral Study: 4 days were allowed for washout following the IV study. Insulin composition of Example 12 was orally administered between lips and gums at a dose of 0.02 mg/kg. Blood samples were taken at 5, 5.5, 6.5, 7, 7.5, 8, 8.5, 9, 9.5, 10, 10.5, 11, 11.5, 12, 16, and 24 hours and analyzed for insulin and glucose levels.

Following data collection, plasma concentration, plasma half-life, peak concentration ($C_{max}$) and time to reach $C_{max}$ ($t_{max}$) were determined. From the areas under the curve, percent oral bioavailability was determined.

TABLE 1

DOG #71, Weight of dog = 22 kg,
IV dosing: DOSE = 0.01 mg/kg

| Time (min) | Plasma Insulin (ng/mL) | Plasma Glucose (mg/dL) |
| --- | --- | --- |
| 2 | 50.2 | 89 |
| 5 | 26.6 | 82 |
| 10 | 15.9 | 57 |
| 15 | 10.1 | 46 |

TABLE 1-continued

DOG #71, Weight of dog = 22 kg,
IV dosing: DOSE = 0.01 mg/kg

| Time (min) | Plasma Insulin (ng/mL) | Plasma Glucose (mg/dL) |
| --- | --- | --- |
| 20 | 7.6 | 41 |
| 25 | 5.9 | 42 |
| 40 | 2.5 | 39 |
| 60 | 1.2 | 48 |
| 120 | 0.19 | 69 |
| 180 | 0.08 | 87 |
| 240 | 0.08 | 86 |

TABLE 2

DOG 71, Weight of dog = 22 kg
P.O dosing: DOSE = 0.02 mg/kg

| Time (h) | Plasma Insulin ng/mL | Plasma Glucose |
| --- | --- | --- |
| 5 | 0.17 | 80 |
| 5.5 | 0.02 | 76 |
| 6 | 0 | 79 |
| 6.5 | 0.06 | 86 |
| 7 | 0.2 | 84 |
| 7.5 | 0.1 | 85 |
| 8 | 0.46 | 85 |
| 8.5 | 0.23 | 85 |
| 9 | 0.13 | 84 |
| 9.5 | 0.45 | 85 |
| 10 | 1.1 | 88 |
| 10.5 | 0.42 | 99 |
| 11 | 0.68 | 88 |
| 11.5 | 0.68 | 100 |
| 12 | 0.38 | 82 |
| 16 | 0.55 | 85 |
| 24 | 0.5 | 87 |

TABLE 3

DOG #72, Weight of dog = 28 kg,
IV dosing: DOSE = 0.01 mg/kg

| Time (min) | Plasma Insulin (ng/mL) | Plasma Glucose (mg/dL) |
| --- | --- | --- |
| 2 | 27.3 | 89 |
| 5 | 21.4 | 60 |
| 10 | 11.4 | 31 |
| 15 | 6.5 | 28 |
| 20 | 3.4 | 35 |
| 25 | 2.7 | 24 |
| 40 | 0.7 | 21 |
| 60 | 0.2 | 33 |
| 120 | 0.04 | 68 |
| 180 | 0 | 102 |
| 240 | 0.04 | 99 |

TABLE 4

DOG #72, Weight of dog = 28 kg, P.O. dosing: DOSE = 0.02 mg/kg

| Time (h) | Plasma Insulin (ng/mL) | Plasma Glucose (mg/dL) |
| --- | --- | --- |
| 5 | 0.17 | 82 |
| 5.5 | 0.02 | 97 |
| 6 | 0 | 89 |
| 6.5 | 0.06 | 90 |
| 7 | 0.2 | 84 |
| 7.5 | 0.1 | 89 |

TABLE 4-continued

DOG #72, Weight of dog = 28 kg, P.O. dosing: DOSE = 0.02 mg/kg

| Time (h) | Plasma Insulin (ng/mL) | Plasma Glucose (mg/dL) |
|---|---|---|
| 8 | 0.46 | 93 |
| 8.5 | 0.23 | 103 |
| 9 | 0.13 | 93 |
| 9.5 | 0.45 | 101 |
| 10 | 0.28 | 95 |
| 10.5 | 1.1 | 88 |
| 11 | 0.42 | 95 |
| 11.5 | 0.68 | 88 |
| 12 | 0.38 | 91 |
| 16 | 0.55 | 103 |
| 24 | 0.50 | 92 |

TABLE 5

PHARMACOKINETIC ANALYSIS FOR ORAL INSULIN IN DOGS
Miprocelle-Insulin
Analytical Range 0.01-3000/mL
TTI RFA: 3021
PO Dose 0.02 mg/kg

| Time (hr) | Animal #/Concentration 71 | 72 | Mean |
|---|---|---|---|
| 5.00 | 0.17 | 0.00 | 0.85 |
| 5.50 | 0.02 | 0.05 | 0.04 |
| 6.00 | 0.00 | 0.02 | 0.01 |
| 6.50 | 0.06 | 0.12 | 0.09 |
| 7.00 | 0.2 | 0.0 | 0.1 |
| 7.50 | 0.1 | 0.12 | 0.1 |
| 8.00 | 0.46 | 0.25 | 0.35 |
| 8.50 | 0.23 | 0.67 | 0.45 |
| 9.00 | 0.13 | 0.05 | 0.09 |
| 9.50 | 0.45 | 0.06 | 0.25 |
| 10.00 | 0.28 | 0.34 | 0.62 |
| 10.50 | 1.10 | 1.50 | 1.30 |
| 11.00 | 0.42 | 0.20 | 0.31 |
| 11.50 | 0.68 | 0.40 | 1.10 |
| 12.00 | 0.38 | 0.22 | 0.30 |
| 16.00 | 0.55 | 1.00 | 0.78 |
| 24.00 | 0.50 | 0.02 | 0.26 |

Pharmacokinetic Estimates

| | |
|---|---|
| Half-life (hr) | 18.00 |
| Tmax (hr) | 10.50 |
| Cmax (ng/mL) | 1.3 |
| AUC 0-T (hr * ng/mL) | 8.9 |
| % Bioavailability | 61% |

TABLE 6

INTRAVENOUS PHARMACOKINETIC
ANALYSIS FOR MIPROCELLE-INSULIN IN DOGS
Miprocelle-Insulin
Analytical Range 0.01-3000 (ng/mL)
TTI RFA: 3021
IV Dose 0.01

| Time (hr) | Animal #/Concentration (ng/mL) 71 | 72 | Mean |
|---|---|---|---|
| 0.03 | 50.2 | 27 | 39 |
| 0.08 | 26.6 | 21 | 24 |
| 0.17 | 15.9 | 11.4 | 13.7 |
| 0.25 | 10.10 | 6.50 | 8.30 |
| 0.33 | 7.60 | 3.40 | 5.50 |
| 0.42 | 5.90 | 2.70 | 4.30 |

TABLE 6-continued

INTRAVENOUS PHARMACOKINETIC
ANALYSIS FOR MIPROCELLE-INSULIN IN DOGS
Miprocelle-Insulin
Analytical Range 0.01-3000 (ng/mL)
TTI RFA: 3021
IV Dose 0.01

| | | | |
|---|---|---|---|
| 1 | 2.5 | 0.7 | 1.60 |
| 2 | 1.2 | 0.2 | 0.7 |
| 3 | 0.00 | 0.00 | 0.0 |
| 4 | 0.02 | 0.04 | 0.03 |

| | |
|---|---|
| Half-life (hr) | 0.23 |
| Tmax (hr) | 0.03 |
| Cmax (ng/mL) | 38.5 |
| AUC 0-T (hr * ng/mL) | 7.4 |

EXAMPLE 15

Oral Bioavailability and Pharmacokinetic Studies in Rats

Preliminary studies for oral bioavailability and pharmacokinetics in rats were conducted with various insulin formulations (albumin-insulin (example 10), IgG-insulin (example 13) and lactoferrin-insulin (example 12) were administered to rats at a volume of 0.2 mL at 230-250 mg between the gum and lips. The formulations were spotted throughout the gum and lip interface so they were evenly distributed. Blood samples were withdrawn via retro-orbital bleed at the times shown in Tables 7-8.

Control animals showed no human insulin at any time. Human insulin appeared in the blood for all treatment between 4-5 hours.

| Composition | Animal No. | Time (h) | Insulin ng/ml | Glucose (mg/Dl) |
|---|---|---|---|---|
| Control | 1 | 3 | <2.00 | 110 |
| | | 4 | <2.00 | 123 |
| | | 5 | <2.00 | 106 |
| | | 14 | <2.00 | 146 |
| | | 18 | <2.00 | 164 |
| | 2 | 3 | <2.00 | 112 |
| | | 4 | <2.00 | 116 |
| | | 5 | <2.00 | 115 |
| | | 14 | <2.00 | |
| | | 18 | <2.00 | 162 |
| | | | <2.00 (mean) | 131 (mean) |
| Lactoferrin-insulin | 1 | 3 | <2.00 | 113 |
| | | 4 | <2.00 | 121 |
| | | 5 | 5.80 | |
| | | 14 | <2.00 | 159 |
| | | 18 | <2.00 | 238 |
| | 2 | 3 | <2.00 | 116 |
| | | 4 | <2.00 | 111 |
| | | 5 | 6.40 | 144 |
| | | 14 | <2.00 | 166 |
| | | 18 | <2.00 | 173 |
| | | | 2.82 (mean) | 146 (mean) |
| Albumin + insulin | 1 | 3 | <2.00 | 124 |
| | | 4 | 18.10 | 109 |
| | | 5 | | |
| | | 14 | <2.00 | 150 |
| | | 18 | <2.00 | 206 |
| | 2 | 3 | QNS | 113 |
| | | 4 | 54.00 | 118 |
| | | 5 | <2.00 | 165 |
| | | 14 | QNS | 115 |
| | | 18 | <2.00 | 209 |
| | | | 11.73 (mean) | 143 (mean) |
| IgG + insulin | 1 | 3 | <2.00 | 121 |
| | | 4 | 54.70 | |
| | | 5 | <2.00 | 132 |

-continued

| Composition | Animal No. | Time (h) | Insulin ng/ml | Glucose (mg/Dl) |
|---|---|---|---|---|
| | | 14 | <2.00 | 166 |
| | | 18 | <2.00 | 278 |
| | 2 | 3 | <2.00 | 110 |
| | | 4 | 5:60 | |
| | | 5 | <2.00 | 108 |
| | | 14 | <2.00 | 171 |
| | | 18 | <2.00 | 208 |
| | | | 7.63 (mean) | 157 (mean) |

EXAMPLE 16

Studies in Human

Composition of Example 12 was administered (0.5 cc) to a human subject for 3 days according the following protocol and the glucose levels were monitored.

| Blood Glucose-Day 1 | | |
|---|---|---|
| Time | Glucose Units | Notes |
| 7:30 PM | 94 | 7:35 PM: Dinner |
| 8:15 PM | 186 | 8:17 PM: Oral Insulin |
| 8:29 PM | 208 | |
| 8:45 PM | 180 | |
| 9:15 PM | 166 | |
| 9:46 PM | 135 | |
| 1:40 AM | 103 | |
| 7:00 AM | 113 | |
| 7:35 AM | 108 | |

| Blood Glucose-Day 2 | | Notes |
|---|---|---|
| Time | Glucose Units | 9:45 AM; Oral Insulin |
| 12:55 PM | 100 | 1:00 PM; Lunch |
| 1:40 PM | 200 | |
| 2:47 PM | 146 | |
| 4:25 PM | 103 | |
| 4:53 PM | 90 | |
| 5:26 PM | 103 | |
| 6:20 PM | 99 | 6:20 PM; Dinner |
| 6:50 PM | 102 | |
| 7:21 PM | 112 | |
| 9:10 PM | 110 | |
| 9:56 PM | 138 | |
| 10:30 PM | 127 | |

| Blood Glucose-Day 3 | | |
|---|---|---|
| Time | Glucose Units | Notes |
| 1:45 PM | 103 | 1:50 PM; Lunch |
| 2:25 PM | 138 | 2:30 PM; More Food |
| 3:02 PM | 153 | |
| 3:25 PM | 134 | 3:30; More Food |
| 3:45 PM | 132 | |
| 3:53 PM | 136 | |
| 4:27 PM | 138 | |
| 4:46 PM | 150 | |
| 6:17 PM | 110 | 6:18 PM; Dinner |
| 6:47 PM | 115 | |
| 7:24 PM | 127 | |
| 8:04 PM | 108 | |
| 9:45 PM | 158 | |
| 10:35 PM | 122 | |

The comparison of data collected on day 1, 2 and 3 indicates (see FIG. 1) that the blood glucose levels were being regulated in a more sustained manner on the third day.

Since modifications will be apparent to those of skill in this art, it is intended that this invention be limited only by the scope of the appended claims.

What is claimed is:

1. A composition, comprising:
    a mucoadhesive protein that is present at a concentration of about 1% by weight up to about 50% by weight of the total weight of the composition;
    an agent for delivery; and
    a delivery vehicle associated with the agent, wherein:
        the composition is formulated as an emulsion and is formulated for mucosal delivery to the oral or gastrointestinal tract mucosa;
        the mucoadhesive protein is associated with the delivery vehicle via a chemical or physical bond, whereby the composition adsorbs to the mucosa for effecting systemic delivery of the agent;
        the composition has a viscosity of about 50,000 cps up to 500,000 cps at about 72° F., whereby the composition is retained on a mucosal surface; and
        the delivery vehicle is selected from among a micelle, inverse micelle, liposome, cubosome and a mixture thereof.

2. The composition of claim 1, wherein the mucoadhesive protein is an immunoglobulin or an albumin.

3. The composition of claim 1, wherein the emulsion is an oil in water or a water in oil emulsion.

4. The composition of claim 1, wherein the agent is dissolved in the oil phase or is dissolved in the water phase.

5. A composition, comprising:
    a mucoadhesive protein present at a concentration of about 9% by weight up to about 10% by weight of the total weight of the composition;
    an agent for delivery; and
    a delivery vehicle associated with the agent; wherein:
        the composition is formulated for mucosal delivery to the oral or gastrointestinal mucosa or nasal or lung mucosa;
        the mucoadhesive protein is associated with the delivery vehicle;
        the mucoadhesive protein is associated with the delivery vehicle via a chemical or physical bond; and
        the delivery vehicle is selected from among a micelle, inverse micelle, liposome, cubosome and a mixture thereof.

6. The composition of claim 5, wherein the mucoadhesive protein is an immunoglobulin or an albumin.

7. The composition of claim 1, wherein the agent alters a body function or alters cosmetic appearance.

8. The composition of claim 1, wherein the agent is a therapeutic agent.

9. The composition of claim 5, wherein the agent alters a body function or alters cosmetic appearance.

10. The composition of claim 5, wherein the agent is a therapeutic agent.

11. The composition of claim 1, wherein the agent is selected from among antidiabetics, anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides, polysaccharides and nutritional supplements.

12. The composition of claim 1, wherein the agent is a hormone or a nutritional supplement.

13. The composition of claim 5, wherein the agent is a hormone or a nutritional supplement.

14. The composition of claim 1, wherein the agent is a drug.

15. The composition of claim 5, wherein the agent is a drug.

16. The composition of claim 1, wherein the agent is a polypeptide drug.

17. The composition of claim 1 that is formulated for oral or nasal administration.

18. The composition claim 1 that has a viscosity of about 100,000 cps up to about 500,000 cps.

19. A method for mucosal delivery of an agent, comprising:
contacting the composition of claim 1 with a mucosal surface of a subject, whereby the agent is delivered into the circulatory system of the subject.

20. The method of claim 19, wherein the agent is selected from among antidiabetics, anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides, polysaccharides, nutritional supplements and combinations thereof.

21. A method for mucosal delivery of an agent, comprising:
contacting the composition of claim 5 with a mucosal surface of a subject, whereby the agent is delivered into the circulatory system of the subject.

22. The composition of claim 1, wherein the mucoadhesive protein is present at a concentration of about 5% by weight up to about 50% by weight of the total weight of the composition.

23. The composition of claim 1, wherein the mucoadhesive protein is present at a concentration of about 1% by weight up to about 11% by weight of the total weight of the composition.

24. A composition, comprising:
a mucoadhesive protein that is present at a concentration of about 1% by weight up to about 50% by weight of the total weight of the composition;
an agent for delivery; and
a delivery vehicle associated with the agent, wherein:
the composition is formulated as an emulsion and is formulated for mucosal delivery to the oral or gastrointestinal tract mucosa;
the mucoadhesive protein is associated with the delivery vehicle via a chemical or physical bond, whereby the composition adsorbs to the mucosa for effecting systemic delivery of the agent; and
the delivery vehicle is selected from among a micelle, inverse micelle, liposome, cubosome and a mixture thereof.

* * * * *